US012642873B1

(12) United States Patent
Bermudes

(10) Patent No.: US 12,642,873 B1
(45) Date of Patent: Jun. 2, 2026

(54) CHIMERIC PROTEIN TOXINS FOR EXPRESSION BY THERAPEUTIC BACTERIA

(71) Applicant: David Gordon Bermudes, Woodland Hills, CA (US)

(72) Inventor: David Gordon Bermudes, Woodland Hills, CA (US)

( * ) Notice: Subject to any disclaimer, the term of this patent is extended or adjusted under 35 U.S.C. 154(b) by 1284 days.

(21) Appl. No.: 17/486,595

(22) Filed: Sep. 27, 2021

Related U.S. Application Data

(63) Continuation of application No. 15/835,093, filed on Dec. 7, 2017, now Pat. No. 11,129,906.

(60) Provisional application No. 62/431,201, filed on Dec. 7, 2016.

(51) Int. Cl.
| | |
|---|---|
| *A61P 35/00* | (2006.01) |
| *A61K 38/16* | (2006.01) |
| *A61K 45/06* | (2006.01) |
| *A61K 48/00* | (2006.01) |
| *C07K 14/005* | (2006.01) |
| *C07K 14/195* | (2006.01) |
| *C07K 14/255* | (2006.01) |
| *C12N 15/70* | (2006.01) |
| *C12N 15/74* | (2006.01) |

(52) U.S. Cl.
CPC .......... *A61K 48/005* (2013.01); *A61K 38/162* (2013.01); *A61K 38/164* (2013.01); *A61K 45/06* (2013.01); *C07K 14/005* (2013.01); *C07K 14/255* (2013.01); *C12N 15/70* (2013.01); *C12N 15/74* (2013.01); *C07K 2319/00* (2013.01); *C12N 2710/00022* (2013.01); *C12N 2710/00033* (2013.01)

(58) Field of Classification Search
None
See application file for complete search history.

(56) References Cited

U.S. PATENT DOCUMENTS

| | | |
|---|---|---|
| 4,436,727 A | 3/1984 | Ribi |
| 4,703,008 A | 10/1987 | Lin |
| 4,906,567 A | 3/1990 | Connelly |
| 5,021,234 A | 6/1991 | Ehrenfeld |
| D320,325 S | 10/1991 | Barfield |
| 5,055,294 A | 10/1991 | Gilroy |
| 5,057,417 A | 10/1991 | Hammonds et al. |
| 5,082,927 A | 1/1992 | Pastan et al. |
| 5,087,569 A | 2/1992 | Gabay et al. |
| 5,098,833 A | 3/1992 | Lasky et al. |
| 5,116,964 A | 5/1992 | Capon et al. |
| 5,126,257 A | 6/1992 | Gabay et al. |
| 5,143,830 A | 9/1992 | Holland et al. |
| 5,143,905 A | 9/1992 | Sivasubramanian et al. |
| 5,152,980 A | 10/1992 | Strom et al. |
| 5,169,764 A | 12/1992 | Shooter et al. |
| 5,177,308 A | 1/1993 | Barton et al. |

| | | |
|---|---|---|
| 5,202,422 A | 4/1993 | Hiatt et al. |
| 5,206,353 A | 4/1993 | Berger et al. |
| 5,223,409 A | 6/1993 | Ladner et al. |
| 5,238,839 A | 8/1993 | Cantor et al. |
| 5,250,515 A | 10/1993 | Fuchs et al. |
| 5,254,799 A | 10/1993 | De Greve et al. |
| 5,278,049 A | 1/1994 | Baker et al. |
| 5,281,530 A | 1/1994 | Sick et al. |
| 5,290,914 A | 3/1994 | Wilcox et al. |
| 5,306,628 A | 4/1994 | Sivasubramanian et al. |
| 5,306,631 A | 4/1994 | Harrison et al. |
| 5,316,933 A | 5/1994 | Yoshimatsu et al. |
| 5,317,096 A | 5/1994 | De Greve et al. |
| 5,318,900 A | 6/1994 | Habuka et al. |
| 5,328,984 A | 7/1994 | Pastan et al. |
| 5,328,985 A | 7/1994 | Sano et al. |
| 5,338,724 A | 8/1994 | Gabay et al. |
| 5,344,762 A | 9/1994 | Karapetian |
| 5,349,124 A | 9/1994 | Fischhoff et al. |
| 5,354,675 A | 10/1994 | Iida et al. |
| 5,356,795 A | 10/1994 | Leonard et al. |
| 5,356,804 A | 10/1994 | Desnick et al. |
| 5,366,874 A | 11/1994 | Eidels et al. |
| 5,376,567 A | 12/1994 | McCormick et al. |
| 5,380,831 A | 1/1995 | Adang et al. |
| 5,382,524 A | 1/1995 | Desnick et al. |
| 5,387,676 A | 2/1995 | Zavada et al. |
| 5,387,744 A | 2/1995 | Curtiss, III et al. |
| 5,389,368 A | 2/1995 | Gurtiss, III |
| 5,399,490 A | 3/1995 | Balganesh et al. |
| 5,403,484 A | 4/1995 | Ladner et al. |
| 5,424,065 A | 6/1995 | Curtiss, III et al. |
| 5,428,143 A | 6/1995 | Berger et al. |
| 5,439,808 A | 8/1995 | Blake et al. |
| 5,455,165 A | 10/1995 | Capon et al. |
| 5,458,878 A | 10/1995 | Pastan et al. |
| 5,460,961 A | 10/1995 | Deby et al. |
| 5,466,463 A | 11/1995 | Ford |
| 5,466,672 A | 11/1995 | Kushnaryov et al. |
| 5,468,485 A | 11/1995 | Curtiss, III |
| 5,470,719 A | 11/1995 | Meng et al. |
| 5,491,075 A | 2/1996 | Desnick et al. |
| 5,492,702 A | 2/1996 | Domingues |
| 5,495,001 A | 2/1996 | McGrogan et al. |
| 5,506,139 A | 4/1996 | Loosmore et al. |
| 5,508,192 A | 4/1996 | Georgiou et al. |
| 5,508,264 A | 4/1996 | Bradfisch et al. |

(Continued)

OTHER PUBLICATIONS

Rabanal et al, A bioinspired peptide scaffold with high antibiotic activity and low in vivo toxicity, Scientific reports, 2014, pp. 1-11.*

*Primary Examiner* — Maria Marvich
(74) *Attorney, Agent, or Firm* — Hoffberg & Associates; Steven M. Hoffberg

(57) ABSTRACT

Bacteria with tumor-targeting capability express, surface displayed, secreted and/or released modified chimeric therapeutic proteins with enhanced therapeutic activity against a neoplastic tissue including solid tumors, lymphomas and leukemias. The bacteria may be attenuated, non-pathogenic, low pathogenic or a probiotic. The chimeric proteins may be protease sensitive and may optionally be further accompanied by co-expression of a secreted protease inhibitor as a separate molecule or as a fusion.

18 Claims, 3 Drawing Sheets

Specification includes a Sequence Listing.

(56)　　References Cited

U.S. PATENT DOCUMENTS

| | | |
|---|---|---|
| 5,512,658 A | 4/1996 | Pastan et al. |
| 5,512,661 A | 4/1996 | Shooter et al. |
| 5,514,582 A | 5/1996 | Capon et al. |
| 5,525,502 A | 6/1996 | Thireos et al. |
| 5,527,883 A | 6/1996 | Thompson et al. |
| 5,529,932 A | 6/1996 | Lorenzetti et al. |
| 5,543,312 A | 8/1996 | Mellors et al. |
| 5,545,553 A | 8/1996 | Gotschlich |
| 5,545,565 A | 8/1996 | De Greve et al. |
| 5,562,907 A | 10/1996 | Arnon |
| 5,567,600 A | 10/1996 | Adang et al. |
| 5,567,862 A | 10/1996 | Adang et al. |
| 5,569,597 A | 10/1996 | Grimsley et al. |
| 5,571,544 A | 11/1996 | Domingues |
| 5,571,698 A | 11/1996 | Ladner et al. |
| 5,583,010 A | 12/1996 | Baumbach et al. |
| 5,585,232 A | 12/1996 | Farr |
| 5,585,269 A | 12/1996 | Earp, III et al. |
| 5,587,455 A | 12/1996 | Berger et al. |
| 5,589,337 A | 12/1996 | Farr |
| 5,591,641 A | 1/1997 | Thorner et al. |
| 5,593,881 A | 1/1997 | Thompson et al. |
| 5,593,882 A | 1/1997 | Erbe et al. |
| 5,602,030 A | 2/1997 | Ingrahm et al. |
| 5,602,095 A | 2/1997 | Pastan et al. |
| 5,604,115 A | 2/1997 | Sladek et al. |
| 5,604,201 A | 2/1997 | Thomas et al. |
| 5,614,191 A | 3/1997 | Puri et al. |
| 5,616,482 A | 4/1997 | Williams |
| 5,624,816 A | 4/1997 | Carraway et al. |
| 5,624,832 A | 4/1997 | Fukuda et al. |
| 5,631,150 A | 5/1997 | Harkki et al. |
| 5,631,156 A | 5/1997 | Xiong et al. |
| 5,631,228 A | 5/1997 | Oppenheim et al. |
| 5,635,484 A | 6/1997 | Ayres et al. |
| 5,635,599 A | 6/1997 | Pastan et al. |
| 5,651,965 A | 7/1997 | Payne |
| 5,652,122 A | 7/1997 | Frankel et al. |
| 5,656,436 A | 8/1997 | Loosmore et al. |
| 5,665,353 A | 9/1997 | Loosmore et al. |
| 5,665,357 A | 9/1997 | Rose et al. |
| 5,670,617 A | 9/1997 | Frankel et al. |
| 5,674,980 A | 10/1997 | Frankel et al. |
| 5,677,148 A | 10/1997 | Williams |
| 5,683,868 A | 11/1997 | LaRossa et al. |
| 5,686,600 A | 11/1997 | Carozzi et al. |
| 5,703,039 A | 12/1997 | Williams et al. |
| 5,705,151 A | 1/1998 | Dow et al. |
| 5,705,156 A | 1/1998 | Pastan et al. |
| 5,705,163 A | 1/1998 | Pastan et al. |
| 5,712,369 A | 1/1998 | Old et al. |
| 5,726,037 A | 3/1998 | Bodary et al. |
| 5,731,163 A | 3/1998 | Vandyk et al. |
| 5,733,543 A | 3/1998 | Nabel et al. |
| 5,733,760 A | 3/1998 | Lu et al. |
| 5,747,287 A | 5/1998 | Blake et al. |
| 5,747,326 A | 5/1998 | Gerardy-Schahn et al. |
| 5,747,641 A | 5/1998 | Frankel et al. |
| 5,747,659 A | 5/1998 | Fioretti et al. |
| 5,760,181 A | 6/1998 | De Greve et al. |
| 5,763,250 A | 6/1998 | Williams et al. |
| 5,767,241 A | 6/1998 | McEver |
| 5,767,372 A | 6/1998 | De Greve et al. |
| 5,770,420 A | 6/1998 | Lowe et al. |
| 5,776,755 A | 7/1998 | Alitalo et al. |
| 5,783,431 A | 7/1998 | Peterson et al. |
| 5,786,179 A | 7/1998 | Kousoulas et al. |
| 5,786,186 A | 7/1998 | Lancashire et al. |
| 5,804,604 A | 9/1998 | Frankel et al. |
| 5,821,081 A | 10/1998 | Boyd et al. |
| 5,821,238 A | 10/1998 | Pastan et al. |
| 5,824,485 A | 10/1998 | Thompson et al. |
| 5,824,502 A | 10/1998 | Honjo et al. |
| 5,824,509 A | 10/1998 | Aggarwal et al. |
| 5,824,538 A | 10/1998 | Branstrom et al. |
| 5,827,514 A | 10/1998 | Bradfisch et al. |
| 5,830,702 A | 11/1998 | Portnoy et al. |
| 5,837,488 A | 11/1998 | Garfinkel et al. |
| 5,837,500 A | 11/1998 | Ladner et al. |
| 5,840,554 A | 11/1998 | Thompson et al. |
| 5,840,840 A | 11/1998 | Rybak et al. |
| 5,843,707 A | 12/1998 | Larsen et al. |
| 5,843,882 A | 12/1998 | Boyd et al. |
| 5,843,898 A | 12/1998 | De Greve et al. |
| 5,849,702 A | 12/1998 | Garfinkel et al. |
| 5,854,044 A | 12/1998 | Pastan et al. |
| 5,863,745 A | 1/1999 | Fitzgerald et al. |
| 5,863,758 A | 1/1999 | Oppermann et al. |
| 5,863,891 A | 1/1999 | Williams et al. |
| 5,869,045 A | 2/1999 | Hellstrom et al. |
| 5,869,302 A | 2/1999 | Loosmore et al. |
| 5,877,012 A | 3/1999 | Estruch et al. |
| 5,877,159 A | 3/1999 | Powell et al. |
| 5,879,686 A | 3/1999 | Blake et al. |
| 5,902,742 A | 5/1999 | Petter et al. |
| 5,912,141 A | 6/1999 | Brojatsch et al. |
| 5,912,230 A | 6/1999 | Oppenheim et al. |
| 5,919,456 A | 7/1999 | Puri et al. |
| 5,925,521 A | 7/1999 | Bandman et al. |
| 5,928,892 A | 7/1999 | Hourcade et al. |
| 5,932,209 A | 8/1999 | Thompson et al. |
| 5,932,471 A | 8/1999 | Williams et al. |
| 5,935,573 A | 8/1999 | Loosmore et al. |
| 5,939,297 A | 8/1999 | Loosmore et al. |
| 5,945,102 A | 8/1999 | de Faire et al. |
| 5,945,322 A | 8/1999 | Gotschlich |
| 5,955,073 A | 9/1999 | Rybak et al. |
| 5,955,347 A | 9/1999 | Lowe |
| 5,958,406 A | 9/1999 | de Faire et al. |
| 5,962,430 A | 10/1999 | Loosmore et al. |
| 5,962,653 A | 10/1999 | Boyd et al. |
| 5,965,382 A | 10/1999 | Koths et al. |
| 5,965,385 A | 10/1999 | Read et al. |
| 5,965,415 A | 10/1999 | Radman et al. |
| 5,965,428 A | 10/1999 | Gilmer et al. |
| 5,976,852 A | 11/1999 | Cheng et al. |
| 5,977,304 A | 11/1999 | Read et al. |
| 5,980,896 A | 11/1999 | Hellstrom et al. |
| 5,981,503 A | 11/1999 | Loosmore et al. |
| 5,989,868 A | 11/1999 | Harrison et al. |
| 5,993,827 A | 11/1999 | Sim et al. |
| 5,994,625 A | 11/1999 | Melchers et al. |
| 5,997,881 A | 12/1999 | Powell et al. |
| 5,998,587 A | 12/1999 | Boyd et al. |
| 6,004,562 A | 12/1999 | Campagnari |
| 6,005,089 A | 12/1999 | Lanza et al. |
| 6,011,002 A | 1/2000 | Pastan et al. |
| 6,013,523 A | 1/2000 | Adang et al. |
| 6,015,876 A | 1/2000 | Boyd |
| 6,015,891 A | 1/2000 | Adang et al. |
| 6,015,897 A | 1/2000 | Theodore et al. |
| 6,017,743 A | 1/2000 | Tsuji et al. |
| 6,018,022 A | 1/2000 | Read et al. |
| 6,020,145 A | 2/2000 | Hellstrom et al. |
| 6,020,183 A | 2/2000 | Loosmore et al. |
| 6,022,729 A | 2/2000 | Steinbuchel et al. |
| 6,022,855 A | 2/2000 | Thomas et al. |
| 6,025,183 A | 2/2000 | Soreq et al. |
| 6,025,342 A | 2/2000 | Loosmore et al. |
| 6,030,612 A | 2/2000 | de Faire et al. |
| 6,030,624 A | 2/2000 | Russell et al. |
| 6,030,780 A | 2/2000 | Vinkemeier et al. |
| 6,033,663 A | 3/2000 | Ketcham et al. |
| 6,033,890 A | 3/2000 | Jakobovits et al. |
| 6,037,123 A | 3/2000 | Benton et al. |
| 6,037,159 A | 3/2000 | Uchimura et al. |
| 6,037,526 A | 3/2000 | Grimsley et al. |
| 6,040,156 A | 3/2000 | Kawasaki et al. |
| 6,051,237 A | 4/2000 | Paterson |
| 6,051,405 A | 4/2000 | FitzGerald et al. |
| 6,054,309 A | 4/2000 | Hirabayashi et al. |
| 6,054,312 A | 4/2000 | Larocca et al. |
| 6,069,127 A | 5/2000 | Koths et al. |
| 6,069,301 A | 5/2000 | Carozzi et al. |

(56)        References Cited

U.S. PATENT DOCUMENTS

| | | | |
|---|---|---|---|
| 6,074,840 A | 6/2000 | Bonadio et al. |
| 6,080,849 A | 6/2000 | Bermudes et al. |
| 6,083,688 A | 7/2000 | Lanza et al. |
| 6,086,900 A | 7/2000 | Draper |
| 6,090,567 A | 7/2000 | Jakobovits et al. |
| 6,090,582 A | 7/2000 | Kikly et al. |
| 6,090,931 A | 7/2000 | Edwards et al. |
| 6,093,539 A | 7/2000 | Maddon et al. |
| 6,096,529 A | 8/2000 | Gilbert et al. |
| 6,107,279 A | 8/2000 | Estruch et al. |
| 6,107,546 A | 8/2000 | De Greve et al. |
| 6,110,899 A | 8/2000 | Lonetto |
| 6,111,089 A | 8/2000 | Fukuda |
| 6,114,125 A | 9/2000 | Loosmore et al. |
| 6,117,651 A | 9/2000 | Schultz et al. |
| 6,117,977 A | 9/2000 | Lasky et al. |
| 6,124,446 A | 9/2000 | Hillman et al. |
| 6,137,033 A | 10/2000 | Estruch et al. |
| 6,140,066 A | 10/2000 | Lorberboum-Galski et al. |
| 6,143,551 A | 11/2000 | Goebel |
| 6,146,845 A | 11/2000 | Kikly et al. |
| 6,146,849 A | 11/2000 | Pierce et al. |
| 6,147,057 A | 11/2000 | Loosmore et al. |
| 6,150,170 A | 11/2000 | Powell et al. |
| 6,153,580 A | 11/2000 | Loosmore et al. |
| 6,166,290 A | 12/2000 | Rea et al. |
| 6,172,281 B1 | 1/2001 | Van Mellaert et al. |
| 6,177,083 B1 | 1/2001 | Lubitz |
| 6,187,541 B1 | 2/2001 | Benton et al. |
| 6,190,657 B1 | 2/2001 | Pawelek et al. |
| 6,193,982 B1 | 2/2001 | Boyd |
| 6,200,779 B1 | 3/2001 | Lonetto |
| 6,207,156 B1 | 3/2001 | Kuchroo et al. |
| 6,207,417 B1 | 3/2001 | Zsebo et al. |
| 6,207,427 B1 | 3/2001 | Hashimoto et al. |
| 6,207,648 B1 | 3/2001 | Waxman et al. |
| 6,217,869 B1 | 4/2001 | Meyer et al. |
| 6,218,148 B1 | 4/2001 | Zsebo et al. |
| 6,228,588 B1 | 5/2001 | Benton et al. |
| 6,232,110 B1 | 5/2001 | Pallas et al. |
| 6,238,914 B1 | 5/2001 | Boyce |
| 6,242,210 B1 | 6/2001 | Bjorck et al. |
| 6,242,211 B1 | 6/2001 | Peterson et al. |
| 6,245,737 B1 | 6/2001 | Boyd et al. |
| 6,245,892 B1 | 6/2001 | Oaks et al. |
| 6,248,329 B1 | 6/2001 | Chandrashekar et al. |
| 6,251,406 B1 | 6/2001 | Haefliger et al. |
| 6,261,800 B1 | 7/2001 | Nikolics et al. |
| 6,268,193 B1 | 7/2001 | Lowe |
| 6,271,011 B1 | 8/2001 | Lee et al. |
| 6,271,368 B1 | 8/2001 | Lentzen et al. |
| 6,274,339 B1 | 8/2001 | Moore et al. |
| 6,277,379 B1 | 8/2001 | Oaks et al. |
| 6,277,574 B1 | 8/2001 | Walker et al. |
| 6,280,989 B1 | 8/2001 | Kapitonov et al. |
| 6,284,493 B1 | 9/2001 | Roth |
| 6,291,156 B1 | 9/2001 | Estruch et al. |
| 6,296,843 B1 | 10/2001 | Debinski |
| 6,302,685 B1 | 10/2001 | Lobel et al. |
| 6,303,571 B1 | 10/2001 | Lonetto |
| 6,310,046 B1 | 10/2001 | Duffy et al. |
| 6,312,907 B1 | 11/2001 | Guo et al. |
| 6,316,003 B1 | 11/2001 | Frankel et al. |
| 6,316,609 B1 | 11/2001 | Dillon et al. |
| 6,323,003 B1 | 11/2001 | Black, Jr. |
| 6,329,002 B1 | 12/2001 | Kim et al. |
| 6,331,413 B1 | 12/2001 | Adler et al. |
| 6,333,182 B1 | 12/2001 | Coleman et al. |
| 6,333,396 B1 | 12/2001 | Filpula et al. |
| 6,338,953 B1 | 1/2002 | Boyce et al. |
| 6,338,955 B2 | 1/2002 | Oguri et al. |
| 6,342,382 B1 | 1/2002 | Gotschlich |
| 6,348,344 B1 | 2/2002 | Ayal-Hershkovitz et al. |
| 6,355,790 B1 | 3/2002 | Rosenblatt et al. |
| 6,358,724 B1 | 3/2002 | Wong-Madden et al. |
| 6,365,381 B2 | 4/2002 | Hashimoto et al. |
| 6,369,213 B1 | 4/2002 | Schnepf et al. |
| 6,375,947 B1 | 4/2002 | Bolen et al. |
| 6,376,234 B1 | 4/2002 | Grimsley et al. |
| 6,379,913 B1 | 4/2002 | Bandman et al. |
| 6,383,496 B1 | 5/2002 | Curtiss, III et al. |
| 6,387,648 B1 | 5/2002 | Levi et al. |
| 6,387,702 B1 | 5/2002 | Stemmer |
| 6,395,513 B1 | 5/2002 | Foster et al. |
| 6,399,326 B1 | 6/2002 | Chiang et al. |
| 6,399,336 B1 | 6/2002 | Paulson et al. |
| 6,410,012 B1 | 6/2002 | Sizemore et al. |
| 6,410,687 B1 | 6/2002 | Vale et al. |
| 6,416,988 B1 | 7/2002 | Conklin et al. |
| 6,420,135 B1 | 7/2002 | Kunsch et al. |
| 6,420,149 B1 | 7/2002 | Fukuda et al. |
| 6,420,336 B1 | 7/2002 | Boyd |
| 6,420,527 B1 | 7/2002 | Bolen et al. |
| 6,423,525 B1 | 7/2002 | Landry |
| 6,428,788 B1 | 8/2002 | Debinski et al. |
| 6,428,790 B1 | 8/2002 | Boyd |
| 6,428,999 B1 | 8/2002 | Ito et al. |
| 6,429,304 B1 | 8/2002 | Vale et al. |
| 6,429,360 B1 | 8/2002 | Estruch et al. |
| 6,436,687 B1 | 8/2002 | Yu et al. |
| 6,447,777 B1 | 9/2002 | Terman et al. |
| 6,447,784 B1 | 9/2002 | Bermudes et al. |
| 6,451,312 B1 | 9/2002 | Thorpe |
| 6,455,288 B1 | 9/2002 | Jakobovits et al. |
| 6,458,573 B1 | 10/2002 | Landry |
| 6,472,518 B1 | 10/2002 | Ribot et al. |
| 6,475,482 B1 | 11/2002 | Bermudes et al. |
| 6,475,763 B1 | 11/2002 | Ayal-Hershkovitz et al. |
| 6,482,647 B1 | 11/2002 | Stemmer |
| 6,492,152 B1 | 12/2002 | Canfield et al. |
| 6,500,419 B1 | 12/2002 | Hone et al. |
| 6,503,744 B1 | 1/2003 | Gilbert et al. |
| 6,506,550 B1 | 1/2003 | Fulton et al. |
| 6,514,724 B1 | 2/2003 | McMahon et al. |
| 6,518,061 B1 | 2/2003 | Puri et al. |
| 6,521,439 B2 | 2/2003 | Folkman et al. |
| 6,524,792 B1 | 2/2003 | Renner et al. |
| 6,524,820 B1 | 2/2003 | Pierce et al. |
| 6,531,133 B1 | 3/2003 | Lorberboum-Galski et al. |
| 6,531,306 B1 | 3/2003 | Hockensmith et al. |
| 6,534,311 B2 | 3/2003 | Stewart et al. |
| 6,537,558 B2 | 3/2003 | Kaniga |
| 6,545,126 B1 | 4/2003 | Johnson et al. |
| 6,548,287 B1 | 4/2003 | Powell et al. |
| 6,551,618 B2 | 4/2003 | Baird et al. |
| 6,551,795 B1 | 4/2003 | Rubenfield et al. |
| 6,555,343 B1 | 4/2003 | DeSauvage et al. |
| 6,558,953 B1 | 5/2003 | Gonsalves et al. |
| 6,570,000 B1 | 5/2003 | Maddon et al. |
| 6,570,005 B1 | 5/2003 | Schnepf et al. |
| 6,573,082 B1 | 6/2003 | Choi et al. |
| 6,576,232 B1 | 6/2003 | Debinski et al. |
| 6,582,948 B1 | 6/2003 | Bolen et al. |
| 6,582,950 B1 | 6/2003 | Smith et al. |
| 6,585,975 B1 | 7/2003 | Kleanthous et al. |
| 6,586,392 B2 | 7/2003 | Boyd |
| 6,596,849 B1 | 7/2003 | Roffler et al. |
| 6,599,912 B1 | 7/2003 | Au et al. |
| 6,605,286 B2 | 8/2003 | Steidler et al. |
| 6,605,592 B2 | 8/2003 | Ni et al. |
| 6,605,697 B1 | 8/2003 | Kwon et al. |
| 6,607,897 B2 | 8/2003 | Vogel et al. |
| 6,617,118 B2 | 9/2003 | Roffler et al. |
| 6,630,303 B1 | 10/2003 | Benton et al. |
| 6,632,935 B2 | 10/2003 | Shigenobu et al. |
| 6,635,246 B1 | 10/2003 | Barrett et al. |
| 6,635,468 B1 | 10/2003 | Ashkenazi et al. |
| 6,635,740 B1 | 10/2003 | Enright et al. |
| 6,638,718 B1 | 10/2003 | Benton et al. |
| 6,638,912 B2 | 10/2003 | Bhatnagar et al. |
| 6,642,041 B2 | 11/2003 | Chen et al. |
| 6,645,490 B2 | 11/2003 | Yarkoni et al. |
| 6,646,113 B1 | 11/2003 | Dreyfuss et al. |
| 6,673,915 B1 | 1/2004 | Luster et al. |

(56) References Cited

U.S. PATENT DOCUMENTS

| | | | |
|---|---|---|---|
| 6,680,058 B1 | 1/2004 | Enright et al. |
| 6,680,187 B2 | 1/2004 | Moeckel et al. |
| 6,680,374 B2 | 1/2004 | Oaks et al. |
| 6,682,728 B1 | 1/2004 | Finkel et al. |
| 6,682,729 B1 | 1/2004 | Powell et al. |
| 6,682,910 B2 | 1/2004 | Powell |
| 6,685,935 B1 | 2/2004 | Pawelek et al. |
| 6,689,586 B2 | 2/2004 | Moeckel et al. |
| 6,689,604 B1 | 2/2004 | Gilbert et al. |
| 6,692,942 B2 | 2/2004 | Filpula et al. |
| 6,693,183 B2 | 2/2004 | Natsuka et al. |
| 6,696,411 B1 | 2/2004 | MacLeod |
| 6,699,705 B2 | 3/2004 | Gilbert et al. |
| 6,699,969 B1 | 3/2004 | Vale et al. |
| 6,703,223 B2 | 3/2004 | Bathe et al. |
| 6,703,233 B1 | 3/2004 | Galen |
| 6,709,656 B1 | 3/2004 | Boren et al. |
| 6,709,830 B2 | 3/2004 | Witte et al. |
| 6,709,834 B2 | 3/2004 | Gilbert et al. |
| 6,713,277 B1 | 3/2004 | Moore et al. |
| 6,716,582 B2 | 4/2004 | Gonye et al. |
| 6,720,410 B2 | 4/2004 | Cerny et al. |
| 6,723,540 B1 | 4/2004 | Harkki et al. |
| 6,727,086 B2 | 4/2004 | Bathe et al. |
| 6,734,002 B2 | 5/2004 | Bathe et al. |
| 6,743,577 B2 | 6/2004 | Boyd |
| 6,743,893 B2 | 6/2004 | Engler et al. |
| 6,746,671 B2 | 6/2004 | Steidler et al. |
| 6,746,854 B2 | 6/2004 | Bathe et al. |
| 6,752,992 B2 | 6/2004 | Schnepf et al. |
| 6,753,164 B2 | 6/2004 | Ni et al. |
| 6,759,215 B1 | 7/2004 | Zsebo et al. |
| 6,759,224 B2 | 7/2004 | Farwick et al. |
| 6,759,230 B1 | 7/2004 | Bulla, Jr. et al. |
| 6,764,853 B2 | 7/2004 | Filpula et al. |
| 6,770,466 B2 | 8/2004 | Shi et al. |
| 6,770,632 B1 | 8/2004 | Aghi et al. |
| 6,777,206 B2 | 8/2004 | Farwick et al. |
| 6,780,405 B1 | 8/2004 | Curtiss, III et al. |
| 6,780,624 B2 | 8/2004 | Gotschlich |
| 6,780,847 B2 | 8/2004 | Boyd |
| 6,783,966 B1 | 8/2004 | Kojima et al. |
| 6,783,967 B2 | 8/2004 | Moeckel et al. |
| 6,783,971 B2 | 8/2004 | Coleman et al. |
| 6,784,164 B2 | 8/2004 | Masure et al. |
| 6,787,643 B2 | 9/2004 | Dillon et al. |
| 6,797,509 B1 | 9/2004 | Dunican et al. |
| 6,803,192 B1 | 10/2004 | Chen |
| 6,811,788 B2 | 11/2004 | Yu |
| 6,812,006 B2 | 11/2004 | Moeckel et al. |
| 6,818,449 B2 | 11/2004 | Fong et al. |
| 6,822,071 B1 | 11/2004 | Stephens et al. |
| 6,822,085 B2 | 11/2004 | Farwick et al. |
| 6,824,782 B2 | 11/2004 | Whitlow et al. |
| 6,825,019 B2 | 11/2004 | Gilbert et al. |
| 6,825,029 B2 | 11/2004 | Dunican et al. |
| 6,825,030 B2 | 11/2004 | Mockel et al. |
| 6,828,121 B2 | 12/2004 | Chen |
| 6,828,146 B2 | 12/2004 | Desnoyers et al. |
| 6,828,419 B2 | 12/2004 | Adler et al. |
| 6,831,060 B2 | 12/2004 | DeSauvage et al. |
| 6,833,130 B1 | 12/2004 | Paton et al. |
| 6,833,253 B2 | 12/2004 | Choi |
| 6,833,255 B1 | 12/2004 | Stewart et al. |
| 6,838,267 B2 | 1/2005 | Moeckel et al. |
| 6,841,535 B2 | 1/2005 | Divita et al. |
| 6,841,718 B2 | 1/2005 | Alberte et al. |
| 6,844,176 B1 | 1/2005 | Bathe et al. |
| 6,844,178 B2 | 1/2005 | Bolen et al. |
| 6,846,484 B2 | 1/2005 | Vallera et al. |
| 6,846,667 B1 | 1/2005 | Crooke et al. |
| 6,855,688 B2 | 2/2005 | McKerracher |
| 6,858,407 B2 | 2/2005 | Feder et al. |
| 6,858,415 B2 | 2/2005 | Coleman et al. |
| 6,861,231 B2 | 3/2005 | Shao |
| 6,863,894 B2 | 3/2005 | Bermudes et al. |
| 6,872,393 B2 | 3/2005 | Whitlow et al. |
| 6,872,526 B2 | 3/2005 | Short et al. |
| 6,872,537 B1 | 3/2005 | Vale et al. |
| 6,875,586 B2 | 4/2005 | Moeckel et al. |
| 6,884,603 B2 | 4/2005 | Debinski et al. |
| 6,884,770 B1 | 4/2005 | Galdes et al. |
| 6,887,663 B1 | 5/2005 | Choi et al. |
| 6,890,744 B2 | 5/2005 | Bathe et al. |
| 6,902,916 B2 | 6/2005 | Moeckel et al. |
| 6,902,932 B2 | 6/2005 | Altman et al. |
| 6,905,867 B2 | 6/2005 | Gilbert et al. |
| 6,911,337 B2 | 6/2005 | Gilbert et al. |
| 6,913,906 B2 | 7/2005 | Bolen et al. |
| 6,913,908 B2 | 7/2005 | Mockel et al. |
| 6,913,919 B2 | 7/2005 | Botstein et al. |
| 6,916,636 B2 | 7/2005 | Marx et al. |
| 6,916,648 B2 | 7/2005 | Goddard et al. |
| 6,916,918 B2 | 7/2005 | Yu et al. |
| 6,919,079 B1 | 7/2005 | Fishman et al. |
| 6,921,651 B2 | 7/2005 | Farwick et al. |
| 6,921,659 B2 | 7/2005 | Joly |
| 6,923,972 B2 | 8/2005 | Bermudes et al. |
| 6,924,134 B2 | 8/2005 | Farwick et al. |
| 6,927,052 B2 | 8/2005 | Bathe et al. |
| 6,929,930 B2 | 8/2005 | Choi et al. |
| 6,933,271 B2 | 8/2005 | Yarkoni et al. |
| 6,936,448 B2 | 8/2005 | Holmes et al. |
| 6,939,692 B2 | 9/2005 | Bathe et al. |
| 6,939,694 B2 | 9/2005 | Mockel et al. |
| 6,939,695 B2 | 9/2005 | Moeckel et al. |
| 6,943,001 B2 | 9/2005 | Zhao et al. |
| 6,943,241 B2 | 9/2005 | Isogai et al. |
| 6,946,262 B2 | 9/2005 | Ferrara et al. |
| 6,946,271 B2 | 9/2005 | Farwick et al. |
| 6,949,372 B2 | 9/2005 | Betenbaugh et al. |
| 6,951,737 B2 | 10/2005 | Desnoyers et al. |
| 6,951,738 B2 | 10/2005 | Ni et al. |
| 6,953,835 B2 | 10/2005 | Fischhoff et al. |
| 6,955,953 B2 | 10/2005 | Yamazaki et al. |
| 6,962,696 B1 | 11/2005 | Bermudes et al. |
| 6,962,703 B2 | 11/2005 | Foster et al. |
| 6,962,800 B2 | 11/2005 | Kiy et al. |
| 6,969,517 B2 | 11/2005 | Gillies et al. |
| 6,972,185 B2 | 12/2005 | Desnoyers et al. |
| 6,972,186 B2 | 12/2005 | Desnoyers et al. |
| 6,974,689 B1 | 12/2005 | Ashkenazi et al. |
| 6,974,696 B2 | 12/2005 | Botstein et al. |
| 6,974,893 B2 | 12/2005 | Shanklin et al. |
| 6,979,538 B2 | 12/2005 | Ladner et al. |
| 6,979,556 B2 | 12/2005 | Simmons et al. |
| 6,979,733 B2 | 12/2005 | Zhao et al. |
| 6,987,096 B1 | 1/2006 | Boyd et al. |
| 6,987,176 B1 | 1/2006 | Guerry et al. |
| 6,992,174 B2 | 1/2006 | Gillies et al. |
| 6,995,000 B2 | 2/2006 | Bathe et al. |
| 6,995,002 B2 | 2/2006 | Molenaar et al. |
| 7,001,884 B2 | 2/2006 | Komiyama et al. |
| 7,015,027 B1 | 3/2006 | Redshaw |
| 7,018,811 B2 | 3/2006 | Botstein et al. |
| 7,019,124 B2 | 3/2006 | Desnoyers et al. |
| 7,022,498 B2 | 4/2006 | Desnoyers et al. |
| 7,026,158 B2 | 4/2006 | Farwick et al. |
| 7,026,449 B2 | 4/2006 | Baker et al. |
| 7,029,875 B2 | 4/2006 | Desnoyers et al. |
| 7,029,904 B2 | 4/2006 | Farwick et al. |
| 7,033,785 B2 | 4/2006 | Desnoyers et al. |
| 7,033,786 B2 | 4/2006 | Baker et al. |
| 7,033,825 B2 | 4/2006 | Goddard et al. |
| 7,033,991 B2 | 4/2006 | Lindberg et al. |
| 7,034,136 B2 | 4/2006 | Goddard et al. |
| 7,037,679 B2 | 5/2006 | Desnoyers et al. |
| 7,037,689 B2 | 5/2006 | Bathe et al. |
| 7,037,710 B2 | 5/2006 | Goddard et al. |
| 7,038,034 B2 | 5/2006 | Farwick et al. |
| 7,041,441 B1 | 5/2006 | Steven et al. |
| 7,041,814 B1 | 5/2006 | Weinstock et al. |
| 7,045,122 B2 | 5/2006 | Nuijten et al. |
| 7,048,935 B2 | 5/2006 | Boyd |

(56)　　　　　　References Cited

U.S. PATENT DOCUMENTS

| | | | |
|---|---|---|---|
| 7,049,096 | B2 | 5/2006 | Feder et al. |
| 7,049,106 | B2 | 5/2006 | Farwick et al. |
| 7,052,702 | B1 | 5/2006 | Duggan et al. |
| 7,052,889 | B2 | 5/2006 | Jenuwein et al. |
| 7,052,903 | B2 | 5/2006 | Black, Jr. |
| 7,053,266 | B2 | 5/2006 | Tuli |
| 7,056,510 | B1 | 6/2006 | Choi et al. |
| 7,056,700 | B2 | 6/2006 | Galen |
| 7,056,721 | B2 | 6/2006 | Dunn-Coleman et al. |
| 7,056,736 | B2 | 6/2006 | Ashkenazi et al. |
| 7,056,737 | B2 | 6/2006 | Feder et al. |
| 7,060,475 | B2 | 6/2006 | Usuda et al. |
| 7,060,479 | B2 | 6/2006 | Dumas Milne Edwards et al. |
| 7,060,812 | B2 | 6/2006 | Desnoyers et al. |
| 7,067,110 | B1 | 6/2006 | Gillies et al. |
| 7,067,288 | B2 | 6/2006 | Molenaar et al. |
| 7,067,306 | B2 | 6/2006 | Singhvi et al. |
| 7,070,979 | B2 | 7/2006 | Botstein et al. |
| 7,074,589 | B1 | 7/2006 | Ullrich et al. |
| 7,074,592 | B2 | 7/2006 | Ashkenazi et al. |
| 7,078,185 | B2 | 7/2006 | Farnet et al. |
| 7,078,186 | B2 | 7/2006 | Ni et al. |
| 7,078,204 | B2 | 7/2006 | Yokoi et al. |
| 7,078,207 | B2 | 7/2006 | Gilbert et al. |
| 7,078,502 | B2 | 7/2006 | Moeckel et al. |
| 7,083,791 | B2 | 8/2006 | Sleeman et al. |
| 7,083,794 | B2 | 8/2006 | Curtiss, III et al. |
| 7,083,942 | B2 | 8/2006 | Bathe et al. |
| 7,083,946 | B2 | 8/2006 | Baker et al. |
| 7,083,978 | B2 | 8/2006 | Desnoyers et al. |
| 7,084,105 | B2 | 8/2006 | Chakrabarty et al. |
| 7,087,404 | B2 | 8/2006 | Desnoyers et al. |
| 7,087,738 | B2 | 8/2006 | Botstein et al. |
| 7,090,835 | B2 | 8/2006 | Gabriel et al. |
| 7,091,315 | B1 | 8/2006 | Ruben et al. |
| 7,091,321 | B2 | 8/2006 | Gillies et al. |
| 7,094,563 | B2 | 8/2006 | Wong-Madden et al. |
| 7,094,567 | B2 | 8/2006 | Ashkenazi et al. |
| 7,094,572 | B2 | 8/2006 | Ramanathan et al. |
| 7,101,690 | B2 | 9/2006 | Moeckel et al. |
| 7,101,977 | B2 | 9/2006 | Rosenblum et al. |
| 7,105,169 | B2 | 9/2006 | Boyd |
| 7,105,302 | B2 | 9/2006 | Bathe et al. |
| 7,105,321 | B2 | 9/2006 | Moeckel et al. |
| 7,109,033 | B2 | 9/2006 | Harper et al. |
| 7,109,315 | B2 | 9/2006 | Bryan et al. |
| 7,112,317 | B2 | 9/2006 | Thorpe et al. |
| 7,115,402 | B2 | 10/2006 | Feder et al. |
| 7,118,879 | B2 | 10/2006 | Ladner et al. |
| 7,119,193 | B2 | 10/2006 | Gottesman et al. |
| 7,122,185 | B2 | 10/2006 | Olson et al. |
| 7,122,358 | B2 | 10/2006 | Feder et al. |
| 7,122,367 | B2 | 10/2006 | Milcamps et al. |
| 7,122,375 | B2 | 10/2006 | Goddard et al. |
| 7,125,541 | B2 | 10/2006 | Thorpe et al. |
| 7,125,548 | B2 | 10/2006 | Smith |
| 7,125,718 | B2 | 10/2006 | Powell et al. |
| 7,129,066 | B2 | 10/2006 | Farwick et al. |
| 7,129,085 | B2 | 10/2006 | Feder et al. |
| 7,129,212 | B2 | 10/2006 | Narva et al. |
| 7,132,283 | B2 | 11/2006 | Fong et al. |
| 7,135,313 | B2 | 11/2006 | Bathe et al. |
| 7,138,252 | B2 | 11/2006 | Bachmann et al. |
| 7,138,258 | B2 | 11/2006 | Gilbert et al. |
| 7,138,259 | B2 | 11/2006 | Beavo et al. |
| 7,141,418 | B2 | 11/2006 | Kunsch et al. |
| 7,144,724 | B2 | 12/2006 | Farwick et al. |
| 7,148,321 | B2 | 12/2006 | Gillies et al. |
| 7,150,872 | B2 | 12/2006 | Whitlow et al. |
| 7,153,678 | B2 | 12/2006 | Jackson et al. |
| 7,157,418 | B1 | 1/2007 | McDonald et al. |
| 7,160,703 | B2 | 1/2007 | Moeckel et al. |
| 7,160,711 | B2 | 1/2007 | Bathe et al. |
| 7,163,797 | B2 | 1/2007 | Ruben et al. |
| 7,166,702 | B1 | 1/2007 | McDonald et al. |
| 7,169,565 | B2 | 1/2007 | Ruben et al. |
| 7,169,904 | B2 | 1/2007 | Gillies et al. |
| 7,169,912 | B2 | 1/2007 | Desnoyers et al. |
| 7,173,105 | B2 | 2/2007 | Moeckel et al. |
| 7,183,066 | B2 | 2/2007 | Fernandez-Salas et al. |
| 7,183,379 | B2 | 2/2007 | Feder et al. |
| 7,186,564 | B2 | 3/2007 | Chen et al. |
| 7,186,804 | B2 | 3/2007 | Gillies et al. |
| 7,189,529 | B2 | 3/2007 | Ashkenazi et al. |
| 7,189,530 | B2 | 3/2007 | Botstein et al. |
| 7,189,539 | B2 | 3/2007 | Ramanathan et al. |
| 7,189,836 | B2 | 3/2007 | Gilbert et al. |
| 7,192,736 | B2 | 3/2007 | McDonald et al. |
| 7,192,933 | B1 | 3/2007 | Boyce |
| 7,195,754 | B1 | 3/2007 | Glatkowski et al. |
| 7,195,757 | B2 | 3/2007 | Curtiss, III et al. |
| 7,198,912 | B2 | 4/2007 | Ramanathan et al. |
| 7,202,056 | B2 | 4/2007 | Lee et al. |
| 7,202,059 | B2 | 4/2007 | Habermann et al. |
| 7,202,061 | B2 | 4/2007 | Farwick et al. |
| 7,202,353 | B2 | 4/2007 | Gilbert et al. |
| 7,205,144 | B2 | 4/2007 | Mockel et al. |
| 7,208,285 | B2 | 4/2007 | Steward et al. |
| 7,208,293 | B2 | 4/2007 | Ladner et al. |
| 7,208,304 | B2 | 4/2007 | Gilbert et al. |
| 7,208,312 | B1 | 4/2007 | Desnoyers et al. |
| 7,208,313 | B2 | 4/2007 | McCart et al. |
| 7,208,466 | B1 | 4/2007 | Foster et al. |
| 7,211,253 | B1 | 5/2007 | Way |
| 7,211,657 | B2 | 5/2007 | Gilbert et al. |
| 7,214,526 | B2 | 5/2007 | Bathe et al. |
| 7,214,792 | B2 | 5/2007 | Bulla et al. |
| 7,217,548 | B2 | 5/2007 | Yoshida et al. |
| 7,217,549 | B2 | 5/2007 | Gilbert et al. |
| 7,217,809 | B2 | 5/2007 | Schultz et al. |
| 7,220,555 | B2 | 5/2007 | Paulson et al. |
| 7,220,848 | B2 | 5/2007 | Gilbert et al. |
| 7,223,557 | B2 | 5/2007 | Lee et al. |
| 7,223,586 | B2 | 5/2007 | Ferrara et al. |
| 7,226,761 | B2 | 6/2007 | Miasnikov et al. |
| 7,226,763 | B2 | 6/2007 | Bathe et al. |
| 7,226,791 | B2 | 6/2007 | Carman et al. |
| 7,229,791 | B2 | 6/2007 | Bathe et al. |
| 7,229,802 | B2 | 6/2007 | Bathe et al. |
| 7,232,672 | B2 | 6/2007 | Weiner et al. |
| 7,235,234 | B1 | 6/2007 | Branstrom et al. |
| 7,238,509 | B2 | 7/2007 | Gilbert et al. |
| 7,244,601 | B2 | 7/2007 | Gilbert et al. |
| 7,244,833 | B2 | 7/2007 | Yu et al. |
| 7,247,296 | B2 | 7/2007 | Redshaw |
| 7,247,717 | B2 | 7/2007 | Chen et al. |
| 7,252,977 | B2 | 8/2007 | Bathe et al. |
| 7,256,267 | B2 | 8/2007 | Chen et al. |
| 7,258,863 | B2 | 8/2007 | Oaks et al. |
| 7,259,296 | B2 | 8/2007 | Schmulling et al. |
| 7,262,039 | B1 | 8/2007 | Narimatsu et al. |
| 7,262,040 | B2 | 8/2007 | Schultz et al. |
| 7,267,973 | B2 | 9/2007 | Backer et al. |
| 7,270,815 | B2 | 9/2007 | Sasisekharan et al. |
| 7,270,984 | B1 | 9/2007 | Pompejus et al. |
| 7,271,243 | B2 | 9/2007 | Dumas Milne Edwards et al. |
| 7,273,706 | B2 | 9/2007 | Feder et al. |
| 7,276,354 | B2 | 10/2007 | Feder et al. |
| 7,279,310 | B2 | 10/2007 | Narimatsu et al. |
| 7,285,635 | B2 | 10/2007 | Rosenblum et al. |
| 7,288,255 | B1 | 10/2007 | Shlomchik et al. |
| 7,291,491 | B2 | 11/2007 | Fukuda et al. |
| 7,297,340 | B2 | 11/2007 | Apicella |
| 7,303,905 | B2 | 12/2007 | Breves et al. |
| 7,306,932 | B2 | 12/2007 | Bathe et al. |
| 7,307,159 | B2 | 12/2007 | DeAngelis |
| 7,309,600 | B2 | 12/2007 | Apicella et al. |
| 7,318,927 | B2 | 1/2008 | Perez et al. |
| 7,318,928 | B2 | 1/2008 | Wu et al. |
| 7,320,791 | B2 | 1/2008 | Roffler et al. |
| 7,320,887 | B2 | 1/2008 | Kottwitz et al. |
| 7,323,549 | B2 | 1/2008 | Lauder et al. |
| 7,326,546 | B2 | 2/2008 | Matsuno et al. |
| 7,326,557 | B2 | 2/2008 | San et al. |

(56)         References Cited

U.S. PATENT DOCUMENTS

| | | | |
|---|---|---|---|
| 7,332,304 B2 | 2/2008 | Deng et al. |
| 7,332,310 B2 | 2/2008 | Nakagawa et al. |
| 7,332,316 B2 | 2/2008 | Schmulling et al. |
| 7,332,567 B2 | 2/2008 | Steward et al. |
| 7,335,361 B2 | 2/2008 | Liao et al. |
| 7,338,790 B2 | 3/2008 | Thierbach et al. |
| 7,338,799 B2 | 3/2008 | Blakely et al. |
| 7,339,037 B2 | 3/2008 | Boyd et al. |
| 7,344,710 B2 | 3/2008 | Dang et al. |
| 7,344,882 B2 | 3/2008 | Lee et al. |
| 7,345,148 B2 | 3/2008 | Feder et al. |
| 7,348,161 B2 | 3/2008 | Gay et al. |
| 7,351,568 B2 | 4/2008 | Dunn-Coleman et al. |
| 7,354,592 B2 | 4/2008 | Bermudes et al. |
| 7,357,934 B2 | 4/2008 | Donovan et al. |
| 7,358,074 B2 | 4/2008 | Jackson et al. |
| 7,358,084 B2 | 4/2008 | Kolkman |
| 7,364,787 B2 | 4/2008 | Ito et al. |
| 7,365,159 B2 | 4/2008 | O'Reilly et al. |
| 7,368,108 B2 | 5/2008 | DeFrees et al. |
| 7,368,284 B2 | 5/2008 | Koike |
| 7,371,559 B2 | 5/2008 | Boone et al. |
| 7,371,723 B2 | 5/2008 | Rosenblum et al. |
| 7,371,838 B2 | 5/2008 | Gilbert et al. |
| 7,374,896 B2 | 5/2008 | Steward et al. |
| 7,378,258 B2 | 5/2008 | Doucette-Stamm et al. |
| 7,378,514 B2 | 5/2008 | Doucette-Stamm et al. |
| 7,381,544 B2 | 6/2008 | Gilbert et al. |
| 7,390,633 B2 | 6/2008 | Liu et al. |
| 7,390,646 B2 | 6/2008 | Andino-Pavlovsky et al. |
| 7,393,525 B2 | 7/2008 | Powell et al. |
| 7,393,675 B2 | 7/2008 | Pompejus et al. |
| 7,396,824 B2 | 7/2008 | Sasisekharan et al. |
| 7,399,607 B2 | 7/2008 | Williams et al. |
| 7,404,963 B2 | 7/2008 | Sotomayor et al. |
| 7,405,081 B2 | 7/2008 | Pan |
| 7,405,235 B2 | 7/2008 | Levy et al. |
| 7,407,787 B2 | 8/2008 | Barrangou et al. |
| 7,410,791 B2 | 8/2008 | Singhvi et al. |
| 7,413,877 B2 | 8/2008 | Collier et al. |
| 7,414,119 B2 | 8/2008 | Greenberg et al. |
| 7,416,863 B2 | 8/2008 | Moeckel et al. |
| 7,420,030 B2 | 9/2008 | Arap et al. |
| 7,429,474 B2 | 9/2008 | Sasisekharan et al. |
| 7,432,085 B2 | 10/2008 | Hara et al. |
| 7,432,357 B2 | 10/2008 | Gillies |
| 7,435,808 B2 | 10/2008 | Wu et al. |
| 7,439,059 B2 | 10/2008 | Black, Jr. |
| 7,442,523 B2 | 10/2008 | Doucette-Stamm et al. |
| 7,452,531 B2 | 11/2008 | Bermudes et al. |
| 7,452,543 B2 | 11/2008 | Chaddock et al. |
| 7,459,309 B2 | 12/2008 | Dreyfuss et al. |
| 7,459,538 B2 | 12/2008 | Gillies et al. |
| 7,462,350 B2 | 12/2008 | Gillies et al. |
| 7,462,482 B2 | 12/2008 | Malik et al. |
| 7,465,447 B2 | 12/2008 | Gillies et al. |
| 7,470,667 B2 | 12/2008 | Luo et al. |
| 7,485,439 B2 | 2/2009 | Folkman et al. |
| 7,491,529 B2 | 2/2009 | Goddard et al. |
| 7,491,799 B2 | 2/2009 | Steward et al. |
| 7,494,798 B2 | 2/2009 | Berka et al. |
| 7,494,801 B2 | 2/2009 | Yazaki et al. |
| 7,495,069 B2 | 2/2009 | Steward et al. |
| 7,504,242 B2 | 3/2009 | McCormack et al. |
| 7,504,247 B2 | 3/2009 | Sasisekharan et al. |
| 7,507,406 B2 | 3/2009 | Gillies et al. |
| 7,510,859 B2 | 3/2009 | Wieland et al. |
| 7,514,089 B2 | 4/2009 | Bermudes et al. |
| 7,514,538 B2 | 4/2009 | Goddard et al. |
| 7,517,526 B2 | 4/2009 | Gillies et al. |
| 7,517,667 B2 | 4/2009 | Murphy et al. |
| 7,524,657 B2 | 4/2009 | Bathe et al. |
| 7,544,486 B2 | 6/2009 | Ting et al. |
| 7,557,186 B2 | 7/2009 | Tuli |
| 7,563,602 B2 | 7/2009 | Thierbach et al. |
| 7,566,777 B2 | 7/2009 | Enright et al. |
| 7,569,226 B2 | 8/2009 | Weber et al. |
| 7,569,376 B2 | 8/2009 | Bayer et al. |
| 7,569,384 B2 | 8/2009 | Rosen et al. |
| 7,569,386 B2 | 8/2009 | DeAngelis |
| 7,569,547 B2 | 8/2009 | Lindberg et al. |
| 7,572,618 B2 | 8/2009 | Mintier et al. |
| 7,582,445 B2 | 9/2009 | Anan et al. |
| 7,585,650 B2 | 9/2009 | Bathe et al. |
| 7,588,767 B2 | 9/2009 | Szalay et al. |
| 7,588,771 B2 | 9/2009 | Szalay et al. |
| 7,589,179 B2 | 9/2009 | Gillies et al. |
| 7,595,054 B2 | 9/2009 | Liao et al. |
| 7,598,027 B2 | 10/2009 | Fernandez-Salas et al. |
| 7,598,058 B2 | 10/2009 | Debinski et al. |
| 7,598,067 B2 | 10/2009 | Beavo et al. |
| 7,601,341 B2 | 10/2009 | Rosenblum |
| 7,601,814 B2 | 10/2009 | Gillies et al. |
| 7,611,712 B2 | 11/2009 | Karp |
| 7,611,883 B2 | 11/2009 | Cranenburgh |
| 7,615,223 B2 | 11/2009 | Thorpe et al. |
| 7,618,635 B2 | 11/2009 | Chang et al. |
| 7,618,798 B2 | 11/2009 | Bathe et al. |
| 7,622,564 B2 | 11/2009 | Ge et al. |
| 7,626,000 B2 | 12/2009 | Doucette-Stamm et al. |
| 7,629,150 B2 | 12/2009 | Narimatsu et al. |
| 7,632,504 B2 | 12/2009 | Whitlow et al. |
| 7,632,655 B2 | 12/2009 | Williams et al. |
| 7,632,924 B2 | 12/2009 | Cho et al. |
| 7,635,574 B2 | 12/2009 | Williams et al. |
| 7,635,598 B2 | 12/2009 | Cook et al. |
| 7,635,682 B2 | 12/2009 | Denmeade et al. |
| 7,635,765 B2 | 12/2009 | Farnet et al. |
| 7,638,282 B2 | 12/2009 | Bakaletz et al. |
| 7,638,294 B2 | 12/2009 | Williams et al. |
| 7,638,299 B2 | 12/2009 | Cho et al. |
| 7,645,570 B2 | 1/2010 | Fernandez-Salas et al. |
| 7,645,577 B2 | 1/2010 | Adderson et al. |
| 7,655,770 B1 | 2/2010 | Cheikh et al. |
| 7,655,774 B2 | 2/2010 | Mullins et al. |
| 7,655,781 B2 | 2/2010 | Shemesh et al. |
| 7,658,933 B2 | 2/2010 | Foster et al. |
| 7,662,398 B2 | 2/2010 | Szalay et al. |
| 7,662,933 B2 | 2/2010 | Kinstler et al. |
| 7,666,419 B2 | 2/2010 | Olson et al. |
| 7,666,627 B2 | 2/2010 | Gal et al. |
| 7,667,018 B2 | 2/2010 | Jakobovits et al. |
| 7,670,595 B2 | 3/2010 | Gillies et al. |
| 7,670,835 B2 | 3/2010 | Smith |
| 7,674,601 B2 | 3/2010 | Williams et al. |
| 7,678,550 B1 | 3/2010 | Steward et al. |
| 7,687,474 B2 | 3/2010 | Matin et al. |
| 7,691,383 B2 | 4/2010 | Chakrabarty et al. |
| 7,691,599 B2 | 4/2010 | Rubin |
| 7,691,983 B2 | 4/2010 | Fernandez-Salas et al. |
| 7,693,664 B2 | 4/2010 | Takami et al. |
| 7,695,711 B2 | 4/2010 | Myette et al. |
| 7,696,173 B2 | 4/2010 | Collier et al. |
| 7,700,104 B2 | 4/2010 | Hensel et al. |
| 7,700,313 B2 | 4/2010 | Schischka et al. |
| 7,700,317 B2 | 4/2010 | Ambrose et al. |
| 7,700,349 B2 | 4/2010 | Romaine et al. |
| 7,700,557 B2 | 4/2010 | Backer et al. |
| 7,700,830 B2 | 4/2010 | Corbin et al. |
| 7,704,506 B2 | 4/2010 | Fishman et al. |
| 7,705,195 B2 | 4/2010 | French et al. |
| 7,709,608 B2 | 5/2010 | Steward et al. |
| 7,718,180 B2 | 5/2010 | Karp |
| 7,718,363 B2 | 5/2010 | Brines et al. |
| 7,718,618 B2 | 5/2010 | Gallo et al. |
| 7,718,766 B2 | 5/2010 | Steward et al. |
| 7,722,867 B2 | 5/2010 | Umana et al. |
| 7,723,069 B2 | 5/2010 | Soll et al. |
| 7,723,472 B2 | 5/2010 | Szoka et al. |
| 7,727,538 B2 | 6/2010 | Quinn et al. |
| 7,727,741 B2 | 6/2010 | Umana et al. |
| 7,734,420 B2 | 6/2010 | Palsson et al. |
| 7,736,872 B2 | 6/2010 | Paulsel et al. |
| 7,736,898 B1 | 6/2010 | Fulton et al. |

(56)                References Cited

U.S. PATENT DOCUMENTS

| 7,740,835 | B2 | 6/2010 | Fujimori et al. |
| 7,740,853 | B2 | 6/2010 | Fishman et al. |
| 7,741,091 | B2 | 6/2010 | DeAngelis et al. |
| 7,741,278 | B2 | 6/2010 | Rosenblum et al. |
| 7,749,518 | B2 | 7/2010 | Masignani et al. |
| 7,749,746 | B2 | 7/2010 | Raitano et al. |
| 7,749,759 | B2 | 7/2010 | Fernandez-Salas et al. |
| 7,754,221 | B2 | 7/2010 | Szalay et al. |
| 7,754,420 | B2 | 7/2010 | Boyd |
| 7,754,446 | B2 | 7/2010 | Bathe et al. |
| 7,758,855 | B2 | 7/2010 | Kopecko et al. |
| 7,759,091 | B2 | 7/2010 | Rosenblum et al. |
| 7,763,250 | B2 | 7/2010 | Rosenthal et al. |
| 7,763,420 | B2 | 7/2010 | Stritzker et al. |
| 7,767,405 | B2 | 8/2010 | Gillies et al. |
| 7,767,643 | B2 | 8/2010 | Brines et al. |
| 7,771,981 | B2 | 8/2010 | DeAngelis |
| 7,776,323 | B2 | 8/2010 | Smith |
| 7,776,823 | B2 | 8/2010 | Gallo et al. |
| 7,785,779 | B2 | 8/2010 | Kroger et al. |
| 7,785,840 | B2 | 8/2010 | Bathe et al. |
| 7,785,861 | B2 | 8/2010 | Devroe et al. |
| 7,786,288 | B2 | 8/2010 | Karp |
| 7,790,177 | B2 | 9/2010 | Karp |
| 7,790,415 | B2 | 9/2010 | Gillies et al. |
| 7,790,860 | B2 | 9/2010 | Thorpe et al. |
| 7,803,531 | B2 | 9/2010 | Fulton et al. |
| 7,803,604 | B2 | 9/2010 | Breves et al. |
| 7,803,618 | B2 | 9/2010 | Gillies et al. |
| 7,803,769 | B2 | 9/2010 | Sullivan et al. |
| 7,803,918 | B2 | 9/2010 | van der Hoek |
| 7,803,923 | B2 | 9/2010 | Han et al. |
| 7,807,434 | B2 | 10/2010 | Dunn-Coleman et al. |
| 7,807,441 | B2 | 10/2010 | Steinaa et al. |
| 7,807,620 | B2 | 10/2010 | Lustbader |
| 7,811,799 | B2 | 10/2010 | Dunn-Coleman et al. |
| 7,816,086 | B2 | 10/2010 | Bakaletz et al. |
| 7,816,320 | B2 | 10/2010 | Hays et al. |
| 7,820,184 | B2 | 10/2010 | Stritzker et al. |
| 7,820,623 | B2 | 10/2010 | Sullivan et al. |
| 7,824,894 | B2 | 11/2010 | Barrangou et al. |
| 7,824,895 | B2 | 11/2010 | Short et al. |
| 7,825,093 | B2 | 11/2010 | Sullivan et al. |
| 7,829,310 | B2 | 11/2010 | Paulsel et al. |
| 7,833,979 | B2 | 11/2010 | Sullivan et al. |
| 7,834,164 | B2 | 11/2010 | Sullivan et al. |
| 7,834,166 | B2 | 11/2010 | Doucette-Stamm et al. |
| 7,838,260 | B2 | 11/2010 | Steward et al. |
| 7,838,265 | B2 | 11/2010 | Paulsel et al. |
| 7,842,290 | B2 | 11/2010 | Holden |
| 7,842,492 | B2 | 11/2010 | Myette et al. |
| 7,846,678 | B2 | 12/2010 | Pepe et al. |
| 7,846,689 | B2 | 12/2010 | Paulsel et al. |
| 7,846,706 | B2 | 12/2010 | Mintier et al. |
| 7,846,722 | B2 | 12/2010 | Williams et al. |
| 7,847,079 | B2 | 12/2010 | Rosen et al. |
| 7,850,970 | B2 | 12/2010 | Shapiro |
| 7,858,344 | B2 | 12/2010 | Paulsel et al. |
| 7,863,032 | B2 | 1/2011 | Berka et al. |
| 7,867,484 | B2 | 1/2011 | Samulski et al. |
| 7,867,732 | B2 | 1/2011 | Hori et al. |
| 7,869,957 | B2 | 1/2011 | Palsson et al. |
| 7,883,866 | B2 | 2/2011 | Paulsel et al. |
| 7,887,794 | B2 | 2/2011 | Luquet et al. |
| 7,887,810 | B2 | 2/2011 | Foster et al. |
| 7,887,816 | B2 | 2/2011 | Feldman et al. |
| 7,888,071 | B2 | 2/2011 | Gillies et al. |
| 7,888,321 | B2 | 2/2011 | Cooper et al. |
| 7,892,560 | B2 | 2/2011 | Foster et al. |
| 7,892,803 | B2 | 2/2011 | Tanner et al. |
| 7,892,825 | B2 | 2/2011 | Barr et al. |
| 7,893,007 | B2 | 2/2011 | Ladner et al. |
| 7,893,033 | B2 | 2/2011 | Hung et al. |
| 7,893,230 | B2 | 2/2011 | Doucette-Stamm et al. |
| 7,893,231 | B2 | 2/2011 | Bathe et al. |
| 7,893,238 | B2 | 2/2011 | Doucette-Stamm et al. |
| 7,901,691 | B2 | 3/2011 | Tuli et al. |
| 7,901,913 | B2 | 3/2011 | Dunican et al. |
| 7,906,628 | B2 | 3/2011 | Hung et al. |
| 7,910,102 | B2 | 3/2011 | Sullivan et al. |
| 7,910,715 | B2 | 3/2011 | Bathe et al. |
| 7,915,218 | B2 | 3/2011 | Capecchi et al. |
| 7,915,394 | B2 | 3/2011 | Schischka et al. |
| 7,919,311 | B2 | 4/2011 | Black, Jr. |
| 7,919,591 | B2 | 4/2011 | Sheffer et al. |
| 7,923,221 | B1 | 4/2011 | Cabilly et al. |
| 7,927,612 | B2 | 4/2011 | Yu |
| 7,939,319 | B2 | 5/2011 | Polack et al. |
| 7,939,496 | B2 | 5/2011 | Cho et al. |
| 7,943,571 | B2 | 5/2011 | Rosenblum et al. |
| 7,943,754 | B2 | 5/2011 | Bentwich et al. |
| 7,947,473 | B2 | 5/2011 | Buechler et al. |
| 7,947,822 | B2 | 5/2011 | Nabel et al. |
| 7,951,557 | B2 | 5/2011 | Shaaltiel et al. |
| 7,951,560 | B2 | 5/2011 | Myette et al. |
| 7,955,590 | B2 | 6/2011 | Gillies et al. |
| 7,955,600 | B2 | 6/2011 | Hensel et al. |
| 7,959,926 | B2 | 6/2011 | Buechler et al. |
| 7,960,514 | B2 | 6/2011 | Lauder et al. |
| 7,964,362 | B2 | 6/2011 | Lee et al. |
| 7,968,684 | B2 | 6/2011 | Ghayur et al. |
| 7,968,699 | B2 | 6/2011 | Haefner et al. |
| 7,973,150 | B2 | 7/2011 | Gillies et al. |
| 7,977,080 | B2 | 7/2011 | Gramatikova et al. |
| 7,977,084 | B2 | 7/2011 | Sun et al. |
| 7,981,659 | B2 | 7/2011 | Kadoya et al. |
| 7,989,202 | B1 | 8/2011 | Mach et al. |
| 7,993,905 | B2 | 8/2011 | Singhvi et al. |
| 7,998,461 | B2 | 8/2011 | Forbes et al. |
| 8,003,753 | B2 | 8/2011 | Steward et al. |
| 8,007,781 | B2 | 8/2011 | Wu et al. |
| 8,008,047 | B2 | 8/2011 | Iyo et al. |
| 8,008,283 | B2 | 8/2011 | Hochman et al. |
| 8,008,465 | B2 | 8/2011 | Fernandez-Salas et al. |
| 8,012,733 | B2 | 9/2011 | Van Dijk et al. |
| 8,012,931 | B2 | 9/2011 | Cujec et al. |
| 8,013,113 | B2 | 9/2011 | Steward et al. |
| 8,017,741 | B2 | 9/2011 | Fernandez-Salas et al. |
| 8,021,662 | B2 | 9/2011 | Szalay et al. |
| 8,021,859 | B2 | 9/2011 | Steward et al. |
| 8,022,172 | B2 | 9/2011 | Williams et al. |
| 8,022,186 | B2 | 9/2011 | Sheffer et al. |
| 8,026,386 | B2 | 9/2011 | Burk et al. |
| 8,029,789 | B2 | 10/2011 | Jung et al. |
| 8,030,023 | B2 | 10/2011 | Adams et al. |
| 8,030,447 | B2 | 10/2011 | Motin et al. |
| 8,030,542 | B2 | 10/2011 | Corbin et al. |
| 8,034,997 | B2 | 10/2011 | Bogdanova et al. |
| 8,043,608 | B2 | 10/2011 | Gillies et al. |
| 8,043,829 | B2 | 10/2011 | Sullivan et al. |
| 8,043,831 | B2 | 10/2011 | Rosenblum et al. |
| 8,043,839 | B2 | 10/2011 | Weiner et al. |
| 8,044,191 | B2 | 10/2011 | Kroger et al. |
| 8,048,643 | B2 | 11/2011 | Steward et al. |
| 8,048,646 | B2 | 11/2011 | Ting et al. |
| 8,048,651 | B2 | 11/2011 | Zelder et al. |
| 8,053,208 | B2 | 11/2011 | Steward et al. |
| 8,053,209 | B2 | 11/2011 | Steward et al. |
| 8,053,560 | B2 | 11/2011 | Sheffer et al. |
| 8,062,885 | B2 | 11/2011 | Mach et al. |
| 8,066,987 | B2 | 11/2011 | Moore et al. |
| 8,066,994 | B2 | 11/2011 | Gillies et al. |
| 8,067,179 | B2 | 11/2011 | Georgiou et al. |
| 8,067,231 | B2 | 11/2011 | Fernandez-Salas et al. |
| 8,067,377 | B2 | 11/2011 | Arap et al. |
| 8,067,530 | B2 | 11/2011 | O'Keefe et al. |
| 8,071,365 | B2 | 12/2011 | Kroger et al. |
| 8,080,391 | B2 | 12/2011 | Buechler et al. |
| 8,080,395 | B2 | 12/2011 | Bathe et al. |
| 8,088,620 | B2 | 1/2012 | Bestel-Corre et al. |
| 8,093,032 | B2 | 1/2012 | Kumar et al. |
| 8,093,037 | B2 | 1/2012 | Picataggio et al. |
| 8,093,356 | B2 | 1/2012 | Hays et al. |
| 8,097,436 | B2 | 1/2012 | Umana et al. |

(56) References Cited

U.S. PATENT DOCUMENTS

| | | | |
|---|---|---|---|
| 8,097,440 B1 | 1/2012 | Buelter et al. |
| 8,097,702 B2 | 1/2012 | Cho et al. |
| 8,101,168 B2 | 1/2012 | Hassan et al. |
| 8,101,349 B2 | 1/2012 | Garcia et al. |
| 8,101,396 B2 | 1/2012 | Sabbadini et al. |
| 8,101,826 B2 | 1/2012 | Romano |
| 8,105,602 B2 | 1/2012 | Parry et al. |
| 8,105,603 B2 | 1/2012 | Kelley et al. |
| 8,105,608 B2 | 1/2012 | Low et al. |
| 8,105,804 B2 | 1/2012 | Mintier et al. |
| 8,114,630 B2 | 2/2012 | Kraynov et al. |
| 8,114,974 B2 | 2/2012 | Picataggio et al. |
| 8,119,354 B2 | 2/2012 | Katanaev |
| 8,119,372 B2 | 2/2012 | Bathe et al. |
| 8,119,377 B2 | 2/2012 | Yi et al. |
| 8,119,603 B2 | 2/2012 | Cho et al. |
| 8,124,098 B2 | 2/2012 | Masignani et al. |
| 8,124,357 B2 | 2/2012 | Fernandez-Salas et al. |
| 8,124,381 B2 | 2/2012 | Deng et al. |
| 8,124,729 B2 | 2/2012 | Feder et al. |
| 8,128,922 B2 | 3/2012 | Wu et al. |
| 8,128,940 B2 | 3/2012 | Steward et al. |
| 8,129,166 B2 | 3/2012 | Sabbadini et al. |
| 8,133,493 B2 | 3/2012 | Curtiss, III |
| 8,137,904 B2 | 3/2012 | Szalay et al. |
| 8,137,928 B2 | 3/2012 | Schwartz et al. |
| 8,138,311 B2 | 3/2012 | Rosenblum et al. |
| 8,143,216 B2 | 3/2012 | Cho et al. |
| 8,153,404 B2 | 4/2012 | Bathe et al. |
| 8,153,414 B2 | 4/2012 | Caplan et al. |
| 8,158,132 B2 | 4/2012 | Foster et al. |
| 8,163,532 B2 | 4/2012 | Zelder et al. |
| 8,163,695 B2 | 4/2012 | Hays et al. |
| 8,168,417 B2 | 5/2012 | Berka et al. |
| 8,173,397 B2 | 5/2012 | Gal et al. |
| 8,178,108 B2 | 5/2012 | Buechler et al. |
| 8,178,319 B2 | 5/2012 | Pahlsson et al. |
| 8,178,339 B2 | 5/2012 | Campbell et al. |
| 8,178,494 B2 | 5/2012 | Hays et al. |
| 8,183,354 B2 | 5/2012 | DeVico et al. |
| 8,187,834 B2 | 5/2012 | Foster et al. |
| 8,198,045 B2 | 6/2012 | DeFrees et al. |
| 8,198,430 B2 | 6/2012 | Prior et al. |
| 8,202,706 B2 | 6/2012 | Bathe et al. |
| 8,206,700 B2 | 6/2012 | Horwitz et al. |
| 8,221,769 B2 | 7/2012 | Szalay et al. |
| 8,227,217 B2 | 7/2012 | Liu et al. |
| 8,227,230 B2 | 7/2012 | Shaaltiel et al. |
| 8,227,236 B2 | 7/2012 | Picataggio et al. |
| 8,231,878 B2 | 7/2012 | Colonna et al. |
| 8,232,371 B2 | 7/2012 | Cho et al. |
| 8,236,315 B2 | 8/2012 | Lazarides et al. |
| 8,236,494 B2 | 8/2012 | Bakaletz et al. |
| 8,236,531 B2 | 8/2012 | Asahara et al. |
| 8,241,623 B1 | 8/2012 | Bermudes |
| 8,244,484 B2 | 8/2012 | Lee et al. |
| 8,246,945 B2 | 8/2012 | Caplan et al. |
| 8,247,225 B2 | 8/2012 | Kopecko et al. |
| 8,252,579 B2 | 8/2012 | Meynial-Salles et al. |
| 8,257,914 B2 | 9/2012 | Fernandez-Salas et al. |
| 8,257,949 B2 | 9/2012 | Wakarchuk et al. |
| 8,258,100 B2 | 9/2012 | Enright et al. |
| 8,258,262 B2 | 9/2012 | Kinstler et al. |
| 8,278,065 B2 | 10/2012 | Nicolaides et al. |
| 8,278,418 B2 | 10/2012 | Tian et al. |
| 8,282,919 B2 | 10/2012 | Eisenstark et al. |
| 8,283,114 B2 | 10/2012 | Bakaletz et al. |
| 8,283,152 B2 | 10/2012 | Kim et al. |
| 8,283,319 B2 | 10/2012 | Schulte et al. |
| 8,283,456 B2 | 10/2012 | Gin et al. |
| 8,293,503 B2 | 10/2012 | Slater et al. |
| 8,293,514 B2 | 10/2012 | Bathe et al. |
| 8,298,791 B2 | 10/2012 | Matsuno et al. |
| 8,298,807 B2 | 10/2012 | Soucaille et al. |
| 8,304,604 B2 | 11/2012 | Lira et al. |
| 8,304,605 B2 | 11/2012 | Lira et al. |
| 8,323,959 B2 | 12/2012 | Szalay et al. |
| 8,323,961 B2 | 12/2012 | Nabel et al. |
| 8,324,362 B2 | 12/2012 | Chen et al. |
| 8,329,886 B2 | 12/2012 | Bardroff et al. |
| 8,338,575 B2 | 12/2012 | Lauder et al. |
| 8,343,509 B2 | 1/2013 | Stritzker et al. |
| 8,343,752 B2 | 1/2013 | Picataggio et al. |
| 8,344,207 B2 | 1/2013 | Bogdanova et al. |
| 8,349,570 B2 | 1/2013 | Pepe et al. |
| 8,354,264 B2 | 1/2013 | Mintier et al. |
| 8,357,486 B2 | 1/2013 | Stritzker et al. |
| 8,362,207 B2 | 1/2013 | Debinski et al. |
| 8,367,403 B2 | 2/2013 | Slater et al. |
| 8,367,621 B2 | 2/2013 | Ruoslahti et al. |
| 8,372,601 B2 | 2/2013 | Metcalf et al. |
| 8,372,620 B2 | 2/2013 | Sibbesen et al. |
| 8,372,625 B2 | 2/2013 | Walsh et al. |
| 8,383,365 B2 | 2/2013 | Cujec et al. |
| 8,383,388 B2 | 2/2013 | Oyhenart et al. |
| 8,394,607 B2 | 3/2013 | Ebens, Jr. et al. |
| 8,394,610 B2 | 3/2013 | Gulevich et al. |
| 8,404,226 B2 | 3/2013 | Brines et al. |
| 8,409,563 B2 | 4/2013 | Asahara et al. |
| 8,409,825 B2 | 4/2013 | Chiba et al. |
| 8,415,118 B2 | 4/2013 | Huang et al. |
| 8,420,350 B2 | 4/2013 | Nakamura et al. |
| 8,420,779 B2 | 4/2013 | Walker et al. |
| 8,420,792 B2 | 4/2013 | Tian et al. |
| 8,426,187 B2 | 4/2013 | Georgiou et al. |
| 8,426,571 B2 | 4/2013 | Raitano et al. |
| 8,431,373 B2 | 4/2013 | Yi et al. |
| 8,435,506 B2 | 5/2013 | Hassan et al. |
| 8,436,031 B2 | 5/2013 | Kim |
| 8,440,207 B2 | 5/2013 | Bermudes |
| 8,445,227 B2 | 5/2013 | Bobrowicz et al. |
| 8,445,241 B2 | 5/2013 | Dunican et al. |
| 8,445,254 B2 | 5/2013 | Curtiss, III et al. |
| 8,445,650 B2 | 5/2013 | Simpson et al. |
| 8,449,876 B2 | 5/2013 | Shaaltiel et al. |
| 8,455,683 B2 | 6/2013 | Burk et al. |
| 8,461,422 B2 | 6/2013 | Lira et al. |
| 8,465,755 B2 | 6/2013 | Curtiss, III et al. |
| 8,470,991 B2 | 6/2013 | Gillies et al. |
| 8,475,807 B2 | 7/2013 | Perez |
| 8,492,109 B2 | 7/2013 | Oyler et al. |
| 8,497,081 B2 | 7/2013 | Fernandez-Salas et al. |
| 8,501,190 B2 | 8/2013 | Prescott et al. |
| 8,506,947 B2 | 8/2013 | McCart et al. |
| 8,507,227 B2 | 8/2013 | Samain |
| 8,507,235 B2 | 8/2013 | Chotani et al. |
| 8,507,249 B2 | 8/2013 | Finlay et al. |
| 8,507,250 B2 | 8/2013 | Liu et al. |
| 8,512,984 B2 | 8/2013 | Foster et al. |
| 8,513,396 B2 | 8/2013 | Boone et al. |
| 8,513,493 B2 | 8/2013 | Baum et al. |
| 8,518,417 B1 | 8/2013 | Steward et al. |
| 8,524,220 B1 | 9/2013 | Bermudes |
| 8,524,241 B2 | 9/2013 | Seed et al. |
| 8,524,484 B2 | 9/2013 | Sabbadini et al. |
| 8,530,225 B2 | 9/2013 | Rosenblum et al. |
| 8,535,909 B2 | 9/2013 | Woldike et al. |
| 8,535,941 B2 | 9/2013 | Fernandez-Salas et al. |
| 8,540,992 B2 | 9/2013 | Naso et al. |
| 8,541,201 B2 | 9/2013 | Min et al. |
| 8,551,471 B2 | 10/2013 | Filutowicz et al. |
| 8,557,232 B2 | 10/2013 | Gillies et al. |
| 8,568,707 B2 | 10/2013 | Szalay et al. |
| 8,569,016 B2 | 10/2013 | Obayashi et al. |
| 8,575,316 B2 | 11/2013 | Hiruma et al. |
| 8,586,022 B2 | 11/2013 | Szalay et al. |
| 8,586,332 B2 | 11/2013 | Samain et al. |
| 8,591,862 B2 | 11/2013 | Brahmbhatt et al. |
| 8,592,187 B2 | 11/2013 | Bathe et al. |
| 8,603,779 B2 | 12/2013 | Foster et al. |
| 8,603,824 B2 | 12/2013 | Ramseier et al. |
| 8,604,004 B2 | 12/2013 | Kahne et al. |
| 8,604,178 B2 | 12/2013 | Bottje et al. |
| 8,606,553 B2 | 12/2013 | Palsson |

(56)                  References Cited

U.S. PATENT DOCUMENTS

| | | | |
|---|---|---|---|
| 8,609,358 | B2 | 12/2013 | Sebastian et al. |
| 8,623,350 | B1 | 1/2014 | Bermudes |
| 8,623,622 | B2 | 1/2014 | Srienc et al. |
| 8,623,999 | B2 | 1/2014 | Steward et al. |
| 8,628,782 | B2 | 1/2014 | Berkower |
| 8,628,917 | B2 | 1/2014 | Bakaletz et al. |
| 8,629,246 | B2 | 1/2014 | Humphreys et al. |
| 8,632,995 | B2 | 1/2014 | Sun et al. |
| 8,633,305 | B2 | 1/2014 | Shapiro |
| 8,635,031 | B2 | 1/2014 | Palsson |
| 8,637,295 | B1 | 1/2014 | Claes et al. |
| 8,642,257 | B2 | 2/2014 | Szalay et al. |
| 8,642,292 | B2 | 2/2014 | Sandig et al. |
| 8,647,642 | B2 | 2/2014 | Bermudes |
| 8,652,773 | B2 | 2/2014 | Bakaletz et al. |
| 8,652,808 | B2 | 2/2014 | Jennewein et al. |
| 8,652,838 | B2 | 2/2014 | Shen et al. |
| 8,663,634 | B2 | 3/2014 | Koenig et al. |
| 8,663,962 | B2 | 3/2014 | Zhang et al. |
| 8,673,601 | B2 | 3/2014 | Burgard et al. |
| 8,674,062 | B2 | 3/2014 | Dunn-Coleman et al. |
| 8,674,083 | B2 | 3/2014 | Presta |
| 8,680,236 | B2 | 3/2014 | Luft et al. |
| 8,685,392 | B2 | 4/2014 | Helmerhorst et al. |
| 8,685,718 | B2 | 4/2014 | Wisniewski et al. |
| 8,685,939 | B2 | 4/2014 | Wei et al. |
| 8,686,218 | B2 | 4/2014 | Romaine et al. |
| 8,691,952 | B2 | 4/2014 | Super et al. |
| 8,697,398 | B2 | 4/2014 | Doherty et al. |
| 8,697,414 | B2 | 4/2014 | Steward et al. |
| 8,697,642 | B2 | 4/2014 | Lira et al. |
| 8,703,153 | B2 | 4/2014 | Telfer et al. |
| 8,703,471 | B2 | 4/2014 | Aebi et al. |
| 8,709,813 | B2 | 4/2014 | Kopecko et al. |
| 8,715,641 | B2 | 5/2014 | Filutowicz et al. |
| 8,716,450 | B2 | 5/2014 | Ghayur et al. |
| 8,722,584 | B2 | 5/2014 | Delisa et al. |
| 8,722,618 | B2 | 5/2014 | Jacobs et al. |
| 8,722,668 | B2 | 5/2014 | Hochman |
| 8,722,855 | B2 | 5/2014 | Ghayur et al. |
| 8,722,869 | B2 | 5/2014 | Fang et al. |
| 8,728,795 | B2 | 5/2014 | Kroger et al. |
| 8,728,798 | B2 | 5/2014 | Picataggio et al. |
| 8,734,779 | B2 | 5/2014 | Hamaji et al. |
| 8,734,814 | B2 | 5/2014 | Datta et al. |
| 8,735,159 | B2 | 5/2014 | Zelder et al. |
| 8,735,539 | B2 | 5/2014 | Kraynov et al. |
| 8,735,546 | B2 | 5/2014 | Ghayur et al. |
| 8,735,560 | B1 | 5/2014 | English et al. |
| 8,741,313 | B2 | 6/2014 | Sable et al. |
| 8,741,608 | B2 | 6/2014 | Claes et al. |
| 8,741,620 | B2 | 6/2014 | Shaaltiel et al. |
| 8,741,623 | B2 | 6/2014 | Zelder et al. |
| 8,748,373 | B2 | 6/2014 | Chai et al. |
| 8,753,604 | B2 | 6/2014 | Ruoslahti et al. |
| 8,758,741 | B2 | 6/2014 | Takagi et al. |
| 8,758,764 | B2 | 6/2014 | Masignani et al. |
| 8,758,771 | B2 | 6/2014 | Finlay et al. |
| 8,759,086 | B2 | 6/2014 | Mach et al. |
| 8,759,494 | B2 | 6/2014 | Bachmann et al. |
| 8,765,407 | B2 | 7/2014 | Iyo et al. |
| 8,771,669 | B1 | 7/2014 | Bermudes |
| 8,771,671 | B2 | 7/2014 | Spencer et al. |
| 8,771,707 | B2 | 7/2014 | Chapman et al. |
| 8,771,708 | B2 | 7/2014 | Evans et al. |
| 8,771,991 | B2 | 7/2014 | Gilbert et al. |
| 8,778,634 | B2 | 7/2014 | Foster et al. |
| 8,778,652 | B2 | 7/2014 | Subbian et al. |
| 8,778,880 | B2 | 7/2014 | Cho et al. |
| 8,784,836 | B2 | 7/2014 | Szalay et al. |
| 8,790,641 | B2 | 7/2014 | Shaaltiel et al. |
| 8,791,237 | B2 | 7/2014 | Paterson et al. |
| 8,795,730 | B2 | 8/2014 | Vachon |
| 8,809,027 | B1 | 8/2014 | Lynch et al. |
| 8,815,251 | B2 | 8/2014 | Caplan et al. |
| 8,815,558 | B2 | 8/2014 | Frost et al. |
| RE45,170 | E | 9/2014 | Smith |
| 8,821,893 | B2 | 9/2014 | Dattwyler et al. |
| 8,822,194 | B2 | 9/2014 | Zhao et al. |
| 8,822,645 | B2 | 9/2014 | Ghayur et al. |
| 8,822,664 | B2 | 9/2014 | Cicortas Gunnarsson et al. |
| 8,828,681 | B2 | 9/2014 | Bell, III et al. |
| 8,835,107 | B2 | 9/2014 | Van Der Hoek |
| 8,835,162 | B2 | 9/2014 | Kwon et al. |
| 8,835,606 | B2 | 9/2014 | Gillies |
| 8,841,253 | B2 | 9/2014 | Murphy et al. |
| 8,846,363 | B2 | 9/2014 | Myette et al. |
| 8,852,603 | B2 | 10/2014 | Foster et al. |
| 8,852,890 | B2 | 10/2014 | Cervin et al. |
| 8,852,927 | B2 | 10/2014 | Szalay et al. |
| 8,853,154 | B2 | 10/2014 | Cload et al. |
| 8,853,362 | B2 | 10/2014 | Tissot et al. |
| 8,865,153 | B2 | 10/2014 | Szalay et al. |
| 8,865,442 | B2 | 10/2014 | Chotani et al. |
| 8,871,491 | B2 | 10/2014 | Wacker et al. |
| 8,871,906 | B2 | 10/2014 | Pastan et al. |
| 8,883,464 | B2 | 11/2014 | Lynch et al. |
| 8,889,121 | B2 | 11/2014 | Curtiss, III et al. |
| 8,889,383 | B2 | 11/2014 | Beck et al. |
| 8,889,842 | B2 | 11/2014 | Gin et al. |
| 8,895,277 | B2 | 11/2014 | Beatty et al. |
| 8,906,653 | B2 | 12/2014 | Volkert et al. |
| 8,906,662 | B2 | 12/2014 | Nataro et al. |
| 8,906,676 | B2 | 12/2014 | Cho et al. |
| 8,907,064 | B2 | 12/2014 | Cho et al. |
| 8,907,066 | B2 | 12/2014 | Lo et al. |
| 8,907,071 | B2 | 12/2014 | Sullivan et al. |
| 8,912,313 | B2 | 12/2014 | Reth et al. |
| 8,920,798 | B2 | 12/2014 | Han et al. |
| 8,920,809 | B2 | 12/2014 | Dirienzo |
| 8,926,973 | B2 | 1/2015 | Gillies et al. |
| 8,926,993 | B2 | 1/2015 | Dubensky, Jr. et al. |
| 8,932,598 | B2 | 1/2015 | Song et al. |
| 8,946,148 | B2 | 2/2015 | Miao et al. |
| 8,951,759 | B2 | 2/2015 | Claes et al. |
| 8,951,992 | B2 | 2/2015 | Nathan et al. |
| 8,956,849 | B2 | 2/2015 | Bottje et al. |
| 8,956,859 | B1 | 2/2015 | Bermudes |
| 8,957,195 | B2 | 2/2015 | Super et al. |
| 8,961,990 | B2 | 2/2015 | Hargis et al. |
| 8,962,275 | B2 | 2/2015 | Liang et al. |
| 8,962,816 | B2 | 2/2015 | Ertl et al. |
| 8,969,529 | B2 | 3/2015 | O'Brien et al. |
| 8,969,538 | B2 | 3/2015 | Rosen et al. |
| 8,969,542 | B2 | 3/2015 | Buyse et al. |
| 8,975,040 | B2 | 3/2015 | Naso et al. |
| 8,975,051 | B2 | 3/2015 | McAuliffe et al. |
| 8,981,061 | B2 | 3/2015 | Colonna et al. |
| 8,993,265 | B2 | 3/2015 | Cload et al. |
| 8,993,295 | B2 | 3/2015 | Seed et al. |
| 8,993,297 | B2 | 3/2015 | Ronin et al. |
| 8,993,305 | B2 | 3/2015 | Beck et al. |
| 8,999,949 | B2 | 4/2015 | Spencer et al. |
| 9,000,036 | B2 | 4/2015 | Yu |
| 9,005,600 | B2 | 4/2015 | Debinski et al. |
| 9,005,949 | B2 | 4/2015 | Oxvig et al. |
| 9,006,520 | B2 | 4/2015 | Lira et al. |
| 9,011,866 | B2 | 4/2015 | Wu et al. |
| 9,012,152 | B2 | 4/2015 | Engelberg-Kulka et al. |
| 9,012,186 | B2 | 4/2015 | Cann et al. |
| 9,012,195 | B2 | 4/2015 | Foster et al. |
| 9,012,226 | B2 | 4/2015 | Williams |
| 9,017,966 | B2 | 4/2015 | Williams et al. |
| 9,017,986 | B2 | 4/2015 | Sabbadini et al. |
| 9,018,014 | B2 | 4/2015 | Slater et al. |
| 9,023,635 | B2 | 5/2015 | Bayer et al. |
| 9,029,104 | B2 | 5/2015 | Samsonova et al. |
| 9,029,136 | B2 | 5/2015 | Heidtman et al. |
| 9,029,508 | B2 | 5/2015 | Ghayur et al. |
| 9,034,642 | B2 | 5/2015 | Bakaletz et al. |
| 9,037,445 | B2 | 5/2015 | Oltvai et al. |
| 9,040,059 | B2 | 5/2015 | Curtiss, III et al. |
| 9,045,742 | B2 | 6/2015 | Curtiss, III et al. |
| 9,045,745 | B2 | 6/2015 | Subbian et al. |

(56)                    References Cited

U.S. PATENT DOCUMENTS

| | | | |
|---|---|---|---|
| 9,045,762 | B2 | 6/2015 | Reth et al. |
| 9,045,766 | B2 | 6/2015 | Meade et al. |
| 9,050,285 | B2 | 6/2015 | Curtiss, III et al. |
| 9,051,565 | B2 | 6/2015 | Delisa et al. |
| 9,051,588 | B2 | 6/2015 | Soucaille et al. |
| 9,062,297 | B2 | 6/2015 | Curtiss, III et al. |
| 9,068,187 | B1 | 6/2015 | Bermudes |
| 9,072,736 | B2 | 7/2015 | Foster et al. |
| 9,074,229 | B2 | 7/2015 | Reth et al. |
| 9,079,971 | B2 | 7/2015 | Cujec et al. |
| 9,085,638 | B2 | 7/2015 | Wu et al. |
| 9,085,765 | B2 | 7/2015 | Campbell et al. |
| 9,090,889 | B2 | 7/2015 | Nunn, Jr. et al. |
| 9,090,928 | B2 | 7/2015 | Park et al. |
| 9,096,651 | B2 | 8/2015 | Igawa et al. |
| 9,102,729 | B2 | 8/2015 | Masignani et al. |
| 9,102,958 | B2 | 8/2015 | Botes et al. |
| 9,102,960 | B2 | 8/2015 | Botes et al. |
| 9,109,229 | B2 | 8/2015 | Ramseier et al. |
| 9,121,024 | B2 | 9/2015 | Tian et al. |
| 9,121,025 | B2 | 9/2015 | Tian et al. |
| 9,121,038 | B2 | 9/2015 | Beck et al. |
| 9,125,854 | B2 | 9/2015 | Bottje et al. |
| 9,125,855 | B2 | 9/2015 | Pasmans et al. |
| 9,139,635 | B2 | 9/2015 | Foster et al. |
| 9,139,844 | B2 | 9/2015 | Meade et al. |
| 9,150,827 | B2 | 10/2015 | Wendisch et al. |
| 9,150,868 | B2 | 10/2015 | Tokuda et al. |
| 9,150,885 | B2 | 10/2015 | Shibamoto |
| 9,155,798 | B2 | 10/2015 | Vallera |
| 9,156,899 | B2 | 10/2015 | Tian et al. |
| 9,161,974 | B2 | 10/2015 | Dubensky et al. |
| 9,163,219 | B2 | 10/2015 | Curtiss, III et al. |
| 9,163,263 | B2 | 10/2015 | Beck et al. |
| 9,169,468 | B2 | 10/2015 | Zhang et al. |
| 9,169,502 | B2 | 10/2015 | Wittmann et al. |
| 9,175,083 | B2 | 11/2015 | Cho et al. |
| 9,187,523 | B2 | 11/2015 | Motin et al. |
| 9,187,762 | B2 | 11/2015 | Albert et al. |
| 9,198,960 | B2 | 12/2015 | Dubensky, Jr. et al. |
| 9,200,251 | B1 | 12/2015 | Bermudes |
| 9,200,289 | B1 | 12/2015 | Bermudes |
| 9,206,456 | B2 | 12/2015 | Lenormand |
| 9,221,877 | B2 | 12/2015 | Hansel et al. |
| 9,226,957 | B2 | 1/2016 | Bottje et al. |
| 9,228,017 | B2 | 1/2016 | Igawa et al. |
| 9,233,137 | B2 | 1/2016 | de Muinck et al. |
| 9,234,208 | B1 | 1/2016 | Lira et al. |
| 9,243,301 | B2 | 1/2016 | Foster et al. |
| 9,248,177 | B2 | 2/2016 | Tang et al. |
| 9,249,430 | B2 | 2/2016 | Marliere |
| 9,260,472 | B2 | 2/2016 | Cho et al. |
| 9,260,729 | B2 | 2/2016 | Sun et al. |
| 9,267,156 | B2 | 2/2016 | Amano et al. |
| 9,284,573 | B2 | 3/2016 | Meade et al. |
| 9,297,015 | B2 | 3/2016 | Curtiss, III et al. |
| 9,303,264 | B2 | 4/2016 | Curtiss et al. |
| 9,309,327 | B2 | 4/2016 | Humphreys et al. |
| 9,315,817 | B2 | 4/2016 | Bermudes |
| 9,315,831 | B2 | 4/2016 | Blake et al. |
| 9,321,847 | B2 | 4/2016 | Benhar et al. |
| 9,328,148 | B2 | 5/2016 | Joens et al. |
| 9,334,313 | B2 | 5/2016 | Masignani et al. |
| 9,334,508 | B2 | 5/2016 | Pearlman et al. |
| 9,340,615 | B2 | 5/2016 | Maeda et al. |
| 9,340,793 | B2 | 5/2016 | Muramatsu et al. |
| 9,365,625 | B1 | 6/2016 | Bermudes |
| 9,365,874 | B2 | 6/2016 | Burk et al. |
| 9,371,531 | B2 | 6/2016 | Slater et al. |
| 9,388,394 | B2 | 7/2016 | Heinrichs et al. |
| 9,388,397 | B2 | 7/2016 | Rosenblum et al. |
| 9,388,417 | B2 | 7/2016 | Lee et al. |
| 9,388,419 | B2 | 7/2016 | Lynch et al. |
| 9,388,431 | B2 | 7/2016 | McAuliffe et al. |
| 9,399,058 | B2 | 7/2016 | Prescott et al. |
| 9,421,252 | B2 | 8/2016 | Bermudes |
| 9,422,578 | B2 | 8/2016 | Pearlman et al. |
| 9,422,580 | B2 | 8/2016 | Pearlman et al. |
| 9,428,778 | B2 | 8/2016 | Lynch et al. |
| 9,434,778 | B2 | 9/2016 | Morin et al. |
| 9,434,966 | B2 | 9/2016 | Picataggio et al. |
| 9,441,251 | B2 | 9/2016 | Lee et al. |
| 9,447,405 | B2 | 9/2016 | Johnson et al. |
| 9,449,144 | B2 | 9/2016 | Oltvai et al. |
| 9,452,205 | B2 | 9/2016 | Pascual et al. |
| 9,452,222 | B2 | 9/2016 | Kraynov et al. |
| 9,464,129 | B2 | 10/2016 | Serraima et al. |
| 9,464,288 | B2 | 10/2016 | Soll et al. |
| 9,469,857 | B2 | 10/2016 | Slater et al. |
| 9,474,807 | B2 | 10/2016 | Foster et al. |
| 9,486,513 | B1 | 11/2016 | Bermudes |
| 9,487,798 | B2 | 11/2016 | Lira et al. |
| 9,488,660 | B2 | 11/2016 | Miao et al. |
| 9,492,534 | B2 | 11/2016 | Szalay et al. |
| 9,499,835 | B2 | 11/2016 | Meade et al. |
| 9,504,735 | B2 | 11/2016 | Sanders |
| 9,517,273 | B2 | 12/2016 | Cujec et al. |
| 9,567,386 | B2 | 2/2017 | Kraynov et al. |
| 9,567,594 | B2 | 2/2017 | Park et al. |
| 9,567,602 | B2 | 2/2017 | Meade et al. |
| 9,580,716 | B2 | 2/2017 | Park et al. |
| 9,593,339 | B1 | 3/2017 | Bermudes |
| 9,597,379 | B1 | 3/2017 | Bermudes |
| 9,598,685 | B2 | 3/2017 | Dong et al. |
| 9,616,114 | B1 | 4/2017 | Bermudes |
| 9,617,349 | B2 | 4/2017 | Gillies |
| 9,631,004 | B2 | 4/2017 | Morin et al. |
| 9,644,014 | B2 | 5/2017 | Tian et al. |
| 9,657,085 | B1 | 5/2017 | Bermudes |
| 9,663,795 | B2 | 5/2017 | Meade et al. |
| 9,670,269 | B2 | 6/2017 | Igawa et al. |
| 9,694,063 | B2 | 7/2017 | Scarselli et al. |
| 9,694,064 | B2 | 7/2017 | Boutriau et al. |
| 9,701,725 | B2 | 7/2017 | Wu et al. |
| 9,718,850 | B2 | 8/2017 | Gin et al. |
| 9,730,994 | B2 | 8/2017 | Pietrobon et al. |
| 9,737,592 | B1 | 8/2017 | Bermudes et al. |
| 9,739,773 | B1 | 8/2017 | Bermudes |
| 9,758,551 | B2 | 9/2017 | Wu et al. |
| 9,764,006 | B2 | 9/2017 | Wang et al. |
| 9,771,404 | B2 | 9/2017 | Debinski et al. |
| 9,796,982 | B2 | 10/2017 | Meade et al. |
| 9,801,931 | B2 | 10/2017 | O'Brien et al. |
| 9,828,429 | B2 | 11/2017 | Igawa et al. |
| 9,828,438 | B2 | 11/2017 | Humphreys et al. |
| 9,868,948 | B2 | 1/2018 | Igawa et al. |
| 9,878,023 | B1 | 1/2018 | Bermudes |
| 9,890,377 | B2 | 2/2018 | Igawa et al. |
| 9,937,260 | B2 | 4/2018 | Hansel et al. |
| 9,938,333 | B2 | 4/2018 | Kraynov et al. |
| 9,962,450 | B2 | 5/2018 | Kraynov et al. |
| 9,975,936 | B2 | 5/2018 | Cujec et al. |
| 10,011,858 | B2 | 7/2018 | Igawa et al. |
| 10,011,991 | B2 | 7/2018 | Thiagarajan et al. |
| 10,012,002 | B2 | 7/2018 | Velet et al. |
| 10,012,009 | B2 | 7/2018 | Jahnsen |
| 10,012,015 | B2 | 7/2018 | Rejc |
| 10,012,019 | B2 | 7/2018 | Veerasamy et al. |
| 10,017,579 | B2 | 7/2018 | Gillies |
| 10,022,001 | B1 | 7/2018 | Hawkins |
| 10,022,003 | B1 | 7/2018 | Edoria |
| 10,022,007 | B1 | 7/2018 | Lucero |
| 10,022,008 | B1 | 7/2018 | Staton et al. |
| 10,022,012 | B2 | 7/2018 | Etter et al. |
| 10,022,014 | B2 | 7/2018 | Mateos Martin et al. |
| 10,022,018 | B2 | 7/2018 | Egger et al. |
| 10,022,450 | B2 | 7/2018 | Johnson et al. |
| 10,023,893 | B2 | 7/2018 | Soll et al. |
| 10,028,510 | B2 | 7/2018 | Lira et al. |
| 10,031,995 | B2 | 7/2018 | Haller et al. |
| 10,032,002 | B2 | 7/2018 | Kiani et al. |
| 10,032,006 | B2 | 7/2018 | Meah |
| 10,032,019 | B2 | 7/2018 | Allison et al. |
| 10,042,005 | B2 | 8/2018 | Syouda et al. |

(56)  References Cited

U.S. PATENT DOCUMENTS

| | | | |
|---|---|---|---|
| 10,042,007 B2 | 8/2018 | Heber |
| 10,042,011 B2 | 8/2018 | Deng |
| 10,042,012 B2 | 8/2018 | Lee |
| 10,051,988 B2 | 8/2018 | Gordon et al. |
| 10,051,993 B2 | 8/2018 | Myllymaki |
| 10,051,999 B2 | 8/2018 | Coenraadts |
| 10,052,006 B1 | 8/2018 | Morad |
| 10,052,010 B2 | 8/2018 | Feddema |
| 10,061,992 B2 | 8/2018 | Gondo |
| 10,061,993 B2 | 8/2018 | Cui et al. |
| 10,062,005 B2 | 8/2018 | Eliazar |
| 10,062,009 B2 | 8/2018 | Lahr |
| 10,062,010 B2 | 8/2018 | Kutliroff |
| 10,062,011 B2 | 8/2018 | Cox et al. |
| 10,062,015 B2 | 8/2018 | Besehanic |
| 10,062,016 B2 | 8/2018 | Shirai |
| 10,066,018 B2 | 9/2018 | Igawa et al. |
| 10,071,997 B2 | 9/2018 | Muehlebach et al. |
| 10,072,003 B2 | 9/2018 | Arasappan et al. |
| 10,072,008 B2 | 9/2018 | Almansa-Rosales |
| 10,072,010 B2 | 9/2018 | Li et al. |
| 10,072,014 B2 | 9/2018 | Van Gool et al. |
| 10,072,092 B2 | 9/2018 | Super et al. |
| 10,081,991 B2 | 9/2018 | Amezaga et al. |
| 10,081,996 B2 | 9/2018 | Krieg et al. |
| 10,082,009 B2 | 9/2018 | Trautman et al. |
| 10,082,013 B2 | 9/2018 | Nguyen et al. |
| 10,082,015 B2 | 9/2018 | Williams et al. |
| 10,082,019 B2 | 9/2018 | Gao et al. |
| 10,087,451 B2 | 10/2018 | Bermudes |
| 10,092,007 B2 | 10/2018 | Pierce et al. |
| 10,092,008 B2 | 10/2018 | Frank et al. |
| 10,092,012 B2 | 10/2018 | Spivey et al. |
| 10,092,014 B2 | 10/2018 | Holland et al. |
| 10,100,130 B2 | 10/2018 | Humphreys et al. |
| 10,102,002 B2 | 10/2018 | Alexander et al. |
| 10,102,006 B2 | 10/2018 | Li et al. |
| 10,102,013 B2 | 10/2018 | Preston et al. |
| 10,111,994 B2 | 10/2018 | Wu et al. |
| 10,112,001 B2 | 10/2018 | Karoor |
| 10,112,005 B2 | 10/2018 | Rotem et al. |
| 10,112,007 B2 | 10/2018 | Reid |
| 10,112,011 B2 | 10/2018 | Peyser |
| 10,112,012 B2 | 10/2018 | Tu |
| 10,112,016 B2 | 10/2018 | Draper et al. |
| 10,112,018 B2 | 10/2018 | Cowe |
| 10,119,149 B2 | 11/2018 | Meade et al. |
| 10,121,999 B2 | 11/2018 | Kato et al. |
| 10,122,004 B2 | 11/2018 | De Souza et al. |
| 10,122,006 B2 | 11/2018 | Matsumura |
| 10,122,010 B2 | 11/2018 | Tajima et al. |
| 10,125,328 B2 | 11/2018 | Eizenga et al. |
| 10,130,694 B2 | 11/2018 | Boutriau et al. |
| 10,131,998 B2 | 11/2018 | Wiedeman |
| 10,132,005 B2 | 11/2018 | Soderberg et al. |
| 10,132,009 B2 | 11/2018 | Chou et al. |
| 10,132,011 B2 | 11/2018 | Malina et al. |
| 10,132,015 B2 | 11/2018 | Woodruff et al. |
| 10,138,283 B2 | 11/2018 | Hays Putnam et al. |
| 10,141,997 B2 | 11/2018 | Nabar et al. |
| 10,142,003 B2 | 11/2018 | Bi et al. |
| 10,142,004 B2 | 11/2018 | Park et al. |
| 10,142,008 B1 | 11/2018 | Fang et al. |
| 10,142,010 B2 | 11/2018 | Bennett et al. |
| 10,150,808 B2 | 12/2018 | Kuramochi et al. |
| 10,151,991 B2 | 12/2018 | Kojima et al. |
| 10,152,013 B2 | 12/2018 | Kusano et al. |
| 10,152,015 B2 | 12/2018 | Suzuki |
| 10,162,001 B2 | 12/2018 | Whetsel |
| 10,162,003 B2 | 12/2018 | Whetsel |
| 10,162,008 B2 | 12/2018 | Kinsella |
| 10,162,014 B2 | 12/2018 | Iida et al. |
| 10,162,018 B2 | 12/2018 | Matsui et al. |
| 10,171,995 B2 | 1/2019 | Raleigh et al. |
| 10,172,002 B2 | 1/2019 | He |
| 10,172,006 B2 | 1/2019 | Weigand et al. |
| 10,172,013 B2 | 1/2019 | Sun et al. |
| 10,181,994 B2 | 1/2019 | Stokking et al. |
| 10,182,001 B2 | 1/2019 | Bruckner et al. |
| 10,182,005 B2 | 1/2019 | Dixon et al. |
| 10,182,007 B2 | 1/2019 | Zhang |
| 10,182,012 B2 | 1/2019 | Minakuchi et al. |
| 10,182,016 B2 | 1/2019 | Birke et al. |
| 10,188,722 B2 | 1/2019 | Bermudes |
| 10,189,883 B2 | 1/2019 | Morin et al. |
| 10,190,110 B2 | 1/2019 | Dong et al. |
| 10,191,993 B2 | 1/2019 | Ross et al. |
| 10,192,006 B2 | 1/2019 | Kim et al. |
| 10,192,010 B1 | 1/2019 | Ross et al. |
| 10,192,017 B2 | 1/2019 | Bref et al. |
| 10,201,998 B2 | 2/2019 | Connolly |
| 10,202,005 B2 | 2/2019 | Shimizu et al. |
| 10,202,011 B2 | 2/2019 | MacNeil et al. |
| 10,202,015 B2 | 2/2019 | Halbauer |
| 10,211,999 B2 | 2/2019 | Pelton et al. |
| 10,212,003 B2 | 2/2019 | Traeber |
| 10,212,004 B2 | 2/2019 | Xue et al. |
| 10,212,008 B2 | 2/2019 | Palmer |
| 10,212,010 B2 | 2/2019 | Zhang et al. |
| 10,212,014 B2 | 2/2019 | Qu et al. |
| 10,221,996 B2 | 3/2019 | Sauer |
| 10,222,002 B2 | 3/2019 | Yao et al. |
| 10,222,009 B2 | 3/2019 | Woisetschlaeger et al. |
| 10,222,019 B1 | 3/2019 | Li et al. |
| 10,232,003 B2 | 3/2019 | Mulvey et al. |
| 10,232,007 B2 | 3/2019 | Konowalchuk et al. |
| 10,232,008 B1 | 3/2019 | Moran |
| 10,232,012 B2 | 3/2019 | Lim et al. |
| 10,233,224 B2 | 3/2019 | Debinski et al. |
| 10,240,158 B2 | 3/2019 | Soll et al. |
| 10,241,995 B2 | 3/2019 | Rangarajan Sridhar |
| 10,242,000 B2 | 3/2019 | Antonatos et al. |
| 10,242,002 B2 | 3/2019 | English et al. |
| 10,242,006 B2 | 3/2019 | Juang et al. |
| 10,242,013 B2 | 3/2019 | Eda et al. |
| 10,242,017 B2 | 3/2019 | Berthiaume et al. |
| 10,251,989 B2 | 4/2019 | Cook et al. |
| 10,252,011 B2 | 4/2019 | Garde et al. |
| 10,252,012 B2 | 4/2019 | Garde et al. |
| 10,252,016 B2 | 4/2019 | Pedro et al. |
| 10,253,083 B2 | 4/2019 | Kraynov et al. |
| 10,253,091 B2 | 4/2019 | Igawa et al. |
| 10,262,006 B2 | 4/2019 | Rawat et al. |
| 10,262,010 B2 | 4/2019 | Gadepalli et al. |
| 10,266,578 B2 | 4/2019 | Dubowchik et al. |
| 10,271,987 B2 | 4/2019 | Rajguru et al. |
| 10,271,998 B2 | 4/2019 | LaVon et al. |
| 10,272,005 B2 | 4/2019 | Heidingsfelder-Bongard et al. |
| 10,272,011 B1 | 4/2019 | Sloan |
| 10,272,015 B2 | 4/2019 | Bonderer et al. |
| 10,272,016 B2 | 4/2019 | Allyn et al. |
| 10,282,003 B2 | 5/2019 | Park |
| 10,282,004 B2 | 5/2019 | Xie et al. |
| 10,282,005 B2 | 5/2019 | Li et al. |
| 10,282,008 B2 | 5/2019 | Chung et al. |
| 10,282,010 B2 | 5/2019 | Choi et al. |
| 10,282,014 B2 | 5/2019 | Butler et al. |
| 10,286,051 B1 | 5/2019 | Bermudes |
| 10,291,996 B1 | 5/2019 | Shaffer et al. |
| 10,292,002 B2 | 5/2019 | Patel |
| 10,292,009 B2 | 5/2019 | Choi et al. |
| 10,292,013 B2 | 5/2019 | Frank et al. |
| 10,292,015 B1 | 5/2019 | Thiagarajan et al. |
| 10,302,001 B2 | 5/2019 | Jung et al. |
| 10,302,003 B2 | 5/2019 | Kuramashi et al. |
| 10,302,007 B2 | 5/2019 | Erdel |
| 10,302,008 B2 | 5/2019 | Clarke et al. |
| 10,302,012 B2 | 5/2019 | Yoshizaki et al. |
| 10,302,014 B2 | 5/2019 | Suciu et al. |
| 10,312,000 B2 | 6/2019 | Good |
| 10,312,002 B2 | 6/2019 | Kondo et al. |
| 10,312,006 B2 | 6/2019 | Yamamoto et al. |
| 10,312,013 B2 | 6/2019 | Kawasaki et al. |
| 10,312,017 B2 | 6/2019 | Huang et al. |

(56) References Cited

U.S. PATENT DOCUMENTS

| 10,364,435 B1 | 7/2019 | Bermudes |
| 10,377,805 B2 | 8/2019 | Cujec et al. |
| 10,377,806 B2 | 8/2019 | Morin et al. |
| 10,400,013 B2 | 9/2019 | Liao et al. |
| 10,407,513 B2 | 9/2019 | Adams et al. |
| 10,421,958 B2 | 9/2019 | Poma et al. |
| 10,428,333 B2 | 10/2019 | Tian et al. |
| 10,435,458 B2 | 10/2019 | Kuramochi et al. |
| 10,449,237 B1 | 10/2019 | Bermudes |
| 10,463,730 B2 | 11/2019 | Szalay et al. |
| 10,465,205 B2 | 11/2019 | Bowen et al. |
| 10,472,623 B2 | 11/2019 | Igawa et al. |
| 10,501,746 B1 | 12/2019 | Bermudes |
| 11,129,906 B1* | 9/2021 | Bermudes ............ A61K 38/164 |
| 2001/0006642 A1 | 7/2001 | Steidler et al. |
| 2001/0009957 A1 | 7/2001 | Oaks et al. |
| 2001/0028881 A1 | 10/2001 | Roffler et al. |
| 2001/0029024 A1 | 10/2001 | Kodadek |
| 2001/0029043 A1 | 10/2001 | Haefliger et al. |
| 2001/0031485 A1 | 10/2001 | Backer et al. |
| 2001/0041333 A1 | 11/2001 | Short et al. |
| 2001/0046498 A1 | 11/2001 | Ruoslahti et al. |
| 2001/0053371 A1 | 12/2001 | Debinski et al. |
| 2002/0006645 A1 | 1/2002 | Hashimoto et al. |
| 2002/0012939 A1 | 1/2002 | Palsson |
| 2002/0015940 A1 | 2/2002 | Rao et al. |
| 2002/0016982 A1 | 2/2002 | Romaine et al. |
| 2002/0026655 A1 | 2/2002 | Bermudes et al. |
| 2002/0028914 A1 | 3/2002 | Yarkoni et al. |
| 2002/0031809 A1 | 3/2002 | Moeckel et al. |
| 2002/0031810 A1 | 3/2002 | Moeckel et al. |
| 2002/0032323 A1 | 3/2002 | Kunsch et al. |
| 2002/0037568 A1 | 3/2002 | Molenaar et al. |
| 2002/0039766 A1 | 4/2002 | Bathe et al. |
| 2002/0042105 A1 | 4/2002 | Bathe et al. |
| 2002/0042382 A1 | 4/2002 | Duffy et al. |
| 2002/0044919 A1 | 4/2002 | Yu |
| 2002/0045224 A1 | 4/2002 | Mockel et al. |
| 2002/0048795 A1 | 4/2002 | Farwick et al. |
| 2002/0051993 A1 | 5/2002 | Farwick et al. |
| 2002/0052486 A1 | 5/2002 | Bathe et al. |
| 2002/0055114 A1 | 5/2002 | Bathe et al. |
| 2002/0055115 A1 | 5/2002 | Farwick et al. |
| 2002/0055152 A1 | 5/2002 | Farwick et al. |
| 2002/0058277 A1 | 5/2002 | Bathe et al. |
| 2002/0061545 A1 | 5/2002 | Choi et al. |
| 2002/0064839 A1 | 5/2002 | Marx et al. |
| 2002/0068336 A1 | 6/2002 | Moeckel et al. |
| 2002/0072104 A1 | 6/2002 | Landry |
| 2002/0078473 A1 | 6/2002 | Estruch et al. |
| 2002/0081672 A1 | 6/2002 | Mockel et al. |
| 2002/0081674 A1 | 6/2002 | Moeckel et al. |
| 2002/0082236 A1 | 6/2002 | Black |
| 2002/0086372 A1 | 7/2002 | Mockel et al. |
| 2002/0086373 A1 | 7/2002 | Farwick et al. |
| 2002/0086374 A1 | 7/2002 | Farwick et al. |
| 2002/0086404 A1 | 7/2002 | Moeckel et al. |
| 2002/0090685 A1 | 7/2002 | Bathe et al. |
| 2002/0098554 A1 | 7/2002 | Farwick et al. |
| 2002/0102242 A1 | 8/2002 | Briles et al. |
| 2002/0102663 A1 | 8/2002 | Farwick et al. |
| 2002/0102668 A1 | 8/2002 | Farwick et al. |
| 2002/0102669 A1 | 8/2002 | Farwick et al. |
| 2002/0103338 A1 | 8/2002 | Choi |
| 2002/0103356 A1 | 8/2002 | Mockel et al. |
| 2002/0103357 A1 | 8/2002 | Bathe et al. |
| 2002/0106380 A1 | 8/2002 | Hung et al. |
| 2002/0106672 A1 | 8/2002 | Farwick et al. |
| 2002/0106749 A1 | 8/2002 | Farwick et al. |
| 2002/0106750 A1 | 8/2002 | Farwick et al. |
| 2002/0106751 A1 | 8/2002 | Farwick et al. |
| 2002/0106755 A1 | 8/2002 | Bathe et al. |
| 2002/0106756 A1 | 8/2002 | Bathe et al. |
| 2002/0106757 A1 | 8/2002 | Farwick et al. |
| 2002/0106758 A1 | 8/2002 | Farwick et al. |
| 2002/0106759 A1 | 8/2002 | Farwick et al. |
| 2002/0106760 A1 | 8/2002 | Bathe et al. |
| 2002/0107374 A1 | 8/2002 | Pallas et al. |
| 2002/0107377 A1 | 8/2002 | Farwick et al. |
| 2002/0107379 A1 | 8/2002 | Marx et al. |
| 2002/0110879 A1 | 8/2002 | Bathe et al. |
| 2002/0111468 A1 | 8/2002 | Bathe et al. |
| 2002/0115159 A1 | 8/2002 | Farwick et al. |
| 2002/0115160 A1 | 8/2002 | Farwick et al. |
| 2002/0115161 A1 | 8/2002 | Farwick et al. |
| 2002/0115162 A1 | 8/2002 | Farwick et al. |
| 2002/0119537 A1 | 8/2002 | Moeckel et al. |
| 2002/0119549 A1 | 8/2002 | Moeckel et al. |
| 2002/0120116 A1 | 8/2002 | Kunsch et al. |
| 2002/0123053 A1 | 9/2002 | Luo et al. |
| 2002/0127661 A1 | 9/2002 | Farwick et al. |
| 2002/0127687 A1 | 9/2002 | Shigenobu et al. |
| 2002/0127702 A1 | 9/2002 | Bernstein et al. |
| 2002/0132323 A1 | 9/2002 | Moeckel et al. |
| 2002/0137065 A1 | 9/2002 | Farwick et al. |
| 2002/0137073 A1 | 9/2002 | Bathe et al. |
| 2002/0142006 A1 | 10/2002 | McGhee et al. |
| 2002/0142404 A1 | 10/2002 | Farwick et al. |
| 2002/0146430 A1 | 10/2002 | Galen |
| 2002/0146782 A1 | 10/2002 | Bathe et al. |
| 2002/0150881 A1 | 10/2002 | Ladner et al. |
| 2002/0151001 A1 | 10/2002 | Moeckel et al. |
| 2002/0151063 A1 | 10/2002 | Lasham et al. |
| 2002/0151700 A1 | 10/2002 | Farwick et al. |
| 2002/0155519 A1 | 10/2002 | Lindner et al. |
| 2002/0155554 A1 | 10/2002 | Bathe et al. |
| 2002/0155557 A1 | 10/2002 | Moeckel et al. |
| 2002/0159972 A1 | 10/2002 | Debinski et al. |
| 2002/0168732 A1 | 11/2002 | Moeckel et al. |
| 2002/0176848 A1 | 11/2002 | Sizemore et al. |
| 2002/0177551 A1 | 11/2002 | Terman |
| 2002/0182689 A1 | 12/2002 | Bathe et al. |
| 2002/0192223 A1 | 12/2002 | Hellstrom et al. |
| 2002/0192674 A1 | 12/2002 | Hermann et al. |
| 2002/0197276 A1 | 12/2002 | Oaks et al. |
| 2002/0197605 A1 | 12/2002 | Nakagawa et al. |
| 2003/0008839 A1 | 1/2003 | van Rooij et al. |
| 2003/0009015 A1 | 1/2003 | Ulrich et al. |
| 2003/0022835 A1 | 1/2003 | Watson et al. |
| 2003/0031628 A1 | 2/2003 | Zhao et al. |
| 2003/0031666 A1 | 2/2003 | Debinski et al. |
| 2003/0031681 A1 | 2/2003 | McCart et al. |
| 2003/0031683 A1 | 2/2003 | Curtiss et al. |
| 2003/0036644 A1 | 2/2003 | Ulrich |
| 2003/0040619 A1 | 2/2003 | Edwards et al. |
| 2003/0044943 A1 | 3/2003 | Farwick et al. |
| 2003/0045492 A1 | 3/2003 | Tang et al. |
| 2003/0049264 A1 | 3/2003 | Foster et al. |
| 2003/0049648 A1 | 3/2003 | Choi |
| 2003/0059400 A1 | 3/2003 | Szalay |
| 2003/0059792 A1 | 3/2003 | Palsson et al. |
| 2003/0059923 A1 | 3/2003 | Feder et al. |
| 2003/0068328 A1 | 4/2003 | Vladoianu et al. |
| 2003/0068611 A1 | 4/2003 | Larossa et al. |
| 2003/0068791 A1 | 4/2003 | Miasnikov et al. |
| 2003/0072737 A1 | 4/2003 | Brines et al. |
| 2003/0073217 A1 | 4/2003 | Barr et al. |
| 2003/0077677 A1 | 4/2003 | Short et al. |
| 2003/0082219 A1 | 5/2003 | Warren et al. |
| 2003/0086919 A1 | 5/2003 | Rosenblum et al. |
| 2003/0087827 A1 | 5/2003 | Lindberg et al. |
| 2003/0092026 A1 | 5/2003 | Rey et al. |
| 2003/0092066 A1 | 5/2003 | Vinkemeier et al. |
| 2003/0092137 A1 | 5/2003 | Farwick et al. |
| 2003/0092139 A1 | 5/2003 | Wolf et al. |
| 2003/0092164 A1 | 5/2003 | Gross et al. |
| 2003/0100054 A1 | 5/2003 | Bathe et al. |
| 2003/0100071 A1 | 5/2003 | Apicella et al. |
| 2003/0100080 A1 | 5/2003 | Farwick et al. |
| 2003/0100099 A1 | 5/2003 | Moeckel et al. |
| 2003/0100108 A1 | 5/2003 | Altman et al. |
| 2003/0100488 A1 | 5/2003 | Boyle |
| 2003/0103958 A1 | 6/2003 | Short et al. |
| 2003/0104988 A1 | 6/2003 | Brines et al. |

(56) References Cited

U.S. PATENT DOCUMENTS

| | | |
|---|---|---|
| 2003/0105319 A1 | 6/2003 | Schnepf et al. |
| 2003/0106096 A1 | 6/2003 | Barry |
| 2003/0109014 A1 | 6/2003 | Burke et al. |
| 2003/0109026 A1 | 6/2003 | Bermudes et al. |
| 2003/0113293 A1 | 6/2003 | Bermudes et al. |
| 2003/0113343 A1 | 6/2003 | Tuomanen et al. |
| 2003/0113717 A1 | 6/2003 | Ladner et al. |
| 2003/0113879 A1 | 6/2003 | Farwick et al. |
| 2003/0115630 A1 | 6/2003 | Romano |
| 2003/0119154 A1 | 6/2003 | Dunican et al. |
| 2003/0124561 A1 | 7/2003 | Mach et al. |
| 2003/0125278 A1 | 7/2003 | Tang et al. |
| 2003/0129132 A1 | 7/2003 | Puri et al. |
| 2003/0129193 A1 | 7/2003 | Thorpe et al. |
| 2003/0131372 A1 | 7/2003 | Copenhaver et al. |
| 2003/0131376 A1 | 7/2003 | Okubara et al. |
| 2003/0138917 A1 | 7/2003 | Dunican et al. |
| 2003/0143558 A1 | 7/2003 | Mitchell et al. |
| 2003/0143650 A1 | 7/2003 | Steward et al. |
| 2003/0143651 A1 | 7/2003 | Steward et al. |
| 2003/0143676 A1 | 7/2003 | Strachan et al. |
| 2003/0144490 A1 | 7/2003 | Edwards et al. |
| 2003/0153527 A1 | 8/2003 | Powell et al. |
| 2003/0157113 A1 | 8/2003 | Terman |
| 2003/0157551 A1 | 8/2003 | Bathe et al. |
| 2003/0157666 A1 | 8/2003 | Farwick et al. |
| 2003/0158390 A1 | 8/2003 | Fishman et al. |
| 2003/0165875 A1 | 9/2003 | Colonna et al. |
| 2003/0166140 A1 | 9/2003 | Chen et al. |
| 2003/0166541 A1 | 9/2003 | Ruben et al. |
| 2003/0166884 A1 | 9/2003 | Moeckel et al. |
| 2003/0170211 A1 | 9/2003 | Goudsmit et al. |
| 2003/0170276 A1 | 9/2003 | Bermudes et al. |
| 2003/0170780 A1 | 9/2003 | Moeckel et al. |
| 2003/0170897 A1 | 9/2003 | Imai et al. |
| 2003/0175911 A1 | 9/2003 | Hans et al. |
| 2003/0180289 A1 | 9/2003 | Foster et al. |
| 2003/0186416 A1 | 10/2003 | Pallas et al. |
| 2003/0188335 A1 | 10/2003 | Tuli |
| 2003/0188336 A1 | 10/2003 | Corbin et al. |
| 2003/0194798 A1 | 10/2003 | Surber et al. |
| 2003/0198991 A1 | 10/2003 | Moeckel et al. |
| 2003/0199045 A1 | 10/2003 | Burke et al. |
| 2003/0202990 A1 | 10/2003 | Donovan et al. |
| 2003/0203377 A1 | 10/2003 | Milne Edwards et al. |
| 2003/0207271 A1 | 11/2003 | Holwitt et al. |
| 2003/0211476 A1 | 11/2003 | O'Mahony et al. |
| 2003/0211599 A1 | 11/2003 | Sabbadini et al. |
| 2003/0219462 A1 | 11/2003 | Steward et al. |
| 2003/0219722 A1 | 11/2003 | Ladner et al. |
| 2003/0219736 A1 | 11/2003 | Gonye et al. |
| 2003/0219881 A1 | 11/2003 | Brigitte et al. |
| 2003/0219886 A1 | 11/2003 | Ladner et al. |
| 2003/0224363 A1 | 12/2003 | Park et al. |
| 2003/0228678 A1 | 12/2003 | Bathe et al. |
| 2003/0229065 A1 | 12/2003 | Levy et al. |
| 2004/0005539 A1 | 1/2004 | Ladner et al. |
| 2004/0005695 A1 | 1/2004 | Miksch et al. |
| 2004/0005700 A1 | 1/2004 | Surber et al. |
| 2004/0009485 A1 | 1/2004 | Gonye et al. |
| 2004/0009490 A1 | 1/2004 | Glenn et al. |
| 2004/0009578 A1 | 1/2004 | Bathe et al. |
| 2004/0009936 A1 | 1/2004 | Tang et al. |
| 2004/0013658 A1 | 1/2004 | Fulton et al. |
| 2004/0014156 A1 | 1/2004 | Roffler et al. |
| 2004/0014177 A1 | 1/2004 | Navran, Jr. et al. |
| 2004/0018203 A1 | 1/2004 | Pastan et al. |
| 2004/0018967 A1 | 1/2004 | Enright et al. |
| 2004/0022805 A1 | 2/2004 | Narum et al. |
| 2004/0023205 A1 | 2/2004 | Ladner et al. |
| 2004/0023266 A1 | 2/2004 | Vivekananda et al. |
| 2004/0023282 A1 | 2/2004 | Luo et al. |
| 2004/0033549 A1 | 2/2004 | Greenberg et al. |
| 2004/0038307 A1 | 2/2004 | Lee et al. |
| 2004/0038372 A1 | 2/2004 | Bathe et al. |
| 2004/0043029 A1 | 3/2004 | Hellstrom et al. |
| 2004/0043458 A1 | 3/2004 | Bathe et al. |
| 2004/0052802 A1 | 3/2004 | Nuijten et al. |
| 2004/0054142 A1 | 3/2004 | Cassart et al. |
| 2004/0058849 A1 | 3/2004 | Sleeman et al. |
| 2004/0063181 A1 | 4/2004 | Duncan et al. |
| 2004/0067561 A1 | 4/2004 | Bathe et al. |
| 2004/0067562 A1 | 4/2004 | Bathe et al. |
| 2004/0071729 A1 | 4/2004 | Adderson et al. |
| 2004/0072218 A1 | 4/2004 | Quan Pan |
| 2004/0072270 A1 | 4/2004 | Fernandez-Salas et al. |
| 2004/0072723 A1 | 4/2004 | Palsson et al. |
| 2004/0073008 A1 | 4/2004 | Iglesias Perez et al. |
| 2004/0077540 A1 | 4/2004 | Quay |
| 2004/0082002 A1 | 4/2004 | Choi |
| 2004/0091505 A1 | 5/2004 | Abad et al. |
| 2004/0091969 A1 | 5/2004 | Agarwal et al. |
| 2004/0091976 A1 | 5/2004 | Deng et al. |
| 2004/0096426 A1 | 5/2004 | Chen et al. |
| 2004/0101531 A1 | 5/2004 | Curtiss et al. |
| 2004/0101932 A1 | 5/2004 | Naleway et al. |
| 2004/0106185 A1 | 6/2004 | Ranganathan |
| 2004/0106553 A1 | 6/2004 | Alekshun et al. |
| 2004/0110939 A1 | 6/2004 | Dumas Milne Edwards et al. |
| 2004/0115174 A1 | 6/2004 | Gilboa et al. |
| 2004/0115788 A1 | 6/2004 | Zheng et al. |
| 2004/0117863 A1 | 6/2004 | Edge et al. |
| 2004/0122216 A1 | 6/2004 | Nielsen et al. |
| 2004/0128716 A1 | 7/2004 | Narva et al. |
| 2004/0133930 A1 | 7/2004 | Cooper et al. |
| 2004/0136959 A1 | 7/2004 | Puri |
| 2004/0142373 A1 | 7/2004 | Gonye et al. |
| 2004/0142454 A1 | 7/2004 | Molenaar et al. |
| 2004/0146922 A1 | 7/2004 | Gonye et al. |
| 2004/0166565 A1 | 8/2004 | Backer et al. |
| 2004/0170987 A1 | 9/2004 | Usuda et al. |
| 2004/0171123 A1 | 9/2004 | Rosen et al. |
| 2004/0171130 A1 | 9/2004 | Yokoi et al. |
| 2004/0180359 A1 | 9/2004 | Moeckel et al. |
| 2004/0180371 A1 | 9/2004 | Clayman et al. |
| 2004/0180380 A1 | 9/2004 | Lee et al. |
| 2004/0191787 A1 | 9/2004 | Tanner et al. |
| 2004/0202648 A1 | 10/2004 | Cabezon et al. |
| 2004/0202663 A1 | 10/2004 | Hu et al. |
| 2004/0208897 A1 | 10/2004 | Curtiss et al. |
| 2004/0209285 A1 | 10/2004 | Moeckel et al. |
| 2004/0210398 A1 | 10/2004 | Palsson et al. |
| 2004/0214219 A1 | 10/2004 | Dunican et al. |
| 2004/0214236 A1 | 10/2004 | Brines et al. |
| 2004/0214783 A1 | 10/2004 | Terman |
| 2004/0219169 A1 | 11/2004 | Bermudes et al. |
| 2004/0220386 A1 | 11/2004 | Steward et al. |
| 2004/0229243 A1 | 11/2004 | Levy |
| 2004/0229255 A1 | 11/2004 | Hermann et al. |
| 2004/0229338 A1 | 11/2004 | King |
| 2004/0234455 A1 | 11/2004 | Szalay |
| 2004/0234956 A1 | 11/2004 | Kabat et al. |
| 2004/0234998 A1 | 11/2004 | Sibbesen et al. |
| 2004/0247611 A1 | 12/2004 | Bargatze et al. |
| 2004/0247617 A1 | 12/2004 | Liao et al. |
| 2004/0253628 A1 | 12/2004 | Bathe et al. |
| 2004/0258688 A1 | 12/2004 | Hawiger et al. |
| 2004/0266003 A1 | 12/2004 | Powell et al. |
| 2004/0266674 A1 | 12/2004 | Mills et al. |
| 2005/0003400 A1 | 1/2005 | Boyle |
| 2005/0003423 A1 | 1/2005 | Moeckel et al. |
| 2005/0008618 A1 | 1/2005 | Kaufman et al. |
| 2005/0008649 A1 | 1/2005 | Shin et al. |
| 2005/0009750 A1 | 1/2005 | Sleeman et al. |
| 2005/0013822 A1 | 1/2005 | Oaks et al. |
| 2005/0019335 A1 | 1/2005 | Lowery et al. |
| 2005/0026866 A1 | 2/2005 | Pawelek |
| 2005/0031643 A1 | 2/2005 | Szalay et al. |
| 2005/0032157 A1 | 2/2005 | Gal et al. |
| 2005/0032179 A1 | 2/2005 | Moeckel et al. |
| 2005/0036987 A1 | 2/2005 | Pawelek et al. |
| 2005/0042216 A1 | 2/2005 | Frantz et al. |
| 2005/0042229 A1 | 2/2005 | Yang et al. |
| 2005/0043526 A1 | 2/2005 | Bathe et al. |

(56)　　　　References Cited

U.S. PATENT DOCUMENTS

| | | |
|---|---|---|
| 2005/0053589 A1 | 3/2005 | Debinski et al. |
| 2005/0053958 A1 | 3/2005 | Roth et al. |
| 2005/0055746 A1 | 3/2005 | Michaud et al. |
| 2005/0059122 A1 | 3/2005 | Shen |
| 2005/0059592 A1 | 3/2005 | Kiener et al. |
| 2005/0063994 A1 | 3/2005 | Caplan et al. |
| 2005/0064526 A1 | 3/2005 | Ulrich et al. |
| 2005/0064527 A1 | 3/2005 | Levy et al. |
| 2005/0064562 A1 | 3/2005 | Farwick et al. |
| 2005/0069491 A1 | 3/2005 | Szalay et al. |
| 2005/0069532 A1 | 3/2005 | Weinrauch et al. |
| 2005/0069894 A1 | 3/2005 | Gottesman et al. |
| 2005/0069911 A1 | 3/2005 | Lee et al. |
| 2005/0070005 A1 | 3/2005 | Keller |
| 2005/0070007 A1 | 3/2005 | Romaine et al. |
| 2005/0074463 A1 | 4/2005 | Autran et al. |
| 2005/0074802 A1 | 4/2005 | Rey et al. |
| 2005/0079573 A1 | 4/2005 | Sibbesen |
| 2005/0079588 A1 | 4/2005 | Sindelar et al. |
| 2005/0084972 A1 | 4/2005 | Barr et al. |
| 2005/0089552 A1 | 4/2005 | Altman et al. |
| 2005/0089976 A1 | 4/2005 | Moeckel et al. |
| 2005/0089986 A1 | 4/2005 | Bathe et al. |
| 2005/0100973 A1 | 5/2005 | Steward et al. |
| 2005/0106151 A1 | 5/2005 | Shapiro |
| 2005/0106597 A1 | 5/2005 | Choi |
| 2005/0112139 A1 | 5/2005 | Karp |
| 2005/0112140 A1 | 5/2005 | Karp |
| 2005/0112141 A1 | 5/2005 | Terman |
| 2005/0112642 A1 | 5/2005 | Sleeman et al. |
| 2005/0112664 A1 | 5/2005 | Mockel et al. |
| 2005/0112730 A1 | 5/2005 | Dunican et al. |
| 2005/0112732 A1 | 5/2005 | Bathe et al. |
| 2005/0112733 A1 | 5/2005 | Burke et al. |
| 2005/0112751 A1 | 5/2005 | Fang et al. |
| 2005/0118187 A1 | 6/2005 | Yu |
| 2005/0118193 A1 | 6/2005 | Andino-Pavlovsky et al. |
| 2005/0124678 A1 | 6/2005 | Levy et al. |
| 2005/0130264 A1 | 6/2005 | Moeckel et al. |
| 2005/0130277 A1 | 6/2005 | Bathe et al. |
| 2005/0136404 A1 | 6/2005 | Doucette-Stamm et al. |
| 2005/0147590 A1 | 7/2005 | Sabbadini et al. |
| 2005/0148504 A1 | 7/2005 | Katunuma et al. |
| 2005/0158295 A1 | 7/2005 | Swiercz et al. |
| 2005/0166274 A1 | 7/2005 | French et al. |
| 2005/0180963 A1 | 8/2005 | Adams et al. |
| 2005/0180985 A9 | 8/2005 | Vladoianu et al. |
| 2005/0181439 A1 | 8/2005 | Choi et al. |
| 2005/0181464 A1 | 8/2005 | Edwards et al. |
| 2005/0181488 A1 | 8/2005 | Akhverdian et al. |
| 2005/0191684 A1 | 9/2005 | Zimenkov et al. |
| 2005/0202409 A1 | 9/2005 | Takami et al. |
| 2005/0202535 A1 | 9/2005 | Collier et al. |
| 2005/0203007 A1 | 9/2005 | Komiyama et al. |
| 2005/0208033 A1 | 9/2005 | Luquet et al. |
| 2005/0214317 A1 | 9/2005 | Karp |
| 2005/0214318 A1 | 9/2005 | Karp |
| 2005/0221439 A1 | 10/2005 | Bakaletz et al. |
| 2005/0221450 A1 | 10/2005 | Mockel et al. |
| 2005/0221454 A1 | 10/2005 | Bathe |
| 2005/0227917 A1 | 10/2005 | Williams et al. |
| 2005/0233424 A1 | 10/2005 | Farwick et al. |
| 2005/0241015 A1 | 10/2005 | Mach et al. |
| 2005/0241016 A1 | 10/2005 | Mach et al. |
| 2005/0249706 A1 | 11/2005 | Bermudes et al. |
| 2005/0249748 A1 | 11/2005 | Dubensky, Jr. et al. |
| 2005/0250196 A1 | 11/2005 | Paton et al. |
| 2005/0251885 A1 | 11/2005 | Michaud et al. |
| 2005/0255088 A1 | 11/2005 | Bermudes et al. |
| 2005/0255566 A1 | 11/2005 | Bathe et al. |
| 2005/0256049 A1 | 11/2005 | Yarkoni et al. |
| 2005/0257282 A1 | 11/2005 | Mach et al. |
| 2005/0260225 A1 | 11/2005 | Goldberg et al. |
| 2005/0260670 A1 | 11/2005 | Colonna et al. |
| 2005/0266536 A1 | 12/2005 | Wolf et al. |
| 2005/0266560 A1 | 12/2005 | Preuss et al. |
| 2005/0267103 A1 | 12/2005 | Hochman |
| 2005/0268359 A1 | 12/2005 | Mach et al. |
| 2005/0272060 A1 | 12/2005 | Tuli |
| 2005/0273882 A1 | 12/2005 | Romano |
| 2005/0281828 A1 | 12/2005 | Bowdish et al. |
| 2005/0282239 A1 | 12/2005 | Allbritton et al. |
| 2005/0282259 A1 | 12/2005 | Moeckel et al. |
| 2005/0287639 A1 | 12/2005 | Kwon et al. |
| 2006/0008465 A1 | 1/2006 | Steinaa et al. |
| 2006/0009633 A9 | 1/2006 | Dumas Milne Edwards et al. |
| 2006/0014212 A1 | 1/2006 | Benkovic et al. |
| 2006/0014259 A9 | 1/2006 | Burke et al. |
| 2006/0015969 A1 | 1/2006 | Larrick et al. |
| 2006/0018914 A1 | 1/2006 | Hellstrom et al. |
| 2006/0019356 A1 | 1/2006 | Usuda et al. |
| 2006/0019357 A1 | 1/2006 | Moeckel et al. |
| 2006/0024668 A1 | 2/2006 | Hoek |
| 2006/0025387 A1 | 2/2006 | Hochman |
| 2006/0026695 A1 | 2/2006 | Edge et al. |
| 2006/0030010 A1 | 2/2006 | Usuda et al. |
| 2006/0034799 A1 | 2/2006 | Brines et al. |
| 2006/0035270 A1 | 2/2006 | Lee et al. |
| 2006/0035320 A1 | 2/2006 | Tissot et al. |
| 2006/0035371 A1 | 2/2006 | Zheng et al. |
| 2006/0035813 A1 | 2/2006 | Sternberg et al. |
| 2006/0039929 A1 | 2/2006 | Fernandez-Salas et al. |
| 2006/0040317 A1 | 2/2006 | Farwick et al. |
| 2006/0051356 A1 | 3/2006 | Foster et al. |
| 2006/0051370 A1 | 3/2006 | Szalay et al. |
| 2006/0051839 A1 | 3/2006 | Robinson et al. |
| 2006/0057152 A1 | 3/2006 | Marshall |
| 2006/0063221 A1 | 3/2006 | Williams et al. |
| 2006/0063222 A1 | 3/2006 | Williams et al. |
| 2006/0073168 A1 | 4/2006 | Stephens et al. |
| 2006/0083716 A1 | 4/2006 | Kaufman et al. |
| 2006/0084113 A1 | 4/2006 | Ladner et al. |
| 2006/0088910 A1 | 4/2006 | Nguyen |
| 2006/0089350 A1 | 4/2006 | Hochman et al. |
| 2006/0094672 A1 | 5/2006 | Pasqualini et al. |
| 2006/0104955 A1 | 5/2006 | Redshaw |
| 2006/0110747 A1 | 5/2006 | Ramseier et al. |
| 2006/0112447 A1 | 5/2006 | Bogdanova et al. |
| 2006/0115483 A1 | 6/2006 | Sleeman et al. |
| 2006/0121056 A1 | 6/2006 | Chaddock et al. |
| 2006/0127408 A1 | 6/2006 | Young et al. |
| 2006/0134761 A1 | 6/2006 | Moeckel et al. |
| 2006/0134791 A1 | 6/2006 | Black |
| 2006/0135754 A1 | 6/2006 | Christensen et al. |
| 2006/0140975 A1 | 6/2006 | Curtiss et al. |
| 2006/0153876 A1 | 7/2006 | Sanders |
| 2006/0154314 A9 | 7/2006 | Steward et al. |
| 2006/0156440 A1 | 7/2006 | Michaud et al. |
| 2006/0160152 A1 | 7/2006 | Vinkemeier et al. |
| 2006/0160799 A1 | 7/2006 | Alekshun et al. |
| 2006/0166338 A1 | 7/2006 | Bathe et al. |
| 2006/0167229 A1 | 7/2006 | Wong et al. |
| 2006/0174357 A1 | 8/2006 | Velander et al. |
| 2006/0177912 A1 | 8/2006 | Farwick et al. |
| 2006/0182685 A1 | 8/2006 | Bishai et al. |
| 2006/0182762 A1 | 8/2006 | Irene Martina Maas et al. |
| 2006/0216283 A1 | 9/2006 | Foster et al. |
| 2006/0216757 A1 | 9/2006 | Brines et al. |
| 2006/0222633 A1 | 10/2006 | Shlomchik et al. |
| 2006/0223142 A1 | 10/2006 | Dumas Milne Edwards et al. |
| 2006/0228712 A1 | 10/2006 | Nakagawa et al. |
| 2006/0229336 A1 | 10/2006 | Kazmierski et al. |
| 2006/0233829 A1 | 10/2006 | Curtiss |
| 2006/0234331 A1 | 10/2006 | Yazaki et al. |
| 2006/0234358 A1 | 10/2006 | Anderlei et al. |
| 2006/0234943 A1 | 10/2006 | Wong |
| 2006/0239968 A1 | 10/2006 | Arap et al. |
| 2006/0241050 A1 | 10/2006 | Cameron et al. |
| 2006/0246554 A1 | 11/2006 | Thierbach et al. |
| 2006/0263368 A1 | 11/2006 | Rosenblum et al. |
| 2006/0269540 A1 | 11/2006 | Robert et al. |
| 2006/0269561 A1 | 11/2006 | Paterson et al. |
| 2006/0270043 A1 | 11/2006 | Blattner et al. |
| 2006/0275823 A1 | 12/2006 | Kodadek |

(56) References Cited

U.S. PATENT DOCUMENTS

| | | |
|---|---|---|
| 2006/0275874 A1 | 12/2006 | Matsuno et al. |
| 2006/0275897 A1 | 12/2006 | Nabel et al. |
| 2006/0280749 A1 | 12/2006 | Rosenblum et al. |
| 2006/0281908 A1 | 12/2006 | Callen |
| 2006/0286639 A1 | 12/2006 | Dumas Milne Edwards et al. |
| 2007/0004666 A1 | 1/2007 | Lasham et al. |
| 2007/0006340 A1 | 1/2007 | Lang et al. |
| 2007/0009489 A1 | 1/2007 | Bermudes et al. |
| 2007/0009900 A1 | 1/2007 | Doucette-Stamm et al. |
| 2007/0009901 A1 | 1/2007 | Doucette-Stamm et al. |
| 2007/0009902 A1 | 1/2007 | Doucette-Stamm et al. |
| 2007/0009903 A1 | 1/2007 | Doucette-Stamm et al. |
| 2007/0009904 A1 | 1/2007 | Doucette-Stamm et al. |
| 2007/0009905 A1 | 1/2007 | Doucette-Stamm et al. |
| 2007/0009906 A1 | 1/2007 | Doucette-Stamm et al. |
| 2007/0009932 A1 | 1/2007 | Stephanopoulos et al. |
| 2007/0015271 A1 | 1/2007 | Rosen et al. |
| 2007/0020327 A1 | 1/2007 | Fikes et al. |
| 2007/0025981 A1 | 2/2007 | Szalay et al. |
| 2007/0026507 A1 | 2/2007 | Olivo et al. |
| 2007/0028324 A1 | 2/2007 | Corbin et al. |
| 2007/0031382 A1 | 2/2007 | Powell et al. |
| 2007/0031852 A1 | 2/2007 | Doucette-Stamm et al. |
| 2007/0032639 A1 | 2/2007 | Gottesman et al. |
| 2007/0037744 A1 | 2/2007 | Gallo et al. |
| 2007/0038419 A1 | 2/2007 | Usuda et al. |
| 2007/0041997 A1 | 2/2007 | Finlay et al. |
| 2007/0059709 A1 | 3/2007 | Benton et al. |
| 2007/0059799 A1 | 3/2007 | Sette et al. |
| 2007/0059801 A1 | 3/2007 | Doucette-Stamm et al. |
| 2007/0059802 A1 | 3/2007 | Doucette-Stamm et al. |
| 2007/0059807 A1 | 3/2007 | Wisniewski et al. |
| 2007/0059836 A1 | 3/2007 | Black |
| 2007/0065820 A1 | 3/2007 | Jiang et al. |
| 2007/0065908 A1 | 3/2007 | Gallo et al. |
| 2007/0071675 A1 | 3/2007 | Wu et al. |
| 2007/0071773 A1 | 3/2007 | Hanski et al. |
| 2007/0072279 A1 | 3/2007 | Meynial-Salles et al. |
| 2007/0087403 A1 | 4/2007 | Bestel-Corre et al. |
| 2007/0092951 A1 | 4/2007 | Bathe et al. |
| 2007/0104689 A1 | 5/2007 | Gillies et al. |
| 2007/0110721 A1 | 5/2007 | Cranenburgh |
| 2007/0110752 A1 | 5/2007 | Murison et al. |
| 2007/0111291 A1 | 5/2007 | Bathe et al. |
| 2007/0116671 A1 | 5/2007 | Prakash et al. |
| 2007/0116725 A1 | 5/2007 | Vladoianu et al. |
| 2007/0118934 A1 | 5/2007 | Yu et al. |
| 2007/0122832 A1 | 5/2007 | Mockel et al. |
| 2007/0122858 A1 | 5/2007 | Fernandez-Salas et al. |
| 2007/0122881 A1 | 5/2007 | Surber |
| 2007/0134264 A1 | 6/2007 | Marshall |
| 2007/0134768 A1 | 6/2007 | Zelder et al. |
| 2007/0141680 A1 | 6/2007 | Bathe et al. |
| 2007/0143871 A1 | 6/2007 | French et al. |
| 2007/0154458 A1 | 7/2007 | McCart et al. |
| 2007/0154986 A1 | 7/2007 | Kunsch et al. |
| 2007/0178116 A1 | 8/2007 | Adderson et al. |
| 2007/0178492 A1 | 8/2007 | Gross et al. |
| 2007/0178505 A1 | 8/2007 | Fischer et al. |
| 2007/0184048 A1 | 8/2007 | Foster et al. |
| 2007/0184517 A1 | 8/2007 | Schultz et al. |
| 2007/0184528 A1 | 8/2007 | Pierce et al. |
| 2007/0184543 A1 | 8/2007 | Pierce et al. |
| 2007/0191262 A1 | 8/2007 | Racila et al. |
| 2007/0192905 A1 | 8/2007 | Piller et al. |
| 2007/0202572 A1 | 8/2007 | Szalay et al. |
| 2007/0202578 A1 | 8/2007 | Samain et al. |
| 2007/0202591 A1 | 8/2007 | Ulrich |
| 2007/0212311 A1 | 9/2007 | Burne et al. |
| 2007/0212711 A1 | 9/2007 | Choi et al. |
| 2007/0212727 A1 | 9/2007 | Szalay et al. |
| 2007/0224666 A1 | 9/2007 | Bathe et al. |
| 2007/0231820 A1 | 10/2007 | Weiner et al. |
| 2007/0231867 A1 | 10/2007 | Choi et al. |
| 2007/0243303 A1 | 10/2007 | Dan Hengst et al. |
| 2007/0243565 A1 | 10/2007 | Williams et al. |
| 2007/0243616 A1 | 10/2007 | Church et al. |
| 2007/0244047 A1 | 10/2007 | Rosen et al. |
| 2007/0254329 A1 | 11/2007 | Rubin |
| 2007/0254846 A1 | 11/2007 | Wong et al. |
| 2007/0254850 A1 | 11/2007 | Lieberman et al. |
| 2007/0258889 A1 | 11/2007 | Douglas et al. |
| 2007/0259408 A1 | 11/2007 | Bathe et al. |
| 2007/0259417 A1 | 11/2007 | Ladner et al. |
| 2007/0264689 A1 | 11/2007 | Gross et al. |
| 2007/0269369 A1 | 11/2007 | Gegg et al. |
| 2007/0269414 A1 | 11/2007 | Okano et al. |
| 2007/0269871 A1 | 11/2007 | Zelder et al. |
| 2007/0275423 A1 | 11/2007 | Sebastian et al. |
| 2007/0281342 A1 | 12/2007 | DeAngelis |
| 2007/0287171 A1 | 12/2007 | Inouye |
| 2007/0298012 A1 | 12/2007 | King et al. |
| 2007/0299008 A1 | 12/2007 | Rummel |
| 2008/0003240 A1 | 1/2008 | Fernandez-Salas et al. |
| 2008/0004206 A1 | 1/2008 | Rosen et al. |
| 2008/0009041 A1 | 1/2008 | Mizoguchi et al. |
| 2008/0009446 A1 | 1/2008 | Yu et al. |
| 2008/0014618 A1 | 1/2008 | Bathe et al. |
| 2008/0019994 A1 | 1/2008 | Brunham et al. |
| 2008/0031877 A1 | 2/2008 | Covacci et al. |
| 2008/0032318 A1 | 2/2008 | Steward et al. |
| 2008/0032374 A1 | 2/2008 | Zelder et al. |
| 2008/0038274 A1 | 2/2008 | Foster et al. |
| 2008/0038296 A1 | 2/2008 | Brahmbhatt et al. |
| 2008/0038756 A1 | 2/2008 | Steward et al. |
| 2008/0038779 A1 | 2/2008 | Miasnikov et al. |
| 2008/0038787 A1 | 2/2008 | Zelder et al. |
| 2008/0050774 A1 | 2/2008 | Berka et al. |
| 2008/0050786 A1 | 2/2008 | Bathe et al. |
| 2008/0063666 A1 | 3/2008 | Allende |
| 2008/0064054 A1 | 3/2008 | Fernandez-Salas et al. |
| 2008/0064062 A1 | 3/2008 | Leonhartsberger et al. |
| 2008/0064762 A1 | 3/2008 | Fuchs et al. |
| 2008/0070255 A1 | 3/2008 | Tanner et al. |
| 2008/0070840 A1 | 3/2008 | Min et al. |
| 2008/0076157 A1 | 3/2008 | Leonhartsberger et al. |
| 2008/0089862 A1 | 4/2008 | Benhar et al. |
| 2008/0090770 A1 | 4/2008 | Belmares et al. |
| 2008/0095806 A1 | 4/2008 | Bathurst et al. |
| 2008/0102115 A1 | 5/2008 | Oyhenart et al. |
| 2008/0118948 A1 | 5/2008 | Kroger et al. |
| 2008/0124355 A1 | 5/2008 | Bermudes |
| 2008/0131903 A1 | 6/2008 | Thierbach et al. |
| 2008/0131927 A1 | 6/2008 | Schischka et al. |
| 2008/0146786 A1 | 6/2008 | Steward et al. |
| 2008/0160121 A1 | 7/2008 | Donovan et al. |
| 2008/0160561 A1 | 7/2008 | Fernandez-Salas et al. |
| 2008/0160585 A1 | 7/2008 | Zelder et al. |
| 2008/0166739 A1 | 7/2008 | Steward et al. |
| 2008/0166757 A1 | 7/2008 | Bron et al. |
| 2008/0166764 A1 | 7/2008 | Schloesser et al. |
| 2008/0166775 A1 | 7/2008 | Kroger et al. |
| 2008/0171014 A1 | 7/2008 | Wu et al. |
| 2008/0171348 A1 | 7/2008 | Steward et al. |
| 2008/0176249 A1 | 7/2008 | Steward et al. |
| 2008/0176295 A1 | 7/2008 | Zelder et al. |
| 2008/0176336 A1 | 7/2008 | Steward et al. |
| 2008/0181892 A1 | 7/2008 | Ledbetter et al. |
| 2008/0182295 A1 | 7/2008 | Patkar et al. |
| 2008/0182799 A1 | 7/2008 | Fernandez-Salas et al. |
| 2008/0187520 A1 | 8/2008 | Polack et al. |
| 2008/0187960 A1 | 8/2008 | Foster et al. |
| 2008/0193373 A1 | 8/2008 | Stritzker et al. |
| 2008/0193470 A1 | 8/2008 | Masignani et al. |
| 2008/0193974 A1 | 8/2008 | Coleman et al. |
| 2008/0194481 A1 | 8/2008 | Rosen et al. |
| 2008/0199926 A1 | 8/2008 | Burgard et al. |
| 2008/0206271 A1 | 8/2008 | Liao et al. |
| 2008/0206284 A1 | 8/2008 | Williams et al. |
| 2008/0206814 A1 | 8/2008 | Lee et al. |
| 2008/0206818 A1 | 8/2008 | Wich et al. |
| 2008/0213316 A1 | 9/2008 | Tarasenko |
| 2008/0213796 A1 | 9/2008 | Steward et al. |
| 2008/0214469 A1 | 9/2008 | Lam et al. |

(56) References Cited

U.S. PATENT DOCUMENTS

| | | |
|---|---|---|
| 2008/0220456 A1 | 9/2008 | Williams et al. |
| 2008/0226551 A1 | 9/2008 | Waugh et al. |
| 2008/0227704 A1 | 9/2008 | Kamens |
| 2008/0233623 A1 | 9/2008 | Chang et al. |
| 2008/0242620 A1 | 10/2008 | Wong et al. |
| 2008/0249013 A1 | 10/2008 | Cabezon et al. |
| 2008/0254511 A1 | 10/2008 | Dassler et al. |
| 2008/0260769 A1 | 10/2008 | Capecchi et al. |
| 2008/0261269 A1 | 10/2008 | Bathe et al. |
| 2008/0261869 A1 | 10/2008 | Shapiro |
| 2008/0267966 A1 | 10/2008 | Masignani et al. |
| 2008/0268502 A1 | 10/2008 | Haefner et al. |
| 2008/0269070 A1 | 10/2008 | Ramseier et al. |
| 2008/0270096 A1 | 10/2008 | Palsson |
| 2008/0274155 A1 | 11/2008 | Barton et al. |
| 2008/0274265 A1 | 11/2008 | Bathe et al. |
| 2008/0274516 A1 | 11/2008 | Kroger et al. |
| 2008/0280346 A1 | 11/2008 | de Lorenzo Prieto et al. |
| 2008/0280354 A1 | 11/2008 | Perez et al. |
| 2008/0286290 A1 | 11/2008 | Furusako et al. |
| 2008/0286306 A1 | 11/2008 | Nabel et al. |
| 2008/0286841 A1 | 11/2008 | Kroger et al. |
| 2008/0288264 A1 | 11/2008 | Mach et al. |
| 2008/0293084 A1 | 11/2008 | Williams et al. |
| 2008/0293085 A1 | 11/2008 | Williams et al. |
| 2008/0293100 A1 | 11/2008 | Wendisch et al. |
| 2008/0305119 A1 | 12/2008 | Dewhurst et al. |
| 2008/0305509 A1 | 12/2008 | Williams et al. |
| 2008/0305510 A1 | 12/2008 | Williams et al. |
| 2008/0305533 A1 | 12/2008 | Yi et al. |
| 2008/0311081 A1 | 12/2008 | Fruehauf et al. |
| 2008/0311096 A1 | 12/2008 | Lang et al. |
| 2008/0311125 A1 | 12/2008 | O'Keefe et al. |
| 2008/0317731 A1 | 12/2008 | Gramatikova et al. |
| 2008/0318286 A1 | 12/2008 | Choi et al. |
| 2008/0319167 A1 | 12/2008 | Foster et al. |
| 2009/0004215 A1 | 1/2009 | Tuli et al. |
| 2009/0004705 A1 | 1/2009 | Kroger et al. |
| 2009/0004744 A1 | 1/2009 | Surber et al. |
| 2009/0004745 A1 | 1/2009 | Choi et al. |
| 2009/0010917 A1 | 1/2009 | Rosenblum et al. |
| 2009/0010956 A1 | 1/2009 | Rikihisa |
| 2009/0011490 A1 | 1/2009 | Sabbadini et al. |
| 2009/0011974 A1 | 1/2009 | Bocharov et al. |
| 2009/0011995 A1 | 1/2009 | Lee et al. |
| 2009/0019609 A1 | 1/2009 | Romano |
| 2009/0023157 A1 | 1/2009 | Lee et al. |
| 2009/0023182 A1 | 1/2009 | Schilling |
| 2009/0023649 A1 | 1/2009 | Backer et al. |
| 2009/0028890 A1 | 1/2009 | Karp |
| 2009/0029425 A1 | 1/2009 | Zelder et al. |
| 2009/0035827 A1 | 2/2009 | Stephens et al. |
| 2009/0042231 A1 | 2/2009 | Steward et al. |
| 2009/0042248 A1 | 2/2009 | Gal et al. |
| 2009/0042278 A1 | 2/2009 | Barr et al. |
| 2009/0042785 A1 | 2/2009 | Matschiner et al. |
| 2009/0053186 A1 | 2/2009 | Hu et al. |
| 2009/0053746 A1 | 2/2009 | Steward et al. |
| 2009/0053794 A1 | 2/2009 | Bathe et al. |
| 2009/0054323 A1 | 2/2009 | Oliner et al. |
| 2009/0061006 A1 | 3/2009 | Leuschner et al. |
| 2009/0061445 A1 | 3/2009 | Oltvai et al. |
| 2009/0062139 A1 | 3/2009 | Short et al. |
| 2009/0068226 A1 | 3/2009 | Ulrich et al. |
| 2009/0069241 A1 | 3/2009 | Barnstable et al. |
| 2009/0069248 A1 | 3/2009 | Motin et al. |
| 2009/0075333 A1 | 3/2009 | Campbell et al. |
| 2009/0081193 A1 | 3/2009 | Sasisekharan et al. |
| 2009/0081199 A1 | 3/2009 | Colonna et al. |
| 2009/0081673 A1 | 3/2009 | Shen et al. |
| 2009/0082549 A1 | 3/2009 | Fishman et al. |
| 2009/0092632 A1 | 4/2009 | Lee |
| 2009/0098049 A1 | 4/2009 | Dowdy et al. |
| 2009/0111160 A1 | 4/2009 | Collier et al. |
| 2009/0117047 A1 | 5/2009 | Szalay et al. |
| 2009/0117048 A1 | 5/2009 | Szalay et al. |
| 2009/0117049 A1 | 5/2009 | Szalay et al. |
| 2009/0117572 A1 | 5/2009 | Fernandez-Salas et al. |
| 2009/0118475 A1 | 5/2009 | Steward et al. |
| 2009/0123382 A1 | 5/2009 | Szalay et al. |
| 2009/0123426 A1 | 5/2009 | Li et al. |
| 2009/0123921 A1 | 5/2009 | Georgiou et al. |
| 2009/0130709 A1 | 5/2009 | Hamilton |
| 2009/0131401 A1 | 5/2009 | Levy et al. |
| 2009/0131645 A1 | 5/2009 | Foster et al. |
| 2009/0136519 A1 | 5/2009 | Brines et al. |
| 2009/0136542 A1 | 5/2009 | Karp |
| 2009/0142343 A1 | 6/2009 | Fuh et al. |
| 2009/0155238 A1 | 6/2009 | Weiner et al. |
| 2009/0155866 A1 | 6/2009 | Burk et al. |
| 2009/0156794 A1 | 6/2009 | Black, Jr. |
| 2009/0162341 A1 | 6/2009 | Foster et al. |
| 2009/0162356 A1 | 6/2009 | Lookeren Campagne |
| 2009/0162933 A1 | 6/2009 | Kiener et al. |
| 2009/0169517 A1 | 7/2009 | Bermudes et al. |
| 2009/0169566 A1 | 7/2009 | Rawlin et al. |
| 2009/0170155 A1 | 7/2009 | Johnson et al. |
| 2009/0170170 A1 | 7/2009 | Choi et al. |
| 2009/0170812 A1 | 7/2009 | Alekshun et al. |
| 2009/0175829 A1 | 7/2009 | Forbes et al. |
| 2009/0175897 A1 | 7/2009 | Tang et al. |
| 2009/0180955 A1 | 7/2009 | Stritzker et al. |
| 2009/0180987 A1 | 7/2009 | Stritzker et al. |
| 2009/0181894 A1 | 7/2009 | Yarkoni et al. |
| 2009/0186377 A1 | 7/2009 | Johnson et al. |
| 2009/0186384 A1 | 7/2009 | Matsuno et al. |
| 2009/0191583 A1 | 7/2009 | Fernandez-Salas et al. |
| 2009/0191599 A1 | 7/2009 | Devroe et al. |
| 2009/0203070 A1 | 8/2009 | Devroe et al. |
| 2009/0203103 A1 | 8/2009 | Pierce et al. |
| 2009/0208534 A1 | 8/2009 | Xu et al. |
| 2009/0209749 A1 | 8/2009 | Mach et al. |
| 2009/0214506 A1 | 8/2009 | Hardy et al. |
| 2009/0215130 A1 | 8/2009 | Iyo et al. |
| 2009/0215133 A1 | 8/2009 | Bathe et al. |
| 2009/0215754 A1 | 8/2009 | Hochman et al. |
| 2009/0217396 A1 | 8/2009 | Kyrkanides et al. |
| 2009/0220480 A1 | 9/2009 | Gray et al. |
| 2009/0220540 A1 | 9/2009 | Marshall |
| 2009/0221055 A1 | 9/2009 | Kadoya et al. |
| 2009/0226372 A1 | 9/2009 | Ruoslahti et al. |
| 2009/0226919 A1 | 9/2009 | Gulevich et al. |
| 2009/0232801 A1 | 9/2009 | Hillen et al. |
| 2009/0232804 A1 | 9/2009 | Lazarides et al. |
| 2009/0233844 A1 | 9/2009 | Brines et al. |
| 2009/0234101 A1 | 9/2009 | Ladner et al. |
| 2009/0238789 A1 | 9/2009 | Guyon et al. |
| 2009/0238798 A1 | 9/2009 | Bogdanova et al. |
| 2009/0239797 A1 | 9/2009 | Cooper et al. |
| 2009/0240073 A1 | 9/2009 | Barry |
| 2009/0246220 A1 | 10/2009 | Ertl et al. |
| 2009/0246832 A1 | 10/2009 | Wakarchuk et al. |
| 2009/0246836 A1 | 10/2009 | Kroger et al. |
| 2009/0246838 A1 | 10/2009 | Zelder et al. |
| 2009/0253164 A1 | 10/2009 | Unrean et al. |
| 2009/0258401 A1 | 10/2009 | Iyo et al. |
| 2009/0258935 A1 | 10/2009 | Zheng et al. |
| 2009/0263836 A1 | 10/2009 | Fernandez-Salas et al. |
| 2009/0269364 A1* | 10/2009 | Zielinski ........ A61K 39/001106 424/185.1 |
| 2009/0271894 A1 | 10/2009 | Benfey et al. |
| 2009/0275097 A1 | 11/2009 | Sun et al. |
| 2009/0275104 A1 | 11/2009 | Berka et al. |
| 2009/0280542 A1 | 11/2009 | Bathe et al. |
| 2009/0291457 A1 | 11/2009 | Foster et al. |
| 2009/0294288 A1 | 12/2009 | May et al. |
| 2009/0297560 A1 | 12/2009 | Dattwyler et al. |
| 2009/0298136 A1 | 12/2009 | Zelder et al. |
| 2009/0299044 A1 | 12/2009 | Sullivan et al. |
| 2009/0300779 A1 | 12/2009 | Zhao et al. |
| 2009/0304693 A1 | 12/2009 | Ghayur et al. |
| 2009/0305296 A1 | 12/2009 | Bengtsson et al. |
| 2009/0311253 A1 | 12/2009 | Ghayur et al. |
| 2009/0311744 A1 | 12/2009 | DeFrees et al. |

(56)    References Cited

U.S. PATENT DOCUMENTS

| | | |
|---|---|---|
| 2009/0311756 A1 | 12/2009 | Zelder et al. |
| 2009/0317404 A1 | 12/2009 | Markham |
| 2009/0317418 A1 | 12/2009 | Catanzaro et al. |
| 2009/0317839 A1 | 12/2009 | Fernandez-Salas et al. |
| 2009/0324576 A1 | 12/2009 | Padmanabhan et al. |
| 2009/0324651 A1 | 12/2009 | Old et al. |
| 2009/0325242 A1 | 12/2009 | Bathe et al. |
| 2009/0325298 A1 | 12/2009 | Kernodle |
| 2009/0325866 A1 | 12/2009 | Kim et al. |
| 2010/0003727 A1 | 1/2010 | Zelder et al. |
| 2010/0008851 A1 | 1/2010 | Nicolaides et al. |
| 2010/0008946 A1 | 1/2010 | Szalay et al. |
| 2010/0011456 A1 | 1/2010 | Mathur et al. |
| 2010/0015672 A1 | 1/2010 | Takagi et al. |
| 2010/0015674 A1 | 1/2010 | Zelder et al. |
| 2010/0016227 A1 | 1/2010 | Enright et al. |
| 2010/0021510 A1 | 1/2010 | Carreno Serraima et al. |
| 2010/0021978 A1 | 1/2010 | Burk et al. |
| 2010/0022584 A1 | 1/2010 | Kenyon et al. |
| 2010/0028340 A1 | 2/2010 | Mueller et al. |
| 2010/0034822 A1 | 2/2010 | Masignani et al. |
| 2010/0040537 A1 | 2/2010 | Gu et al. |
| 2010/0040640 A1 | 2/2010 | Lanar et al. |
| 2010/0041107 A1 | 2/2010 | Herold et al. |
| 2010/0047239 A1 | 2/2010 | Wu et al. |
| 2010/0047245 A1 | 2/2010 | Lacy et al. |
| 2010/0055727 A1 | 3/2010 | Steward et al. |
| 2010/0055761 A1 | 3/2010 | Seed et al. |
| 2010/0062016 A1 | 3/2010 | Szalay et al. |
| 2010/0062438 A1 | 3/2010 | Danchin |
| 2010/0062535 A1 | 3/2010 | Kroger et al. |
| 2010/0064393 A1 | 3/2010 | Berka et al. |
| 2010/0068173 A1 | 3/2010 | Yu et al. |
| 2010/0069610 A1 | 3/2010 | Steward et al. |
| 2010/0074900 A1 | 3/2010 | Ghayur et al. |
| 2010/0074933 A1 | 3/2010 | Prakash et al. |
| 2010/0075346 A1 | 3/2010 | Steward et al. |
| 2010/0075357 A1 | 3/2010 | Steward et al. |
| 2010/0075358 A1 | 3/2010 | Steward et al. |
| 2010/0080815 A1 | 4/2010 | Zavada et al. |
| 2010/0081155 A1 | 4/2010 | Williams et al. |
| 2010/0081156 A1 | 4/2010 | Williams et al. |
| 2010/0081157 A1 | 4/2010 | Steward et al. |
| 2010/0081158 A1 | 4/2010 | Steward et al. |
| 2010/0086546 A1 | 4/2010 | Lee et al. |
| 2010/0092438 A1 | 4/2010 | Fruehauf et al. |
| 2010/0093639 A1 | 4/2010 | Waugh et al. |
| 2010/0095398 A1 | 4/2010 | Meana et al. |
| 2010/0104560 A1 | 4/2010 | Chapman et al. |
| 2010/0104607 A1 | 4/2010 | Engelberg-Kulka et al. |
| 2010/0105106 A1 | 4/2010 | Ronin et al. |
| 2010/0111998 A1 | 5/2010 | Nabel et al. |
| 2010/0112670 A1 | 5/2010 | Giacalone et al. |
| 2010/0119550 A1 | 5/2010 | Gomi et al. |
| 2010/0119588 A1 | 5/2010 | Sato et al. |
| 2010/0120105 A1 | 5/2010 | Anthony et al. |
| 2010/0121042 A1 | 5/2010 | Fernandez-Salas et al. |
| 2010/0124558 A1 | 5/2010 | Curtiss, III et al. |
| 2010/0135961 A1 | 6/2010 | Bermudes |
| 2010/0135973 A1 | 6/2010 | Eisenstark et al. |
| 2010/0136027 A1 | 6/2010 | Kim |
| 2010/0136048 A1 | 6/2010 | Bermudes |
| 2010/0136657 A1 | 6/2010 | Jokinen et al. |
| 2010/0137162 A1 | 6/2010 | Retallack et al. |
| 2010/0137192 A1 | 6/2010 | Shapiro |
| 2010/0143997 A1 | 6/2010 | Buelter et al. |
| 2010/0144543 A1 | 6/2010 | Witcher et al. |
| 2010/0150965 A1 | 6/2010 | Kopecko et al. |
| 2010/0151494 A1 | 6/2010 | Steward et al. |
| 2010/0158952 A1 | 6/2010 | Goletz |
| 2010/0159523 A1 | 6/2010 | Bathe et al. |
| 2010/0160609 A1 | 6/2010 | Fernandez-Salas et al. |
| 2010/0160612 A1 | 6/2010 | Skerra et al. |
| 2010/0166802 A1 | 7/2010 | Caplan et al. |
| 2010/0168387 A1 | 7/2010 | Tuli |
| 2010/0169988 A1 | 7/2010 | Kohli et al. |
| 2010/0172976 A1 | 7/2010 | Satishchandran et al. |
| 2010/0183516 A1 | 7/2010 | Ribbert et al. |
| 2010/0184157 A1 | 7/2010 | Williams et al. |
| 2010/0184613 A1 | 7/2010 | Lee et al. |
| 2010/0189686 A1 | 7/2010 | Rosen et al. |
| 2010/0189691 A1 | 7/2010 | Fruehauf et al. |
| 2010/0189740 A1 | 7/2010 | Michon et al. |
| 2010/0189774 A1 | 7/2010 | Lenormand |
| 2010/0196315 A1 | 8/2010 | Lacy et al. |
| 2010/0196959 A1 | 8/2010 | Schischka et al. |
| 2010/0209405 A1 | 8/2010 | Altman et al. |
| 2010/0209955 A1 | 8/2010 | Oyler et al. |
| 2010/0215679 A1 | 8/2010 | Horwitz et al. |
| 2010/0215682 A1 | 8/2010 | Berkower |
| 2010/0216720 A1 | 8/2010 | Brophy et al. |
| 2010/0221179 A1 | 9/2010 | Hsieh et al. |
| 2010/0221779 A1 | 9/2010 | Short et al. |
| 2010/0227850 A1 | 9/2010 | Alekshun et al. |
| 2010/0233079 A1 | 9/2010 | Jakob et al. |
| 2010/0233195 A1 | 9/2010 | Delisa et al. |
| 2010/0233814 A1 | 9/2010 | Williams |
| 2010/0239546 A1 | 9/2010 | Fruehauf et al. |
| 2010/0247544 A1 | 9/2010 | Vachon |
| 2010/0247560 A1 | 9/2010 | Simpson et al. |
| 2010/0249026 A1 | 9/2010 | Rosen et al. |
| 2010/0255022 A1 | 10/2010 | Prescott et al. |
| 2010/0255036 A1 | 10/2010 | Hassan et al. |
| 2010/0255544 A1 | 10/2010 | Bathe et al. |
| 2010/0255553 A1 | 10/2010 | Srienc et al. |
| 2010/0260668 A1 | 10/2010 | Ghayur et al. |
| 2010/0261201 A1 | 10/2010 | Katanaev |
| 2010/0261257 A1 | 10/2010 | Bathe et al. |
| 2010/0269223 A1 | 10/2010 | Lira et al. |
| 2010/0272750 A1 | 10/2010 | Buyse et al. |
| 2010/0278819 A1 | 11/2010 | Bossuyt et al. |
| 2010/0279923 A1 | 11/2010 | Schulte et al. |
| 2010/0280222 A1 | 11/2010 | Steward et al. |
| 2010/0281577 A1 | 11/2010 | Mulet Salort et al. |
| 2010/0285547 A1 | 11/2010 | Soucaille et al. |
| 2010/0285564 A1 | 11/2010 | Skerra et al. |
| 2010/0286060 A1 | 11/2010 | Oliner et al. |
| 2010/0286251 A1 | 11/2010 | Rubin |
| 2010/0290996 A1 | 11/2010 | Nickerson et al. |
| 2010/0291033 A1 | 11/2010 | Rosen et al. |
| 2010/0291088 A1 | 11/2010 | Ghayur et al. |
| 2010/0292091 A1 | 11/2010 | Levy |
| 2010/0292429 A1 | 11/2010 | Volkert et al. |
| 2010/0303822 A1 | 12/2010 | Masignani et al. |
| 2010/0305306 A1 | 12/2010 | Colonna et al. |
| 2010/0310560 A1 | 12/2010 | Colonna et al. |
| 2010/0310593 A1 | 12/2010 | Brazer et al. |
| 2010/0311147 A1 | 12/2010 | Bathe et al. |
| 2010/0317007 A1 | 12/2010 | Palsson et al. |
| 2010/0317569 A1 | 12/2010 | Lira et al. |
| 2010/0319087 A1 | 12/2010 | Corbin et al. |
| 2010/0319092 A1 | 12/2010 | Lira et al. |
| 2010/0319093 A1 | 12/2010 | Lira et al. |
| 2010/0333235 A1 | 12/2010 | Mach et al. |
| 2011/0002910 A1 | 1/2011 | Rosenblum et al. |
| 2011/0003963 A1 | 1/2011 | Zelder et al. |
| 2011/0008392 A1 | 1/2011 | Buck et al. |
| 2011/0008828 A1 | 1/2011 | Kwon et al. |
| 2011/0014666 A1 | 1/2011 | Voelker et al. |
| 2011/0014672 A1 | 1/2011 | Chotani et al. |
| 2011/0014701 A1 | 1/2011 | Ghosh |
| 2011/0021416 A1 | 1/2011 | Shapiro |
| 2011/0027309 A1 | 2/2011 | Bottje et al. |
| 2011/0027349 A1 | 2/2011 | Sable et al. |
| 2011/0028397 A1 | 2/2011 | Tozser et al. |
| 2011/0033501 A1 | 2/2011 | Curtiss, III et al. |
| 2011/0038865 A1 | 2/2011 | Shin et al. |
| 2011/0038917 A1 | 2/2011 | Kappers et al. |
| 2011/0039313 A1 | 2/2011 | Verseck et al. |
| 2011/0044980 A1 | 2/2011 | Ghayur et al. |
| 2011/0045587 A1 | 2/2011 | Sullivan et al. |
| 2011/0053253 A1 | 3/2011 | Kim et al. |
| 2011/0054442 A1 | 3/2011 | Sanders |
| 2011/0065091 A1 | 3/2011 | Van Der Hoek |

(56)			References Cited

U.S. PATENT DOCUMENTS

| | | |
|---|---|---|
| 2011/0086407 A1 | 4/2011 | Berka et al. |
| 2011/0091372 A1 | 4/2011 | Ghayur et al. |
| 2011/0091463 A1 | 4/2011 | Ghayur et al. |
| 2011/0091493 A1 | 4/2011 | Moahamadzadeh et al. |
| 2011/0093965 A1 | 4/2011 | O'Donoghue et al. |
| 2011/0104146 A1 | 5/2011 | Faraday |
| 2011/0104163 A1 | 5/2011 | Dimitrov et al. |
| 2011/0104196 A1 | 5/2011 | Karp |
| 2011/0104240 A1 | 5/2011 | Jones et al. |
| 2011/0104789 A1 | 5/2011 | Wu et al. |
| 2011/0106000 A1 | 5/2011 | Jones et al. |
| 2011/0111015 A1 | 5/2011 | Bottje et al. |
| 2011/0111458 A1 | 5/2011 | Masuda et al. |
| 2011/0111481 A1 | 5/2011 | Li |
| 2011/0111496 A1 | 5/2011 | Li |
| 2011/0117079 A1 | 5/2011 | Benatuil et al. |
| 2011/0117611 A1 | 5/2011 | Dunican et al. |
| 2011/0117617 A1 | 5/2011 | Liu et al. |
| 2011/0124073 A1 | 5/2011 | Devroe et al. |
| 2011/0125118 A1 | 5/2011 | Lynch |
| 2011/0135646 A1 | 6/2011 | Bakaletz et al. |
| 2011/0136759 A1 | 6/2011 | Kahne et al. |
| 2011/0142761 A1 | 6/2011 | Wu et al. |
| 2011/0152174 A1 | 6/2011 | Foster et al. |
| 2011/0152176 A1 | 6/2011 | Horswill |
| 2011/0159026 A1 | 6/2011 | Bottje et al. |
| 2011/0165063 A1 | 7/2011 | Hsieh et al. |
| 2011/0165066 A1 | 7/2011 | Wu et al. |
| 2011/0165660 A1 | 7/2011 | Picataggio et al. |
| 2011/0165661 A1 | 7/2011 | Picataggio et al. |
| 2011/0165680 A1 | 7/2011 | Blattner et al. |
| 2011/0166336 A1 | 7/2011 | Gottesman et al. |
| 2011/0171695 A1 | 7/2011 | Bathe et al. |
| 2011/0171727 A1 | 7/2011 | Black, Jr. |
| 2011/0177053 A1 | 7/2011 | Foster et al. |
| 2011/0189773 A1 | 8/2011 | Altman et al. |
| 2011/0189774 A1 | 8/2011 | Mach et al. |
| 2011/0190234 A1 | 8/2011 | Nathan et al. |
| 2011/0195090 A1 | 8/2011 | Dimitrov |
| 2011/0195423 A1 | 8/2011 | Selinfreund et al. |
| 2011/0201070 A1 | 8/2011 | Soucaille et al. |
| 2011/0201109 A1 | 8/2011 | Zwaka et al. |
| 2011/0206616 A1 | 8/2011 | Ichtchenko et al. |
| 2011/0207183 A1 | 8/2011 | Herold et al. |
| 2011/0207187 A1 | 8/2011 | Tokuda et al. |
| 2011/0212094 A1 | 9/2011 | Ghayur et al. |
| 2011/0217237 A1 | 9/2011 | Chen et al. |
| 2011/0223241 A1 | 9/2011 | Tardi et al. |
| 2011/0224416 A1 | 9/2011 | Picataggio et al. |
| 2011/0225663 A1 | 9/2011 | Von Schaewen et al. |
| 2011/0229959 A1 | 9/2011 | Picataggio et al. |
| 2011/0230523 A1 | 9/2011 | Levy et al. |
| 2011/0243980 A1 | 10/2011 | Feldman et al. |
| 2011/0243992 A1 | 10/2011 | Kernodle |
| 2011/0244529 A1 | 10/2011 | Claes et al. |
| 2011/0244575 A1 | 10/2011 | Lipscomb et al. |
| 2011/0245169 A1 | 10/2011 | Brines et al. |
| 2011/0250199 A1 | 10/2011 | Fitzgerald et al. |
| 2011/0251095 A1 | 10/2011 | Levy |
| 2011/0257080 A1 | 10/2011 | Chai et al. |
| 2011/0262347 A1 | 10/2011 | Ruoslahti et al. |
| 2011/0262474 A1 | 10/2011 | Du et al. |
| 2011/0262980 A1 | 10/2011 | Soucaille et al. |
| 2011/0263500 A1 | 10/2011 | Hansel et al. |
| 2011/0268661 A1 | 11/2011 | Markiv et al. |
| 2011/0268760 A1 | 11/2011 | Telfer et al. |
| 2011/0269201 A1 | 11/2011 | Gray et al. |
| 2011/0274719 A1 | 11/2011 | Marshall |
| 2011/0274721 A1 | 11/2011 | Nabel et al. |
| 2011/0275122 A1 | 11/2011 | Min et al. |
| 2011/0275585 A1 | 11/2011 | Brahmbhatt et al. |
| 2011/0277180 A1 | 11/2011 | Romano |
| 2011/0280800 A1 | 11/2011 | Wu et al. |
| 2011/0280830 A9 | 11/2011 | Rosen et al. |
| 2011/0281330 A1 | 11/2011 | Sabbadini et al. |
| 2011/0286916 A1 | 11/2011 | Aste-Amezaga et al. |
| 2011/0287037 A1 | 11/2011 | Gentschev et al. |
| 2011/0293608 A1 | 12/2011 | Jaffee et al. |
| 2011/0294170 A1 | 12/2011 | Subbian et al. |
| 2011/0300099 A1 | 12/2011 | Debinski et al. |
| 2011/0300176 A1 | 12/2011 | Szalay et al. |
| 2011/0300177 A1 | 12/2011 | Gin et al. |
| 2011/0305724 A1 | 12/2011 | Paterson et al. |
| 2011/0306611 A1 | 12/2011 | Alekshun et al. |
| 2011/0307978 A1 | 12/2011 | Bogdanova et al. |
| 2011/0318308 A1 | 12/2011 | Ragolia |
| 2011/0318316 A1 | 12/2011 | Wong et al. |
| 2011/0318317 A1 | 12/2011 | Wong et al. |
| 2011/0318349 A1 | 12/2011 | Ghayur et al. |
| 2011/0318357 A1 | 12/2011 | O'Brien et al. |
| 2012/0009194 A1 | 1/2012 | Ferrone et al. |
| 2012/0009196 A1 | 1/2012 | Muerhoff et al. |
| 2012/0009205 A1 | 1/2012 | Gegg et al. |
| 2012/0009627 A1 | 1/2012 | Deng et al. |
| 2012/0014941 A1 | 1/2012 | Wu et al. |
| 2012/0014957 A1 | 1/2012 | Ghayur et al. |
| 2012/0020883 A1 | 1/2012 | Stritzker et al. |
| 2012/0021517 A1 | 1/2012 | Jin et al. |
| 2012/0021985 A1 | 1/2012 | Rosen et al. |
| 2012/0027785 A1 | 2/2012 | Dirienzo |
| 2012/0028324 A1 | 2/2012 | Buelter et al. |
| 2012/0034160 A1 | 2/2012 | Ghayur et al. |
| 2012/0039985 A1 | 2/2012 | de Muinck et al. |
| 2012/0040414 A1 | 2/2012 | Knight |
| 2012/0040426 A1 | 2/2012 | Sun et al. |
| 2012/0042413 A1 | 2/2012 | Albert et al. |
| 2012/0045474 A1 | 2/2012 | Motin et al. |
| 2012/0058098 A1 | 3/2012 | Foster et al. |
| 2012/0058532 A1 | 3/2012 | Buelter et al. |
| 2012/0064062 A1 | 3/2012 | Goguen et al. |
| 2012/0064568 A1 | 3/2012 | Hamilton |
| 2012/0064572 A1 | 3/2012 | Finlay et al. |
| 2012/0070870 A1 | 3/2012 | Way et al. |
| 2012/0070881 A1 | 3/2012 | Berka et al. |
| 2012/0071545 A1 | 3/2012 | Shapiro |
| 2012/0076758 A1 | 3/2012 | Diamond et al. |
| 2012/0076803 A1 | 3/2012 | Brophy et al. |
| 2012/0077237 A1 | 3/2012 | Picataggio et al. |
| 2012/0077252 A1 | 3/2012 | Picataggio et al. |
| 2012/0083587 A1 | 4/2012 | Gallo et al. |
| 2012/0087858 A1 | 4/2012 | Ghayur et al. |
| 2012/0087946 A1 | 4/2012 | Curtiss, III et al. |
| 2012/0088314 A1 | 4/2012 | Katanaev |
| 2012/0093773 A1 | 4/2012 | Li et al. |
| 2012/0093805 A1 | 4/2012 | Kubota |
| 2012/0093868 A1 | 4/2012 | Masignani et al. |
| 2012/0094341 A1 | 4/2012 | Burk et al. |
| 2012/0094906 A1 | 4/2012 | Guyon et al. |
| 2012/0100140 A1 | 4/2012 | Reyes et al. |
| 2012/0100581 A1 | 4/2012 | Gramatikova et al. |
| 2012/0101027 A1 | 4/2012 | Foster et al. |
| 2012/0107360 A1 | 5/2012 | Le Butt et al. |
| 2012/0108521 A1 | 5/2012 | Eggink et al. |
| 2012/0108640 A1 | 5/2012 | Hochman et al. |
| 2012/0114652 A1 | 5/2012 | Elvin et al. |
| 2012/0121637 A1 | 5/2012 | Granoff et al. |
| 2012/0122762 A1 | 5/2012 | Ruben et al. |
| 2012/0122962 A1 | 5/2012 | Han et al. |
| 2012/0128594 A1 | 5/2012 | Choy et al. |
| 2012/0128624 A1 | 5/2012 | Yu et al. |
| 2012/0128718 A1 | 5/2012 | Hassan et al. |
| 2012/0135503 A1 | 5/2012 | Sabbadini et al. |
| 2012/0141415 A1 | 6/2012 | Ballance et al. |
| 2012/0141511 A1 | 6/2012 | Foster et al. |
| 2012/0142079 A1 | 6/2012 | Sabbadini et al. |
| 2012/0142080 A1 | 6/2012 | Bermudes |
| 2012/0142589 A1 | 6/2012 | Brines et al. |
| 2012/0142623 A1 | 6/2012 | Lagunoff et al. |
| 2012/0144509 A1 | 6/2012 | Benghezal et al. |
| 2012/0148601 A1 | 6/2012 | Ulrich et al. |
| 2012/0148615 A1 | 6/2012 | Masignani et al. |
| 2012/0149095 A1 | 6/2012 | Kopecko et al. |
| 2012/0156186 A1 | 6/2012 | Foster et al. |
| 2012/0156803 A1 | 6/2012 | Evans et al. |

(56)                    References Cited

U.S. PATENT DOCUMENTS

| | | |
|---|---|---|
| 2012/0159674 A1 | 6/2012 | Meade et al. |
| 2012/0164687 A1 | 6/2012 | Bereta et al. |
| 2012/0164703 A1 | 6/2012 | Yi et al. |
| 2012/0171234 A1 | 7/2012 | Wong et al. |
| 2012/0177682 A1 | 7/2012 | Marshall |
| 2012/0184007 A1 | 7/2012 | Picataggio et al. |
| 2012/0184020 A1 | 7/2012 | Picataggio et al. |
| 2012/0189541 A1 | 7/2012 | Wu |
| 2012/0189572 A1 | 7/2012 | Wei et al. |
| 2012/0190011 A1 | 7/2012 | Brummelkamp et al. |
| 2012/0190089 A1 | 7/2012 | Buelter et al. |
| 2012/0195900 A1 | 8/2012 | Ghayur et al. |
| 2012/0195922 A1 | 8/2012 | Lee |
| 2012/0207735 A1 | 8/2012 | Foster et al. |
| 2012/0208181 A1 | 8/2012 | Merighi et al. |
| 2012/0210467 A1 | 8/2012 | Barton et al. |
| 2012/0213767 A1 | 8/2012 | Wei et al. |
| 2012/0219545 A1 | 8/2012 | Ayuso et al. |
| 2012/0220757 A1 | 8/2012 | Christensen et al. |
| 2012/0225454 A1 | 9/2012 | Benghezal et al. |
| 2012/0230976 A1 | 9/2012 | Helmerhorst et al. |
| 2012/0231538 A1 | 9/2012 | Fernandez-Salas et al. |
| 2012/0232012 A1 | 9/2012 | Popel et al. |
| 2012/0237491 A1 | 9/2012 | Padmanabhan et al. |
| 2012/0244600 A1 | 9/2012 | Jin |
| 2012/0244621 A1 | 9/2012 | Weiss et al. |
| 2012/0252074 A1 | 10/2012 | Zhang et al. |
| 2012/0252097 A1 | 10/2012 | Rosenblum et al. |
| 2012/0252099 A1 | 10/2012 | Sabbadini et al. |
| 2012/0253009 A1 | 10/2012 | Walker |
| 2012/0258108 A1 | 10/2012 | Ghayur et al. |
| 2012/0258521 A1 | 10/2012 | Liu et al. |
| 2012/0263722 A1 | 10/2012 | Ghayur et al. |
| 2012/0264686 A9 | 10/2012 | Guyon et al. |
| 2012/0264902 A1 | 10/2012 | Lipscomb et al. |
| 2012/0266328 A1 | 10/2012 | Gray et al. |
| 2012/0266329 A1 | 10/2012 | Mathur et al. |
| 2012/0271036 A1 | 10/2012 | Smith et al. |
| 2012/0275996 A1 | 11/2012 | Hsieh |
| 2012/0276010 A1 | 11/2012 | Szalay et al. |
| 2012/0276132 A1 | 11/2012 | Feng et al. |
| 2012/0276587 A1 | 11/2012 | Beck et al. |
| 2012/0276603 A1 | 11/2012 | Beck et al. |
| 2012/0277143 A1 | 11/2012 | Jacobs et al. |
| 2012/0282700 A1 | 11/2012 | Lunder et al. |
| 2012/0282701 A1 | 11/2012 | Kopecko et al. |
| 2012/0288901 A1 | 11/2012 | Zelder et al. |
| 2012/0301493 A1 | 11/2012 | Brandariz Nunez et al. |
| 2012/0301497 A1 | 11/2012 | Yadava et al. |
| 2012/0308484 A1 | 12/2012 | Szalay et al. |
| 2012/0308575 A1 | 12/2012 | Guo et al. |
| 2012/0308594 A1 | 12/2012 | Sablon et al. |
| 2012/0311745 A1 | 12/2012 | Meade et al. |
| 2012/0317681 A1 | 12/2012 | Meade et al. |
| 2012/0317682 A1 | 12/2012 | Meade et al. |
| 2012/0324606 A1 | 12/2012 | Meade et al. |
| 2012/0329150 A1 | 12/2012 | Duke et al. |
| 2012/0331589 A1 | 12/2012 | Meade et al. |
| 2012/0331590 A1 | 12/2012 | Meade et al. |
| 2013/0004416 A1 | 1/2013 | Wu et al. |
| 2013/0004537 A1 | 1/2013 | Curtiss et al. |
| 2013/0004998 A1 | 1/2013 | Subbian et al. |
| 2013/0004999 A1 | 1/2013 | Reth et al. |
| 2013/0007923 A1 | 1/2013 | Meade et al. |
| 2013/0011409 A1 | 1/2013 | Shipp et al. |
| 2013/0011421 A1 | 1/2013 | Gin et al. |
| 2013/0011874 A1 | 1/2013 | Campbell et al. |
| 2013/0017173 A1 | 1/2013 | Nataro et al. |
| 2013/0022539 A1 | 1/2013 | Pilkington et al. |
| 2013/0022578 A1 | 1/2013 | Newman et al. |
| 2013/0023472 A1 | 1/2013 | Bristow |
| 2013/0025006 A1 | 1/2013 | Meade et al. |
| 2013/0028901 A1 | 1/2013 | Colonna et al. |
| 2013/0028924 A1 | 1/2013 | Ertl et al. |
| 2013/0036520 A1 | 2/2013 | Meade et al. |
| 2013/0042374 A1 | 2/2013 | Meade et al. |
| 2013/0045184 A1 | 2/2013 | Teitelbaum |
| 2013/0052227 A1 | 2/2013 | Gerke et al. |
| 2013/0059318 A1 | 3/2013 | Kaneko et al. |
| 2013/0065274 A1 | 3/2013 | Gerngross et al. |
| 2013/0066035 A1 | 3/2013 | Burgard et al. |
| 2013/0071893 A1 | 3/2013 | Lynch et al. |
| 2013/0078254 A1 | 3/2013 | Bakaletz et al. |
| 2013/0078275 A1 | 3/2013 | Tao |
| 2013/0084304 A1 | 4/2013 | Hargis et al. |
| 2013/0089906 A1 | 4/2013 | Beck et al. |
| 2013/0095488 A1 | 4/2013 | Bogdanova et al. |
| 2013/0095566 A1 | 4/2013 | Oltvai et al. |
| 2013/0097729 A1 | 4/2013 | Bonning et al. |
| 2013/0101577 A9 | 4/2013 | Wei et al. |
| 2013/0102017 A1 | 4/2013 | Pfaendler et al. |
| 2013/0102530 A1 | 4/2013 | Brines et al. |
| 2013/0122043 A1 | 5/2013 | Guimaraes et al. |
| 2013/0122526 A1 | 5/2013 | Foster et al. |
| 2013/0122541 A1 | 5/2013 | Lynch et al. |
| 2013/0122553 A1 | 5/2013 | Maertens et al. |
| 2013/0122565 A1 | 5/2013 | Pierce et al. |
| 2013/0129713 A1 | 5/2013 | Rescigno et al. |
| 2013/0129737 A1 | 5/2013 | Adderson et al. |
| 2013/0129761 A1 | 5/2013 | Garcia-Sastre et al. |
| 2013/0130292 A1 | 5/2013 | Szalay et al. |
| 2013/0142937 A1 | 6/2013 | Bathe et al. |
| 2013/0149313 A1 | 6/2013 | Gu et al. |
| 2013/0150559 A1 | 6/2013 | Colonna et al. |
| 2013/0164257 A1 | 6/2013 | Debinski et al. |
| 2013/0164307 A1 | 6/2013 | Markham |
| 2013/0164317 A1 | 6/2013 | Yousef et al. |
| 2013/0164329 A1 | 6/2013 | Rossomando et al. |
| 2013/0164380 A1 | 6/2013 | Durum et al. |
| 2013/0164808 A1 | 6/2013 | Mcauliffe et al. |
| 2013/0164809 A1 | 6/2013 | Chotani et al. |
| 2013/0171096 A1 | 7/2013 | Hsieh et al. |
| 2013/0171109 A1 | 7/2013 | Helmerhorst et al. |
| 2013/0171182 A1 | 7/2013 | Whelan et al. |
| 2013/0171190 A1 | 7/2013 | Curtiss, III et al. |
| 2013/0177555 A1 | 7/2013 | Wilkinson et al. |
| 2013/0183728 A1 | 7/2013 | Botes et al. |
| 2013/0189753 A1 | 7/2013 | Pearlman et al. |
| 2013/0190241 A1 | 7/2013 | Wong et al. |
| 2013/0190255 A1 | 7/2013 | Wong et al. |
| 2013/0196432 A1 | 8/2013 | Poehlmann et al. |
| 2013/0197194 A1 | 8/2013 | Kaplan et al. |
| 2013/0197203 A1 | 8/2013 | Michon et al. |
| 2013/0202557 A1 | 8/2013 | Li et al. |
| 2013/0202598 A1 | 8/2013 | Benhar et al. |
| 2013/0202623 A1 | 8/2013 | Chomont et al. |
| 2013/0203130 A1 | 8/2013 | Wittmann et al. |
| 2013/0203164 A1 | 8/2013 | Rosen et al. |
| 2013/0203657 A1 | 8/2013 | Meade et al. |
| 2013/0205416 A1 | 8/2013 | Nash et al. |
| 2013/0209405 A1 | 8/2013 | Roy et al. |
| 2013/0209407 A1 | 8/2013 | Hamer |
| 2013/0209499 A1 | 8/2013 | Garcia-Sastre et al. |
| 2013/0210073 A1 | 8/2013 | Kwon et al. |
| 2013/0210077 A1 | 8/2013 | Brzezinski et al. |
| 2013/0210121 A1 | 8/2013 | Giacalone et al. |
| 2013/0210149 A1 | 8/2013 | Li |
| 2013/0210747 A1 | 8/2013 | Hamm-Alvarez et al. |
| 2013/0211170 A1 | 8/2013 | Amano et al. |
| 2013/0216555 A1 | 8/2013 | Nitsch et al. |
| 2013/0216568 A1 | 8/2013 | Maione et al. |
| 2013/0217068 A1 | 8/2013 | Parkot et al. |
| 2013/0217145 A1 | 8/2013 | Yoshimura et al. |
| 2013/0219570 A1 | 8/2013 | Lira et al. |
| 2013/0224804 A1 | 8/2013 | Knight |
| 2013/0227741 A1 | 8/2013 | Gray et al. |
| 2013/0243747 A1 | 9/2013 | Fima et al. |
| 2013/0247254 A1 | 9/2013 | Lira et al. |
| 2013/0266585 A1 | 10/2013 | Nitsch et al. |
| 2013/0269057 A1 | 10/2013 | Fosu-Nyarko et al. |
| 2013/0273590 A1 | 10/2013 | Oyler et al. |
| 2013/0273613 A1 | 10/2013 | Devroe et al. |
| 2013/0274187 A1 | 10/2013 | Mogelsvang et al. |
| 2013/0276168 A1 | 10/2013 | Romaine et al. |

(56) References Cited

U.S. PATENT DOCUMENTS

| | | |
|---|---|---|
| 2013/0280774 A1 | 10/2013 | Blake et al. |
| 2013/0287810 A1 | 10/2013 | Mohamadzadeh et al. |
| 2013/0295054 A1 | 11/2013 | Huang et al. |
| 2013/0295072 A1 | 11/2013 | Fima et al. |
| 2013/0295127 A1 | 11/2013 | Prescott et al. |
| 2013/0295616 A1 | 11/2013 | Muramatsu et al. |
| 2013/0295643 A1 | 11/2013 | Foster et al. |
| 2013/0310458 A1 | 11/2013 | Eggeling et al. |
| 2013/0316397 A1 | 11/2013 | Airen et al. |
| 2013/0316426 A1 | 11/2013 | Burk et al. |
| 2013/0318640 A1 | 11/2013 | Oldenburg et al. |
| 2013/0323801 A1 | 12/2013 | Chilton et al. |
| 2013/0330350 A1 | 12/2013 | Dimasi |
| 2013/0330709 A1 | 12/2013 | Beatty et al. |
| 2013/0330796 A1 | 12/2013 | Beck et al. |
| 2013/0330824 A1 | 12/2013 | Li |
| 2013/0337516 A1 | 12/2013 | Herrema |
| 2013/0337545 A1 | 12/2013 | Sabbadini et al. |
| 2013/0344033 A1 | 12/2013 | Vergnolle et al. |
| 2013/0345114 A1 | 12/2013 | Williams et al. |
| 2014/0004598 A1 | 1/2014 | Picataggio et al. |
| 2014/0005108 A1 | 1/2014 | Bristow |
| 2014/0010811 A1 | 1/2014 | Ferrone et al. |
| 2014/0010829 A1 | 1/2014 | Bigner et al. |
| 2014/0017765 A1 | 1/2014 | Subbian et al. |
| 2014/0024050 A1 | 1/2014 | Yoshimura et al. |
| 2014/0024820 A1 | 1/2014 | Parkot et al. |
| 2014/0031541 A1 | 1/2014 | Heidtman et al. |
| 2014/0037695 A1 | 2/2014 | Yu |
| 2014/0044748 A1 | 2/2014 | Lee |
| 2014/0045231 A1 | 2/2014 | Lynch et al. |
| 2014/0045261 A1 | 2/2014 | Wang et al. |
| 2014/0050693 A1 | 2/2014 | Skerra et al. |
| 2014/0051132 A1 | 2/2014 | Samsonova et al. |
| 2014/0051136 A1 | 2/2014 | Liao et al. |
| 2014/0056841 A1 | 2/2014 | Vachon |
| 2014/0057940 A1 | 2/2014 | Mankowski et al. |
| 2014/0072595 A1 | 3/2014 | Benghezal et al. |
| 2014/0073683 A1 | 3/2014 | Han et al. |
| 2014/0079701 A1 | 3/2014 | Miller et al. |
| 2014/0080201 A1 | 3/2014 | Merighi et al. |
| 2014/0086950 A1 | 3/2014 | Pascual et al. |
| 2014/0093521 A1 | 4/2014 | Benatuil et al. |
| 2014/0093528 A1 | 4/2014 | Berkower |
| 2014/0093534 A1 | 4/2014 | Bottje et al. |
| 2014/0093540 A1 | 4/2014 | Wright et al. |
| 2014/0093885 A1 | 4/2014 | Hua et al. |
| 2014/0093925 A1 | 4/2014 | Guettler et al. |
| 2014/0094404 A1 | 4/2014 | Villaverde Corrales et al. |
| 2014/0099670 A1 | 4/2014 | Kostenuik et al. |
| 2014/0099671 A1 | 4/2014 | Wu et al. |
| 2014/0105863 A1 | 4/2014 | Vanden-Broucke et al. |
| 2014/0112951 A1 | 4/2014 | Tang et al. |
| 2014/0113376 A1 | 4/2014 | Sorek et al. |
| 2014/0127216 A1 | 5/2014 | Balraj et al. |
| 2014/0127221 A1 | 5/2014 | Bakaletz et al. |
| 2014/0127765 A1 | 5/2014 | Osterhout et al. |
| 2014/0127780 A1 | 5/2014 | Zhang et al. |
| 2014/0134171 A1 | 5/2014 | Ghayur et al. |
| 2014/0134682 A1 | 5/2014 | Wittmann et al. |
| 2014/0134690 A1 | 5/2014 | Yan et al. |
| 2014/0141482 A1 | 5/2014 | Pearlman et al. |
| 2014/0148582 A1 | 5/2014 | Gallo et al. |
| 2014/0150134 A1 | 5/2014 | Li et al. |
| 2014/0154250 A1 | 6/2014 | Thompson et al. |
| 2014/0154252 A1 | 6/2014 | Thompson et al. |
| 2014/0154256 A1 | 6/2014 | Wu et al. |
| 2014/0154762 A1 | 6/2014 | Duehring et al. |
| 2014/0155343 A1 | 6/2014 | Brahmbhatt et al. |
| 2014/0155581 A1 | 6/2014 | Gao et al. |
| 2014/0161767 A1 | 6/2014 | Leuschner et al. |
| 2014/0161800 A1 | 6/2014 | Blankenship et al. |
| 2014/0162279 A1 | 6/2014 | Ramseier et al. |
| 2014/0162337 A1 | 6/2014 | Chotani et al. |
| 2014/0162952 A1 | 6/2014 | Katagiri et al. |
| 2014/0173774 A1 | 6/2014 | Pareddy et al. |
| 2014/0173780 A1 | 6/2014 | Pareddy et al. |
| 2014/0178341 A1 | 6/2014 | Zhao et al. |
| 2014/0182018 A1 | 6/2014 | Lang et al. |
| 2014/0186377 A1 | 7/2014 | Gu et al. |
| 2014/0186401 A1 | 7/2014 | Diamond et al. |
| 2014/0186884 A1 | 7/2014 | Nunn, Jr. et al. |
| 2014/0186902 A1 | 7/2014 | Botes et al. |
| 2014/0186904 A1 | 7/2014 | Botes et al. |
| 2014/0186913 A1 | 7/2014 | Botes et al. |
| 2014/0187491 A1 | 7/2014 | Wilmen et al. |
| 2014/0189896 A1 | 7/2014 | Zhang et al. |
| 2014/0193861 A1 | 7/2014 | Botes et al. |
| 2014/0193865 A1 | 7/2014 | Botes et al. |
| 2014/0194346 A1 | 7/2014 | Aebi et al. |
| 2014/0199306 A1 | 7/2014 | Ghosh et al. |
| 2014/0199737 A1 | 7/2014 | Botes et al. |
| 2014/0199742 A1 | 7/2014 | Shibamoto |
| 2014/0205538 A1 | 7/2014 | Wei et al. |
| 2014/0206064 A1 | 7/2014 | Bayer et al. |
| 2014/0206068 A1 | 7/2014 | Claes et al. |
| 2014/0206599 A1 | 7/2014 | Baumann et al. |
| 2014/0212396 A1 | 7/2014 | Newman |
| 2014/0212454 A1 | 7/2014 | Pasmans et al. |
| 2014/0212925 A1 | 7/2014 | Wu et al. |
| 2014/0219912 A1 | 8/2014 | Ghayur et al. |
| 2014/0220019 A1 | 8/2014 | Ghayur et al. |
| 2014/0220661 A1 | 8/2014 | Bermudes |
| 2014/0227286 A1 | 8/2014 | Jaffee et al. |
| 2014/0227291 A1 | 8/2014 | Barghorn et al. |
| 2014/0227294 A1 | 8/2014 | Anderson et al. |
| 2014/0227750 A1 | 8/2014 | Picataggio et al. |
| 2014/0234208 A1 | 8/2014 | Ghayur et al. |
| 2014/0234310 A1 | 8/2014 | Shapiro |
| 2014/0234363 A1 | 8/2014 | Masignani et al. |
| 2014/0242674 A1 | 8/2014 | Subbian et al. |
| 2014/0242704 A1 | 8/2014 | Zelder et al. |
| 2014/0248309 A1 | 9/2014 | Kopecko et al. |
| 2014/0248669 A1 | 9/2014 | Marliere |
| 2014/0248673 A1 | 9/2014 | Botes et al. |
| 2014/0255345 A1 | 9/2014 | Grabstein et al. |
| 2014/0255376 A1 | 9/2014 | Johnson et al. |
| 2014/0256922 A1 | 9/2014 | David et al. |
| 2014/0256960 A1 | 9/2014 | Takagi et al. |
| 2014/0271640 A1 | 9/2014 | Bowdish et al. |
| 2014/0273164 A1 | 9/2014 | Liao et al. |
| 2014/0273165 A1 | 9/2014 | Liao et al. |
| 2014/0287419 A1 | 9/2014 | Althoff et al. |
| 2014/0289906 A1 | 9/2014 | Althoff et al. |
| 2014/0294797 A1 | 10/2014 | Foster et al. |
| 2014/0294891 A1 | 10/2014 | Szalay et al. |
| 2014/0296480 A1 | 10/2014 | Sanchez Garcia et al. |
| 2014/0298499 A1 | 10/2014 | Gray et al. |
| 2014/0302078 A1 | 10/2014 | Masignani et al. |
| 2014/0302094 A1 | 10/2014 | Titball et al. |
| 2014/0308286 A1 | 10/2014 | Ghayur et al. |
| 2014/0322730 A1 | 10/2014 | Chapman et al. |
| 2014/0322779 A1 | 10/2014 | Burgard et al. |
| 2014/0322790 A1 | 10/2014 | Sebastian et al. |
| 2014/0328794 A1 | 11/2014 | Rosen et al. |
| 2014/0328849 A1 | 11/2014 | Reif et al. |
| 2014/0328875 A1 | 11/2014 | Garcia-Sastre et al. |
| 2014/0330032 A1 | 11/2014 | Lynch et al. |
| 2014/0335014 A1 | 11/2014 | Ghayur et al. |
| 2014/0335087 A1 | 11/2014 | Buechler et al. |
| 2014/0335564 A1 | 11/2014 | Hsieh et al. |
| 2014/0341943 A1 | 11/2014 | Rikihisa |
| 2014/0342405 A1 | 11/2014 | Rosen et al. |
| 2014/0342451 A1 | 11/2014 | Kwon et al. |
| 2014/0343267 A1 | 11/2014 | Hsieh et al. |
| 2014/0348817 A1 | 11/2014 | Jiang et al. |
| 2014/0348828 A1 | 11/2014 | Foster et al. |
| 2014/0356389 A1 | 12/2014 | Masignani et al. |
| 2014/0356916 A1 | 12/2014 | Wittmann et al. |
| 2014/0363847 A1 | 12/2014 | Fujii et al. |
| 2014/0369986 A1 | 12/2014 | Padmanabhan et al. |
| 2014/0370036 A1 | 12/2014 | Shapiro |
| 2014/0371194 A1 | 12/2014 | Seed et al. |
| 2014/0377752 A1 | 12/2014 | Lee et al. |

(56) References Cited

U.S. PATENT DOCUMENTS

| | | |
|---|---|---|
| 2014/0377858 A1 | 12/2014 | Wu et al. |
| 2014/0377860 A1 | 12/2014 | Wu et al. |
| 2014/0378372 A1 | 12/2014 | Mogelsvang et al. |
| 2015/0004665 A1 | 1/2015 | Chotani et al. |
| 2015/0004705 A1 | 1/2015 | Lu et al. |
| 2015/0010592 A1 | 1/2015 | Wacker et al. |
| 2015/0017095 A1 | 1/2015 | Ghayur et al. |
| 2015/0017138 A1 | 1/2015 | Fruehauf et al. |
| 2015/0017204 A1 | 1/2015 | Bermudes |
| 2015/0018522 A1 | 1/2015 | Qasba et al. |
| 2015/0030573 A1 | 1/2015 | Fruehauf et al. |
| 2015/0030584 A1 | 1/2015 | Rummel |
| 2015/0030624 A1 | 1/2015 | Armstrong et al. |
| 2015/0031658 A1 | 1/2015 | Seed et al. |
| 2015/0037860 A1 | 2/2015 | Botes et al. |
| 2015/0037861 A1 | 2/2015 | Beck et al. |
| 2015/0044243 A1 | 2/2015 | Wisniewski et al. |
| 2015/0044256 A1 | 2/2015 | Dattwyler et al. |
| 2015/0044722 A1 | 2/2015 | Tremblay et al. |
| 2015/0044755 A1 | 2/2015 | Yocum et al. |
| 2015/0045535 A1 | 2/2015 | Berka et al. |
| 2015/0050215 A1 | 2/2015 | Novak et al. |
| 2015/0050308 A1 | 2/2015 | van der Hoek |
| 2015/0056232 A1 | 2/2015 | Roy |
| 2015/0056651 A1 | 2/2015 | Lynch et al. |
| 2015/0056666 A1 | 2/2015 | Reth et al. |
| 2015/0056684 A1 | 2/2015 | Lipscomb et al. |
| 2015/0057191 A1 | 2/2015 | Tissot et al. |
| 2015/0071904 A1 | 3/2015 | Collins et al. |
| 2015/0071957 A1 | 3/2015 | Kelly et al. |
| 2015/0072384 A1 | 3/2015 | Lynch et al. |
| 2015/0079063 A1 | 3/2015 | Fima et al. |
| 2015/0079654 A1 | 3/2015 | Botes et al. |
| 2015/0086585 A1 | 3/2015 | Gin et al. |
| 2015/0087035 A1 | 3/2015 | Picataggio et al. |
| 2015/0093358 A1 | 4/2015 | Fares et al. |
| 2015/0093387 A1 | 4/2015 | Wu et al. |
| 2015/0098900 A1 | 4/2015 | Ebens et al. |
| 2015/0099707 A1 | 4/2015 | Pastan et al. |
| 2015/0104452 A1 | 4/2015 | Ghayur et al. |
| 2015/0104514 A1 | 4/2015 | Kaplan et al. |
| 2015/0110720 A1 | 4/2015 | Markiv et al. |
| 2015/0110836 A1 | 4/2015 | Glanville |
| 2015/0111262 A1 | 4/2015 | Botes et al. |
| 2015/0112652 A1 | 4/2015 | Palsson |
| 2015/0119354 A1 | 4/2015 | Kahne et al. |
| 2015/0125849 A1 | 5/2015 | Yeh et al. |
| 2015/0126445 A1 | 5/2015 | Fares et al. |
| 2015/0132218 A1 | 5/2015 | Asundi et al. |
| 2015/0132330 A1 | 5/2015 | Garcia-Sastre et al. |
| 2015/0132368 A1 | 5/2015 | Muro Galindo et al. |
| 2015/0133375 A1 | 5/2015 | Mogelsvang et al. |
| 2015/0139940 A1 | 5/2015 | Bermudez Humaran et al. |
| 2015/0140614 A1 | 5/2015 | Reth et al. |
| 2015/0141331 A1 | 5/2015 | Fares et al. |
| 2015/0141622 A1 | 5/2015 | Alitalo et al. |
| 2015/0147343 A1 | 5/2015 | Nitsch et al. |
| 2015/0148291 A1 | 5/2015 | Fima et al. |
| 2015/0150959 A1 | 6/2015 | Watnick |
| 2015/0152161 A1 | 6/2015 | Reiter et al. |
| 2015/0153325 A1 | 6/2015 | McNutt et al. |
| 2015/0153358 A1 | 6/2015 | Ayuso et al. |
| 2015/0166594 A1 | 6/2015 | Kahne et al. |
| 2015/0166661 A1 | 6/2015 | Chen et al. |
| 2015/0166972 A1 | 6/2015 | Dong et al. |
| 2015/0166975 A1 | 6/2015 | Prakash et al. |
| 2015/0183867 A1 | 7/2015 | Ghayur et al. |
| 2015/0184220 A1 | 7/2015 | Sebastian et al. |
| 2015/0190496 A1 | 7/2015 | Hargis et al. |
| 2015/0191691 A1 | 7/2015 | Bisanz et al. |
| 2015/0197748 A1 | 7/2015 | Liu et al. |
| 2015/0197775 A1 | 7/2015 | Iida et al. |
| 2015/0202284 A1 | 7/2015 | Dimitrov |
| 2015/0203557 A1 | 7/2015 | Debinski et al. |
| 2015/0203578 A1 | 7/2015 | Bebbington et al. |
| 2015/0203835 A1 | 7/2015 | Nunn, Jr. et al. |
| 2015/0203854 A1 | 7/2015 | Williams et al. |
| 2015/0211031 A1 | 7/2015 | Lee et al. |
| 2015/0216954 A1 | 8/2015 | Bottje et al. |
| 2015/0216965 A1 | 8/2015 | Diamond et al. |
| 2015/0218231 A1 | 8/2015 | Bakaletz et al. |
| 2015/0218254 A1 | 8/2015 | Sabbadini et al. |
| 2015/0218261 A1 | 8/2015 | Barghorn et al. |
| 2015/0218544 A9 | 8/2015 | Jiang et al. |
| 2015/0218590 A1 | 8/2015 | Mcauliffe et al. |
| 2015/0225692 A1 | 8/2015 | Bhatia et al. |
| 2015/0225732 A1 | 8/2015 | Williams et al. |
| 2015/0225744 A1 | 8/2015 | Beck et al. |
| 2015/0231207 A1 | 8/2015 | Kaspar |
| 2015/0232550 A1 | 8/2015 | Ghayur et al. |
| 2015/0232557 A1 | 8/2015 | Tan et al. |
| 2015/0232861 A1 | 8/2015 | Delisa et al. |
| 2015/0232903 A1 | 8/2015 | HIidesaki et al. |
| 2015/0240226 A1 | 8/2015 | Mathur et al. |
| 2015/0246137 A1 | 9/2015 | Guo et al. |
| 2015/0247172 A1 | 9/2015 | Herrema |
| 2015/0252097 A1 | 9/2015 | Camphausen et al. |
| 2015/0258209 A1 | 9/2015 | Benz et al. |
| 2015/0259389 A9 | 9/2015 | Berka et al. |
| 2015/0259418 A1 | 9/2015 | Barth et al. |
| 2015/0266939 A1 | 9/2015 | Vogan et al. |
| 2015/0266977 A1 | 9/2015 | Hsieh et al. |
| 2015/0267211 A1 | 9/2015 | Botes et al. |
| 2015/0273045 A1 | 10/2015 | Kolander et al. |
| 2015/0273048 A1 | 10/2015 | Kang et al. |
| 2015/0275241 A1 | 10/2015 | Herrema |
| 2015/0275242 A1 | 10/2015 | Osterhout et al. |
| 2015/0284467 A1 | 10/2015 | Lipp et al. |
| 2015/0284760 A1 | 10/2015 | Schendzielorz et al. |
| 2015/0291667 A1 | 10/2015 | Dirienzo |
| 2015/0307560 A1 | 10/2015 | DeLisa et al. |
| 2015/0307576 A1 | 10/2015 | Bowdish et al. |
| 2015/0307854 A1 | 10/2015 | Botes et al. |
| 2015/0315283 A1 | 11/2015 | Ghayur et al. |
| 2015/0329619 A1 | 11/2015 | Rosen et al. |
| 2015/0329644 A1 | 11/2015 | Shi et al. |
| 2015/0329882 A1 | 11/2015 | Lee et al. |
| 2015/0335729 A1 | 11/2015 | Garcia-Sastre et al. |
| 2015/0337053 A1 | 11/2015 | McCarthy et al. |
| 2015/0337320 A1 | 11/2015 | Devroe et al. |
| 2015/0337321 A1 | 11/2015 | Mach et al. |
| 2015/0337340 A1 | 11/2015 | Alvizo et al. |
| 2015/0344529 A1 | 12/2015 | Yonemura et al. |
| 2015/0344838 A1 | 12/2015 | Campbell et al. |
| 2015/0344862 A1 | 12/2015 | Schellenberger et al. |
| 2015/0344894 A1 | 12/2015 | Giacalone et al. |
| 2015/0344916 A1 | 12/2015 | Lynch et al. |
| 2015/0351390 A1 | 12/2015 | Castle et al. |
| 2015/0353911 A1 | 12/2015 | Salas et al. |
| 2015/0355172 A1 | 12/2015 | Kraus et al. |
| 2015/0361141 A1 | 12/2015 | Buttigieg et al. |
| 2015/0361458 A1 | 12/2015 | Botes et al. |
| 2015/0361459 A1 | 12/2015 | Botes et al. |
| 2015/0361460 A1 | 12/2015 | Botes et al. |
| 2015/0361462 A1 | 12/2015 | Botes et al. |
| 2015/0361463 A1 | 12/2015 | Botes et al. |
| 2015/0361464 A1 | 12/2015 | Botes et al. |
| 2015/0361465 A1 | 12/2015 | Botes et al. |
| 2015/0361466 A1 | 12/2015 | Botes et al. |
| 2015/0361467 A1 | 12/2015 | Botes et al. |
| 2015/0361468 A1 | 12/2015 | Botes et al. |
| 2015/0362482 A1 | 12/2015 | McNutt et al. |
| 2015/0366889 A1 | 12/2015 | Brynildsen et al. |
| 2015/0368630 A9 | 12/2015 | Fima et al. |
| 2016/0002672 A1 | 1/2016 | Beck et al. |
| 2016/0010132 A1 | 1/2016 | Subbian et al. |
| 2016/0017310 A1 | 1/2016 | Nunn, Jr. et al. |
| 2016/0017339 A1 | 1/2016 | Liao et al. |
| 2016/0024157 A1 | 1/2016 | Masignani et al. |
| 2016/0032323 A1 | 2/2016 | Beck et al. |
| 2016/0038581 A1 | 2/2016 | Bielke et al. |
| 2016/0040139 A1 | 2/2016 | Zhang et al. |
| 2016/0046675 A1 | 2/2016 | Kwong et al. |
| 2016/0058017 A1 | 3/2016 | Lira et al. |

(56)         References Cited

U.S. PATENT DOCUMENTS

| | | |
|---|---|---|
| 2016/0060306 A1 | 3/2016 | Lira et al. |
| 2016/0060635 A1 | 3/2016 | Liao et al. |
| 2016/0060663 A1 | 3/2016 | Grammann et al. |
| 2016/0068831 A1 | 3/2016 | Beck et al. |
| 2016/0068882 A1 | 3/2016 | Zhang et al. |
| 2016/0097064 A1 | 4/2016 | Zhang et al. |
| 2016/0101168 A1 | 4/2016 | Husseiny Elsayed et al. |
| 2016/0106853 A1 | 4/2016 | Hansel et al. |
| 2016/0114025 A1 | 4/2016 | Bottje et al. |
| 2016/0122399 A1 | 5/2016 | Frey et al. |
| 2016/0130618 A1 | 5/2016 | Hara et al. |
| 2016/0138052 A1 | 5/2016 | Mordaka |
| 2016/0145657 A1 | 5/2016 | Botes et al. |
| 2016/0152957 A1 | 6/2016 | Botes et al. |
| 2016/0153012 A1 | 6/2016 | Marliere |
| 2016/0160245 A1 | 6/2016 | Yocum et al. |
| 2016/0160255 A1 | 6/2016 | Botes et al. |
| 2016/0168610 A1 | 6/2016 | Conradie et al. |
| 2016/0199328 A1 | 7/2016 | Collins et al. |
| 2016/0201097 A1 | 7/2016 | Botes et al. |
| 2016/0222362 A1 | 8/2016 | Zhang et al. |
| 2016/0222393 A1 | 8/2016 | Bermudes |
| 2016/0222420 A1 | 8/2016 | Botes et al. |
| 2016/0222425 A1 | 8/2016 | Botes et al. |
| 2016/0237452 A1 | 8/2016 | Meade et al. |
| 2016/0243210 A1 | 8/2016 | O'Brien et al. |
| 2016/0244489 A1 | 8/2016 | Masignani et al. |
| 2016/0244769 A1 | 8/2016 | Xia et al. |
| 2016/0251633 A1 | 9/2016 | Muramatsu et al. |
| 2016/0257975 A1 | 9/2016 | Lynch et al. |
| 2016/0272950 A1 | 9/2016 | Corthals et al. |
| 2016/0289278 A1 | 10/2016 | Bakaletz et al. |
| 2016/0289632 A1 | 10/2016 | Gerke et al. |
| 2016/0289776 A1 | 10/2016 | Eggeling et al. |
| 2016/0355803 A1 | 12/2016 | Poma et al. |
| 2016/0361429 A1 | 12/2016 | Johnson et al. |
| 2016/0369257 A1 | 12/2016 | Foster et al. |
| 2017/0029844 A1 | 2/2017 | Ball et al. |
| 2017/0049866 A1 | 2/2017 | Sanders |
| 2017/0051260 A1 | 2/2017 | Bermudes et al. |
| 2017/0157239 A1 | 6/2017 | Bermudes |
| 2017/0204407 A1 | 7/2017 | Gilbert et al. |
| 2017/0226496 A1 | 8/2017 | Dong et al. |
| 2017/0283450 A1 | 10/2017 | Gin et al. |
| 2017/0298381 A1 | 10/2017 | Narva et al. |
| 2017/0369538 A1 | 12/2017 | Hey et al. |
| 2017/0369539 A1 | 12/2017 | Sheets et al. |
| 2018/0002394 A1 | 1/2018 | Debinski et al. |
| 2018/0127734 A1 | 5/2018 | Pavlik et al. |
| 2018/0127771 A1 | 5/2018 | Bonning et al. |
| 2018/0208631 A1 | 7/2018 | Baum et al. |
| 2018/0244760 A1 | 8/2018 | Feng et al. |
| 2018/0271787 A1 | 9/2018 | Tardi et al. |
| 2018/0291395 A1 | 10/2018 | Bowen et al. |
| 2018/0319872 A1 | 11/2018 | Feng et al. |
| 2018/0362951 A1 | 12/2018 | Foster et al. |
| 2019/0017057 A1 | 1/2019 | Bermudes |
| 2019/0136216 A1 | 5/2019 | Dong et al. |
| 2019/0153057 A1 | 5/2019 | Debinski et al. |
| 2019/0153418 A1 | 5/2019 | Dong et al. |
| 2019/0183986 A1 | 6/2019 | Sanders |
| 2019/0239513 A1 | 8/2019 | Bonning et al. |
| 2019/0256834 A1 | 8/2019 | Dong et al. |
| 2019/0300869 A1 | 10/2019 | Dong et al. |
| 2019/0376079 A1 | 12/2019 | Brummelkamp et al. |

* cited by examiner

CHIMERIC PROTEIN TOXINS FOR EXPRESSION BY THERAPEUTIC BACTERIA

CROSS REFERENCE TO RELATED APPLICATIONS

The present application is Continuation of U.S. patent application Ser. No. 15/835,093, filed Dec. 7, 2017, now U.S. Pat. No. 11,129,906, issued Sep. 28, 2021, which is a Non-provisional of, and claims benefit of priority from U.S. Provisional Patent Application Ser. No. 62/431,201, filed Dec. 7, 2016, the entirety of which is expressly incorporated herein by reference.

STATEMENT OF GOVERNMENT RIGHTS

This invention was made with government support under 1SC3GM098207 awarded by The National Institutes of Health. The government has certain rights in the invention.

BACKGROUND

Field of the Invention

This invention is generally in the field of therapeutic delivery systems including bacteria, and systems and methods for providing chimeric proteins efficiently targeted to cancer cells.

Description of the Prior Art

Citation or identification of any reference herein, or any section of this application shall not be construed as an admission that such reference is available as prior art to the present application. The disclosures of each of these publications and patents are hereby incorporated by reference in their entirety in this application, and shall be treated as if the entirety thereof forms a part of this application.

Tumor-targeted bacteria offer tremendous potential advantages for the treatment of solid tumors, including the targeting from a distant inoculation site and the ability to express therapeutic agents directly within the tumor (Pawelek et al., 1997, Tumor-targeted *Salmonella* as a novel anticancer agent, Cancer Research 57:4537-4544; Low et al., 1999, Lipid A mutant *salmonella* with suppressed virulence and TNF-alpha induction retain tumor-targeting in vivo, Nature Biotechnol. 17:37-41). However, the primary shortcoming of tumor-targeted bacteria investigated in the human clinical trials (*Salmonella* strain VNP20009 and its derivative TAPET-CD; Toso et al., 2002, Phase I study of the intravenous administration of attenuated *Salmonella typhimurium* to patients with metastatic melanoma, J. Clin, Oncol. 20:142-152; Meir et al., 2001, Phase 1 trial of a live, attenuated *Salmonella typhimurium* (VNP20009) administered by direct Intra-tumoral (IT) injection, Proc Am Soc Clin Oncol 20: abstr 1043); Nemunaitis et al., 2003, Pilot trial of genetically modified, attenuated *Salmonella* expressing the *E. coli* cytosine deaminase gene in refractory cancer patients, Cancer Gene Therapy 10:737-744) is that no significant antitumor activity has been observed, even in patients where the bacteria was documented to target the tumor. One method of increasing the ability of the bacteria to kill tumor cells is to engineer the bacteria to express conventional bacterial toxins (e.g., WO 2009/126189, WO 03/014380, WO/2005/018332, WO/2008/073148, US 2003/0059400 U.S. Pat. Nos. 7,452,531, 7,354,592, 6,962,696, 6,923,972, 6,863,894, 6,685,935, 6,475,482, 6,447,784, 6,190,657 and 6,080,849, 8,241,623, 8,524,220 8,771,669, 8,524,220, each of which is expressly incorporated herein by reference).

Use of protein toxins for treatment of various disorders including inflammation, autoimmunity, neurological disorders and cancer has long-suffered from off-target toxicity. Enhancing toxin specificity, which offers the potential to eliminate side effect, has been achieved by several different means, such as attachment of a specific antibodies or peptide ligand (e.g., *Pseudomonas* exotoxin A (PE-ToxA) antibody conjugate, known as an immunotoxin), or a ligand targeted to a surface molecule of the target cell. Based upon the binding specificity of the attached antibody or ligand moiety for a specific target, enhanced specificity of the target is achieved (Quintero et al., 2016. EGFR-targeted chimeras of *Pseudomonas* Tox A released into the extracellular milieu by attenuated *Salmonella* selectively kill tumor cells. Biotechnology and Bioengineering 113:2698-2711).

Other toxins have been engineered to achieve specificity based upon their sight of activation. For example, proaerolysin requires proteolytic activation to become the cytotoxic protein acrolysin. Substitution of the natural protease cleavage site for a tumor-specific protease cleavage site (e.g., that of the prostate specific antigen (PSA) protease or urokinase) results in a toxin selectively activated within tumors (Denmeade et al. WO 03/018611 and Denmeade et al. U.S. Pat. No. 7,635,682), specifically incorporated by reference herein. Another similar activation system has utilized ubiquitin fusion, coupled with a hydrolysable tumor protease (e.g., PSA) sequence and a toxin (e.g., saporin), as described by Tschrniuk et al. 2005 (Construction of tumor-specific toxins using ubiquitin fusion technique, Molecular Therapy 11:196-204), also specifically incorporated by reference herein. However, while some specificity is engendered and thus these activated protein types are useful in the present technology as modified herein, in these types of engineered toxins, off-target toxicity can occur. In the case of the *Pseudomonas* immunotoxin, several dose-limiting toxicities have been identified. Vascular leakage syndrome (VLS) is associated with hypoalbuminemia, edema, weight gain, hypotension and occasional dyspnea, which is suggested to occur by immunotoxin-mediated endothelial cell injury (Baluna et al., 2000, Exp. Cell Res. 258:417-424), resulting in a dose-limiting toxicity. Renal injury has occurred in some patients treated with immunotoxins, which may be due to micro-aggregates of the immunotoxin (Frankel et al., 2001, Blood 98: 722a). Liver damage from immunotoxins is a frequent occurrence that is believed to be multifactorial (Frankel, 2002, Clinical Cancer Research 8:942-944). To date, antibodies linked to proteinaceous toxins have limited success clinically.

Recently developed approaches to delivery of therapeutic molecules (U.S. Pat. Nos. 8,241,623; 8,524,220; 8,771,669; and 8,524,220) have coupled a protease sensitive therapeutic molecule with co-expression of protease inhibitors, expressly incorporated by reference herein.

Use of secreted proteins in live bacterial vectors has been demonstrated by several authors. Holland et al. (U.S. Pat. No. 5,143,830) have illustrated the use of fusions with the C-terminal portion of the hemolysin A (hlyA) gene, a member of the type I secretion system. When co-expressed in the presence of the hemolysin protein secretion channel (hlyBD) and a functional TolC, heterologous fusions are readily secreted from the bacteria. The type I secretion system that has been utilized most widely, and although it is currently considered the best system available, is thought to have limitations for delivery by attenuated bacteria (Hahn and Specht, 2003, FEMS Immunology and Medical Micro-biology, 37:87-98). Those limitations include the amount of protein secreted and the ability of the protein fused to it to interfere with secretion. Improvements of the type I secre-tion system have been demonstrated by Sugamata and Shiba (2005 Applied and Environmental Microbiology 71:656-662) using a modified hlyB, and by Gupta and Lee (2008 Biotechnology and Bioengineering, 101:967-974) by addi-tion of rare codons to the hlyA gene, each of which is expressly incorporated by reference in their entirety herein. Fusion to the gene ClyA (Galen et al., 2004, Infection and Immunity, 72:7096-7106 and Type III secretion proteins have also been used. Surface display has been used to export proteins outside of the bacteria. For example, fusion of the Lpp protein amino acids 1-9 with the transmembrane region B3-B7 of OmpA has been used for surface display (Samu-elson et al., 2002, Display of proteins on bacteria, J. Bio-technology 96:129-154, expressly incorporated by reference in its entirety herein). The autotransporter surface display has been described by Berthet et al., WO/2002/070645, expressly incorporated by reference herein. Other heterolo-gous protein secretion systems utilizing the autotransporter family can be modulated to result in either surface display or complete release into the medium (see Henderson et al., 2004, Type V secretion pathway: the autotransporter story, Microbiology and Molecular Biology Reviews 68:692-744; Jose, 2006 Applied Microbiol. Biotechnol. 69:607-614; Jose J, Zangen D (2005) Autodisplay of the protease inhibitor aprotinin in *Escherichia coli.* Biochem Biophys Res Com-mun 333:1218-1226 and Rutherford and Mourez 2006 Microbial Cell Factories 5:22). For example, Veiga et al. (2003 Journal of Bacteriology 185:5585-5590 and Klauser et al., 1990 EMBO Journal 9:1991-1999) demonstrated hybrid proteins containing the β-autotransporter domain of the immunoglobulin A (IgA) protease of Nisseria gonorrhea. Fusions to flagellar proteins have been demonstrated. The peptide, usually of 15 to 36 amino acids in length, is inserted into the central, hypervariable region of the FliC gene such as that from *Salmonella muenchen* (Verma et al. 1995 Vaccine 13:235-24; Wu et al., 1989 Proc. Natl. Acad. Sci. USA 86:4726-4730; Cuadro et al., 2004 Infect. Immun. 72:2810-2816; Newton et al., 1995, Res. Microbiol. 146: 203-216, expressly incorporated by reference in their entirety herein). Multihybrid FliC insertions of up to 302 amino acids have also been prepared (Tanskanen et al. 2000, Appl. Env. Microbiol. 66:4152-4156, expressly incorporated by reference in its entirety herein). Trimerization of antigens can be achieved using the T4 fibritin foldon trimerization sequence (Wei et al. 2008 J. Virology 82:6200-6208) and VASP tetramerization domains (Kühnel et al., 2004 PNAS 101:17027-17032), expressly incorporated by reference in their entirety herein. The multimerization domains are used to create, bi-specific, tri-specific, and quatra-specific target-ing agents, whereby each individual agent is expressed with a multimerization tag, each of which may have the same or separate targeting peptide, such that following expression, surface display, secretion and/or release, they form multim-ers with multiple targeting domains.

SUMMARY OF THE INVENTION

Modified Therapeutic Molecules

The present technology, according to various embodi-ments, consists of known and/or novel chimeric proteins, or combinations of proteins, that are expressed, secreted, sur-face displayed and/or released by bacteria and result in anticancer activity or have direct inhibitory or cytotoxic anti-neoplastic activity, including activity against cancer stem cells and/or cancer mesenchymal stromal cells, and may optionally include the combination with secreted pro-tease inhibitors. The bacterial delivery vector may be attenu-ated, non-pathogenic, low pathogenic (including wild type), or a probiotic bacterium. The bacteria are introduced either systemically (e.g., parentral, intravenous (IV), intramuscular (IM), intralymphatic (IL), intradermal (ID), subcutaneously (sub-q), local-regionally (e.g., intralesionally, intratumorally (IT), intrapacritoneally (IP), topically, intrathecally (intrath-ecal), by inhaler or nasal spray) or to the mucosal system through oral, nasal, pulmonary intravessically, enema or suppository administration where they are able to undergo limited replication, express, surface display, secrete and/or release the anti-cancer inhibitory proteins or a combination thereof, and thereby provide a therapeutic benefit by reduc-ing or eliminating the disease, malignancy and/or neoplasia.

The present technology, according to various embodi-ments, further consists of modified forms of toxins with improved secretion, surface display and/or release by the bacteria, and/or modifications that improve the overall activ-ity and/or specificity of the toxin. Such toxins may be further co-expressed with protease inhibitors as previously described (See, U.S. Pat. Nos. 8,241,623; 8,524,220; 8,771, 669; 8,524,220).

Toxins, therapeutic cytokines and other molecules, homo-logues or fragments thereof useful in conjunction with the present technology, according to various embodiments, includes small lytic peptides, larger lytic peptides, pore-forming toxins, protein inhibitors, extracellular DNAases (DNase), intracellular DNAases, apoptosis inducing pep-tides, cytokines, prodrug converting enzymes, metabolite destroying enzymes, ribonucleases, antibody inactivating toxins and other anticancer peptides. In a preferred embodi-ment, the toxins include those that are naturally secreted, released and/or surface displayed, or heterologously secreted, released and/or surface displayed, and that can be modified uniquely to suit the delivery by a bacterium and may be further engineered to have the tumor, lymphoma, leukemic bone marrow or proximity-selective targeting sys-tem described herein, including but not limited to the proteins azurin, carboxyesterase Est55 (a prodrug-convert-ing enzyme from *Geobacillus* that activates CPT-11 to SN-38), thiaminase (e.g., from *Bacillus*), methionase (me-thioninase), asparaginase, tryptophanase, apoptin, Torquetnovirus (TTV) derived apoptosis-inducing protein TAIP and with gyrovirus VP3 bax, bim, p53, BAK, BH3 peptide (BCL2 homology domain 3), cytochrome C, throm-bospondin, platlet factor 4 (PF4) peptide, *Bacillus* sp. cytolysins, *Bacillus* sp. nheABC toxins, cytolethal distend-ing toxins (cldt) including those cldts from *Haemophilus, Aggregatibacter, Salmonella, Escherichia, Shigella, Campy-lobacter, Helicobacter, Hahella* and *Yersinia,* typhoid toxins (including pertussis like toxins; pltAB), pertussis toxin, cldt:plt hybrids, actAB, cytotoxic nectrotic factor (cnf), dermonecrotic factor (dnf), shiga toxins and shiga-like tox-ins, bacteriocins, (colicins and microcins; Hen and Jack, Chapter 13 Microcins, in Kastin (ed), 2006, Handbook of Biologically Active Peptides, Academic Press; Nes et al., Chapter 17, The nonlantibiotic heat-stable bacteriocins in gram-positive bacteria, in Kastin (ed), 2006, Handbook of Biologically Active Peptides, Academic Press; Sharma et al., Chapter 18 in Kastin (ed), 2006, Handbook of Biologically Active Peptides, Academic Press) including membrane depolarizing (or pore-forming), DNAases (including colicin DNase, Staphylococcal Nuclease A:OmpA fusions (Taka-hara et al., 1985 J. Biol. Chem 260:2670-2674), *Serratia*

*marcescens* DNase (Clegg and Allen, 1985, FEMS Microbiology Letters 27:257-262; *Vibrio* DNase Newland et al., 1985 Infect Immun 47:691-696) or other bacterial DNase), RNAases, and tRNAases, including but not limited to colicin A, colicin D, colicin E5, colicin E492, microcin M24, colE1, colE2, colE3, colE5 colE7, coleE8, colE9, col-Ia, colicin N and colicin B, membrane lytic peptides from *Staphalococcus* (listed below) and sea anemones, P15 peptide and other TGF-beta mimics, repeat in toxin (RTX) family members (together with the necessary acylation and secretion genes) including *Actinobacillus* leucotoxins, a leuckotoxin: *E. coli* HlyA hybrid, *E. coli* HlyA hemolysin, *Bordetella* adenylate cyclase toxin, heat stable enterotoxins from *E. coli* and *Vibrio* sp. (Dubreuil 2006, Chapter 48, *Escherichia coli, Vibrio* and *Yersinia* species heat stable enterotoxins, Alouf and Popoff (eds), 2006, Comprehensive Sourcebook of Bacterial Protein Toxins, Third Edition, Academic Press), autotransporter toxins including but not limited to IgA protease, picU espC, and sat, *Staphalococcus* protein A, chlostridium enterotoxin, *Clostridium difficile* toxin A, scorpion chlorotoxin, aerolysin, subtilase, cercolysin, *Staphalococcus* leukotoxins (e.g. LukF-PV, LukF-R, LukF-I, LukM, HlgB) and the other, to class S (e.g. LukS-PV, LukS-R, LukS-I, HlgA, HlgC). Best known are the toxins produced by *S. aureus*: γ-hacmolysins, HlgA/HlgB and HlgC/HlgB and leukocidin Panton-Valentine, LukS-PV/LukF-PV (Luk-PV, PVL)) TRAIL, fasL, IL-18, CCL-21, human cyokine LIGHT, agglutinins (*Maackia amurensis*, wheat germ, *Datura stramonium, Lycopersicon* (tomato) plant lectin, leukoagglutinin (L-PHA, *Helix pomatia*) saporin, ricin, pertussus toxin, and porB, as well as other toxins and peptides (Kastin (ed), 2006, Handbook of Biologically Active Peptides, Academic Press; Alouf and Popoff (eds), 2006, Comprehensive Sourcebook of Bacterial Protein Toxins, Third Edition, Academic Press; each of which is expressly incorporated by reference in their entirety herein). Metabolite toxins such as the *Chromobacterium violacium* dipsepeptides (Shigeatsu et al., 1994, FR901228, a novel antitumor bicyclic depsipeptide produced by *Chromobacterium violaceum* No. 968. II. Structure determination. J Antibiot (Tokyo) 47 (3): 311-4) or those from *Serratia* are also of use in the present technology.

The chimeras may be further modified by addition of one or more multimerization domains, such as the T4 foldon trimerization domain (Meier et al., 2004, Journal of Molecular Biology, 344:1051-1069; Bhardwaj et al., Protein Sci. 2008 17:1475-1485) or tetramerization domains such as VASP (Kühnel et al., 2004 PNAS 101:17027-17032). Chimeric toxins may be further modified by the addition of known cell penetrating (ferry) peptide which further improves their entry into target cells. Cell penetrating peptides include those derived from the human immunodifficency virus (HIV) TAT protein amino acids 47-57 (YGRKKRRQRRR SEQ ID NO: 001) and used in fusion proteins (e.g., TAT-apoptin, TAT-bim, TAT-p53), the antennapedia homeodomain (penetraxin), Kaposi fibroblast growth factor (FGF) membrane-translocating sequence (MTS), herpes simplex virus VP22, hexahistidine, hexylysine, hexaarginine or "Chariot" (Active Motif, Carlsbad, Calif.; U.S. Pat. No. 6,841,535). Nuclear localization signals (NLSs) may also be added, including but not limited to that from herpes simplex virus thymidine kinase, the SV40 large T antigen monopartite NLS, or the nucleoplamin bipartite NLS or more preferably, the NLS from apoptin, a tumor associated (tumor-selective) NLS. The tumor-selective nuclear export signal from apoptin may be used alone or together with NLS from apoptin (Heckl et al., 2008, Value of apoptin's 40-amino-acid C-terminal fragment for the differentiation between human tumor and non-tumor cells, Apoptosis 13:495-508; Backendor et al., 2008, Apoptin: Therapeutic potential of an early sensor of carcinogenic transformation, Ann Rev Pharmacol Toxicol 48:143-69).

Regarding use of tumor-targeted bacteria expressing wild type cytolethal distending toxin and chimeras including those with apoptin, there have been several earlier descriptions (U.S. Pat. Nos. 6,962,696; 7,452,531; 8,241,623; 8,524,220; 8,623,350; 8,771,669). Cytolethal distending toxins (CLDTs) comprise a family of heterotrimeric holotoxins produced by bacteria that are internalized into mammalian cells and translocated into the nucleus. CLDTs are known to occur in a number of bacterial genera including *Haemophilus, Aggregatibacter, Salmonella, Escherichia, Shigella, Campylobacter, Helicobacter*, Hahella and *Yersinia* (Gargi et al., 2012 Bacterial toxin modulation of the eukaryotic cell cycle: are all cytolethal distending toxins created equally? Frontiers in Cellular and Infection Microbiol. 2:124. doi: 10.3389/fcimb.2012.00124), however CLDT does not exist in the VNP20009 strain of *Salmonella* used in human clinical studies (Toso et al. 2002. Phase I Study of the Intravenous Administration of Attenuated *Salmonella typhimurium* to Patients With Metastatic Melanoma. J. Clin. Oncol. 20, 142-152; Low et al., 2004, Construction of VNP20009, a novel, genetically stable antibiotic sensitive strain of tumor-targeting *Salmonella* for parenteral administration in humans. Methods Mol Med 90:47-60).

Depending upon both the specific CLDT and the mammalian cells type, different effects have been documented. All CLDTs have homology to exonuclease III and several have been directly shown to exhibit DNase activity in vitro (Ewell and Dreyfus 2000 DNase I homologous residues in CdtB are critical for cytolethal distending toxin-mediated cell cycle arrest. Mol Microbiol 37, 952-963; Lara-Tejero and Galán, 2000 A bacterial toxin that controls cell cycle progression as a deoxyribonuclease I-like protein. Science 290, 354-357), which is believed to be the primary effect of the toxin. The DNase activity results in double-stranded DNA breaks that activates the cell's DNA damage response and interrupts the cell cycle at G2M. Non-haematopoctic cells tend to enlarge, hence part of the toxin name distending, and in many cases the cells subsequently undergo apoptosis. In haematopoitic cells apoptosis is more rapidly produced (Jinadasa et al., 2011, Cytolethal distending toxin: a conserved bacterial genotoxin that blocks cell cycle progression, leading to apoptosis of a broad range of mammalian cell lineages. Microbiology 157:1851-1875; Gargi et al., 2012).

Most of the CLDTs are organized in a unidirectional operon of cldtA, cldtB and cldtC genes, where the cldtB encodes the active subcomponent, and cldtA and cldtC encode peptides that are involved in cell binding and translocation. In *Salmonella* however, the genes exist as a bidirectional operon consisting of eldtB together with a two pertussis like toxin subunits oriented in the opposite direction, pltA and pltB, as well as sty and ttsA, also in opposing directions of each other, that are reported to be required for secretion of the toxin (Hodak and Galan 2013 A *Salmonella Typhi* homologue of bacteriophage muramidase controls typhoid toxin secretion. EMBO Reports 14:95-102).

Translocation of *E. coli* CLDTs to the nucleus, which constitutes the target location for the endonuclease activity, requires the presence of a nuclear localization signal (NLS). In *Escherichia coli* CLDT-II for example, the NLS is bipartite and located at the C-terminus (McSweeney and Dreyfus, 2004). Nishikubo et al., 2003 identified an NLS occurring in the 48-124 amino acid region in *Actinobacillus actinomy-cetemcomitans.*

Apoptins are a family of viral genes that were first discovered in chicken anemia virus. Apoptin is the product of the VP3 gene that is involved in lymphoidal atropy and anemia in infected chickens (Peñaloza et al., 2014 Apoptins: selective anticancer agents, Trends in Molecular Medicine 20:519-528; Los et al., 2009 Apoptin, a tumor selective killer, Biochimica et Biophysica Acta 1793:1335-1342). Apoptin was subsequently found to selectively induce apoptosis in cancer cells (Danen-Van Oorschot et al., 1997 Apoptin induces apoptosis in human transformed and malignant cells but not in normal cells. Proc. Natl. Acad. Sci. USA 94:5843-5847). Apoptin shares similarity with Torquetno-virus (TTV) derived apoptosis-inducing protein TAIP and with gyrovirus VP3. Apoptin consists of several different domains including a leucine rich sequence (LRS) which is involved in binding to the promyelocytic leukemia (PML) protein of nuclei and in apoptin multimerization, an SRC homology 3 (SH3) binding domain with is part of a bipartite nuclear localization signal (NLS), a nuclear export sequence (NES) that promotes egress of apoptin from normal cell nuclei, a set of threonines of which T108 must be phosphorylated for full apoptin activity, the C-terminal portion of the bipartite NLS and an anaphase promoting complex/cyclosome 1 (APC/CI) binding domain that consists of approximately one third of the C-terminus.

The present technology, according to various embodiments, consists of a modified *Salmonella* CLDT operon and forms of cytolethal distending toxins that are chimeric with apoptin and other peptide moieties including peptide linkers that improve activity and peptide blocking moieties that must be specifically cleaved to activate the protein. The present technology, according to various embodiments, uses deletions in the CLDT nuclear localization signals which are then complemented by C-terminal fusions with apoptin, or apoptin fragments, which supply its nuclear localization signal in trans as a fusion peptide, terminated with a cysteine.

The types of cancers or neoplasias to which the present technology is directed include all neoplastic malignancies, including solid tumors such as those of colon, lung, breast, prostate, sarcomas, carcinomas, head and neck tumors, melanoma, as well as hematological, non-solid or diffuse cancers such as leukemia and lymphomas, myelodysplastic cells, plasma cell myeloma, plasmacytomas, and multiple myelomas. Specific types of cancers include acute lymphoblastic leukemia, acute myeloid leukemia, adrenocortical carcinoma adrenocortical carcinoma, adult (primary) liver cancer, adult acute myeloid leukemia, AIDS-related cancers, AIDS-related lymphoma, anal cancer, appendix cancer, astrocytomas, astrocytomas (childhood), basal cell carcinoma, bile duct cancer, bladder cancer, bone cancer, brain stem glioma, brain tumor, breast cancer (female), breast cancer (male), bronchial tumors, Burkitt's lymphoma, carcinoid tumor, carcinoma of unknown primary site, central nervous system atypical teratoid/rhabdoid tumor, central nervous system embryonal tumors, central nervous system lymphoma, central nervous system tumors, cervical cancer, childhood acute myeloma, childhood multiple myeloma/plasma cell neoplasm, chordoma, chronic lymphocytic leukemia, chronic myelogenous leukemia, chronic myeloid leukemia, chronic myeloproliferative disorders, colon cancer, colorectal cancer, craniopharyngioma, cutaneous T-cell lymphoma, embryonal tumors, endometrial cancer, endometrial uterine sarcoma, ependymoblastoma, ependymoma, esophageal cancer, Ewing sarcoma family of tumors, extracranial germ cell tumor, extragonadal germ cell tumor, extrahepatic bile duct cancer, extrahepatic gallbladder cancer, eye cancer, gallbladder cancer, gastric (stomach) cancer, gastrointestinal carcinoma, gastrointestinal carcinoid tumor, gastrointestinal stromal cell tumor, gastrointestinal stromal tumor (gist), germ cell tumor, glioma, hairy cell leukemia, head and neck cancer, hepatocellular (liver) cancer, histiocytosis, Hodgkin lymphoma, hypopharyngeal cancer, intraocular (eye) melanoma, intraocular melanoma, islet cell tumors, Kaposi sarcoma, kidney (renal cell) cancer, kidney cancer, Langerhans cell, Langerhans cell histiocytosis, laryngeal cancer, leukemia, lip and oral cavity cancer, lip and oropharyngeal cancer, liver cancer (metastatic), lung cancer (primary), macroglobulinemia, medulloblastoma, medulloepithelioma, melanoma, Merkel cell carcinoma, mesothelioma, metastatic squamous neck cancer with occult primary, metastatic stomach (gastric) cancer, mouth cancer, multiple endocrine neoplasia syndrome, multiple myeloproliferative disorders, mycosis fungoides, myelodysplastic syndromes, myelodysplastic/myeloproliferative diseases, myelogenous leukemia, nasal cavity and paranasal sinus cancer, nasopharyngeal cancer, nervous system atypical teratoid/rhabdoid tumor, neuroblastoma, non-Hodgkin lymphoma, non-small cell lung cancer, oral cancer, oral cavity cancer, osteosarcoma and malignant fibrous histiocytoma, osteosarcoma and malignant fibrous histiocytoma of bone, ovarian cancer, ovarian epithelial cancer, ovarian germ cell tumor, ovarian gestational trophoblastic tumor, ovarian low malignant potential tumor, pancreatic cancer, papillomatosis, paranasal sinus and nasal cavity cancer, parathyroid cancer, penile cancer, pharyngeal cancer, pineal parenchymal tumors, pineal parenchymal tumors of intermediate differentiation, pincoblastoma and supratentorial primitive neuroectodermal tumors, pituitary tumor, plasma cell neoplasm/multiple myeloma, pleuropulmonary blastoma, primary central nervous system lymphoma, primary cervical cancer, primary hepatocellular (liver) cancer, prostate cancer, rectal cancer, renal cell (kidney) cancer, renal pelvis and ureter, respiratory tract carcinoma involving the nut gene on chromosome 15, retinoblastoma, rhabdomyosarcoma, salivary gland cancer, sarcoma, skin cancer (Basal cell carcinoma), Sézary syndrome, skin cancer (nonmelanoma), skin carcinoma, small cell lung cancer, small cell lymphoma, small intestine cancer, soft tissue sarcoma, spinal cord tumors, squamous cell carcinoma, squamous neck cancer with occult primary, stomach (gastric) cancer, supratentorial primitive neuroectodermal tumors and pincoblastoma, T-cell lymphoma, teratoid/rhabdoid tumor (childhood), testicular cancer, throat cancer, thymoma and thymic carcinoma, thyroid cancer, transitional cell cancer, transitional cell cancer of the renal pelvis and ureter, trophoblastic tumor (gestational), unknown primary site, ureter and renal pelvis, urethral cancer, uterine cancer, uterine sarcoma, vaginal cancer, vulvar cancer, Waldenström macroglobulinemia, Waldenström malignant fibrous histiocytoma of bone and osteosarcoma, and Wilms tumor.

The therapeutic agent can be a chimera consisting of a peptide or protein, toxin, chimeric toxin, cytokine, antibody, bispecific antibody including single chain antibodies, camel antibodies and nanobodies chemokine, prodrug converting enzyme or metabolite-degrading enzyme such as thiaminase, methionase (methioninase, L-methionine γ-lyase) or asparaginase. In a preferred embodiment the therapeutic agent is a toxin, or modified toxin.

The chimeras may be further modified by addition of one or more multimerization domains, such as the T4 foldon trimerization domain (Meier et al., 2004, Journal of Molecular Biology, 344:1051-1069; Bhardwaj et al., Protein Sci. 2008 17:1475-1485) or tetramerization domains such as VASP (Kühnel et al., 2004 PNAS 101:17027-17032). Chimeric toxins may be further modified by the addition of known cell penetrating (ferry) peptide which further improves their entry into target cells. Cell penetrating peptides include those derived from the HIV TAT protein (e.g., TAT-apoptin, TAT-bim, TAT-p53), the antennapedia homeodomain (penetraxin), Kaposi fibroblast growth factor (FGF) membrane-translocating sequence (MTS), herpes simplex virus VP22, hexahistidine, hexalysine, hexaarginine or "Chariot" (Active Motif, Carlsbad, CA; U.S. Pat. No. 6,841,535). Nuclear localization signals (NLSs) may also be added, including but not limited to that from herpes simplex virus thymidine kinase, the SV40 large T antigen monopartite NLS, or the nucleoplasmin bipartite NLS or more preferably, the NLS from apoptin, a tumor associated (tumor-selective) NLS. The tumor-selective nuclear export signal from apoptin may be used alone or together with NLS from apoptin (Heckl et al., 2008, Value of apoptin's 40-amino-acid C-terminal fragment for the differentiation between human tumor and non-tumor cells, Apoptosis 13:495-508; Backendor et al., 2008, Apoptin: Therapeutic potential of an early sensor of carcinogenic transformation, Ann Rev Pharmacol Toxicol 48:143-69).

The chimeric proteins may have one or more additional features or protein domains known to those skilled in the art which are designed to be active or catalytic domains that result in the death of the cell, allow or facilitate them being secreted or released by autolytic peptides such as those associated with colicins or bacteriophage release peptides have targeting peptides that direct them to the target cells, and protease cleavage sites for activation (e.g., release from parent peptide), and thioredoxin or glutathione S-transferase (GST) fusions that improve solubility.

The present technology also provides in accordance with some embodiments, unique chimeric modifications of the above listed toxins that contain specific combinations of components resulting in secretion by selective anti-tumor activity. The technology also provides extracellular protease sensitivity (deactivation) that may include the addition of protease cleavage sites and may be co-expressed with a protease inhibitor. The chimeric proteins may have one or more additional features or protein domains known to those skilled in the art which are designed to 1) be active or catalytic domains that result in the death of the cell or make them susceptible to other known anticancer agents, 2) allow or facilitate them being secreted or released by autolytic peptides such as colicin release peptides, 3) membrane protein transduction (ferry) peptides, 4) autotransporter domains, 5) have targeting peptides that direct them to the target cells, and 6) protease cleavage sites for activation (e.g., release from parent peptide). However, the specific organization and combination of these domains is unique and specific to the technology.

Small lytic peptides (less than 50 amino acids) are used to construct chimeric proteins for more than one purpose. The chimeric proteins containing lytic peptides may be directly cytotoxic for the cancer cells, and/or other cells of the tumor including the tumor matrix cells and immune cells which may diminish the effects of the bacteria by eliminating them. Furthermore, the lytic peptides are useful in chimeric proteins for affecting release from the endosome. Small lytic peptides have been used in the experimental treatment of cancer. However, it is evident that most, if not all, of the commonly used antitumor small lytic peptides have strong antibacterial activity, and thus are not compatible with delivery by a bacterium (see Table 1 of Leschner and Hansel, 2004 Current Pharmaceutical Design 10:2299-2310, the entirety of which is expressly incorporated herein by reference). Small lytic peptides useful in the technology, according to various embodiments, are those derived from *Staphylococcus aureus, S. epidermidis* and related species, including the phenol-soluble modulin (PSM) peptides and delta-lysin (Wang et al., 2007 Nature Medicine 13:1510-1514, expressly incorporated herein by reference). Larger lytic peptides that may be used includes the actinoporins from sea anemones or other coelenterates, such as SrcI, FraC equinatoxin-II and sticholysin-II (Anderluh and Macek 2002, Toxicon 40:111-124). The selection of the lytic peptide depends upon the primary purpose of the construct, which may be used in combination with other constructs providing other anticancer features. Construct designed to be directly cytotoxic to cells employ the more cytotoxic peptides, particularly PSM-α-3 and actinoporins. Constructs which are designed to use the lytic peptide to affect escape from the endosome use the peptides with the lower level of cytotoxicity, such as PSM-alpha-1, PSM-α-2 or delta-lysin.

Promoters, i.e., genetic regulatory elements that control the expression of the genes encoding the therapeutic molecules described above that are useful in the present technology, according to various embodiments, include constitutive and inducible promoters. A preferred constitutive promoter is that from the vector pTrc99a (Promega). Preferred inducible promoters include the tetracycline inducible promoter (TET promoter), SOS-response promoters responsive to DNA damaging agents such as mitomycin, alkylating agents, X-rays and ultraviolet (UV) light such as the recA promoter, colicin promoters, sulA promoters and hypoxic-inducible promoters including but not limited to the PepT promoter (Bermudes et al., WO 01/25397), the arabinose inducible promoter (AraBAD) (Lossner et al., 2007, Cell Microbiol. 9:1529-1537; WO/2006/048344) the salicylate (aspirin) derivatives inducible promoter (Royo et al., 2007, Nature Methods 4:937-942; WO/2005/054477), a tumor-specific promoter (Arrach et al., 2008, Cancer Research 68:4827-4832; WO/2009/152480) or a quorum-sensing (autoinduction) promoter Anerson et al., 2006 Environmentally controlled invasion of cancer cells by engineered bacteria, J. Mol. Biol. 355:619-627.

A single promoter may be used to drive the expression of more than one gene, such as a protease sensitive toxin and a protease inhibitor. The genes may be part of a single synthetic operon (polycistronic), or may be separate, mono-cystronic constructs, with separate individual promoters of the same type used to drive the expression of their respective genes. The promoters may also be of different types, with different genes expressed by different constitutive or inducible promoters. Use of two separate inducible promoter for more than one cytotoxin or other effector type peptide allows, when sufficient X-ray, tetracycline, arabinose or salicylic acid is administered following administration of the bacterial vector, their expression to occur simultaneously, sequentially, or alternatingly (i.e., repeated).

OBJECTS OF THE INVENTION

The present technology provides, according to one embodiment, live attenuated therapeutic bacterial strains that express one or more therapeutic molecules. The technology, according to various embodiments, relates specifically to certain modified forms of chimeric toxins especially suitable for expression by tumor-targeted bacteria. In a preferred embodiment, the modified toxin is derived from cytolethal distending toxin. In a more preferred embodiment, the cytolethal distending toxin is derived from *Salmonella paratyphi* A, *Salmonella typhi* or *Salmonella bongori*. In particular, the technology, according to various embodiments, relates to live attenuated tumor-targeted bacterial strains that may include *Salmonella* sp., group B *Streptococcus Bifidobacterium* sp. or *Listeria* vectoring chimeric anti-tumor toxins to an individual to elicit a therapeutic response against cancer. Another aspect of the technology relates to live attenuated tumor-targeted bacterial strains that may include *Salmonella*, group B *Streptococcus Bifidobacterium* sp. or *Listeria* vectoring chimeric anti-tumor toxin molecules to an individual to elicit a therapeutic response against cancer including cancer stem cells. The toxins may also be targeted to tumor matrix cells, and/or immune cells. In another embodiment of the technology, *Salmonella* strains including *Salmonella paratyphi* A. *Salmonella typhi* or *Salmonella bongori* which contain endogenous cytolethal distending toxins may, when suitably attenuated, be used as vectors for delivery of cytolethal distending toxin. In order to achieve inducible control, the endogenous reporter is replaced with an inducible promoter by homologous recombination. In another embodiment, a chimeric secreted protease inhibitor is used alone or in combination with the chimeric toxins.

Whereas the prior strains of *Salmonella* studied in human clinical trials used either no heterologous antitumor protein (i.e., VNP20009) or an antitumor protein located within the cytoplasm of the bacterium (i.e., cytosine deaminase expressed by TAPET-CD), or secreted proteins (Bermudes et al., WO 2001/025397) the technology, according to various embodiments, provides, according to some embodiments, methods and compositions comprising bacterial vectors that express, secrete, surface display and/or release protease inhibitors that protect co-expressed protease sensitive antitumor molecules that are also secreted, surface displayed and/or released into the tumor, lymphoma-containing lymph node, leukemic bone lumen, or proximally or topically on a carcinoma or precancerous lesion for the treatment of the neoplasia.

The primary characteristic of the bacteria of the technology, according to various embodiments, is the enhanced effect of the effector molecule such as a toxin, lytic peptide etc. relative to the parental strain of bacteria. In one embodiment, the percent increase in effect is approximately 2% to approximately 95%, approximately 2% to approximately 75%, approximately 2% to approximately 50%, approximately 2% to about 40%, approximately 2% to about 30%, approximately 2% to about 25%, approximately 2% to about 20% or about 2% to approximately 10% greater than the parental strain of bacteria without expressing one or more protease inhibitors under the same conditions. A second characteristic of the bacteria of the technology, according to various embodiments, is that they carry novel chimeric proteins that improve their function compared to other chimeric protein expression systems. In one embodiment, the percent improvement is approximately 2% to approximately 95%, approximately 2% to approximately 75%, approximately 2% to approximately 50%, approximately 2% to about 40%, approximately 2% to about 30%, approximately 2% to about 25%, approximately 2% to about 20% or about 2% to approximately 10% that of another expression system under the same conditions.

The bacteria according to a preferred embodiment of the present technology, according to various embodiments, include those modified to have little or no ability to undergo bacterial conjugation, limiting incoming and outgoing exchange of genetic material, whereas the prior art fails to limit exchange of genetic material. In addition, certain of the therapeutic molecules have co-transmission requirements (e.g., colicin proteins and colicin immunity) that are distal (i.e., genetically dissected and separated) to the therapeutic molecule location further limiting known forms of genetic exchange.

Aspects of the present technology also provide novel chimeric bacterial toxins particularly suited for expression by gram-negative bacteria. The toxins may have added targeting ligands that render them selectively cytotoxic for tumor cells, tumor stem cells and/or matrix and tumor-infiltrating immune cells. The technology also provides means to determine optimal toxin combinations which are preferably additive or more preferably synergistic. The technology also provides means to determine the optimal combination of protein toxin with conventional cancer chemotherapeutics, liposomal agents or biologics, including immunosuppressive anti-complement agents (e.g., anti-C5B). Accordingly, administration to an individual, of a live *Salmonella* bacterial vector, in accordance with an aspect of the present technology, that is genetically engineered to express one or more protease inhibitors as described herein co-expressed with one or more cytotoxic proteins has the ability to establish a population in the tumor, kill tumor cells, tumor stem cells as well as tumor matrix and immune infiltrating cells, resulting in a therapeutic benefit.

A preferred composition will contain, for example, a sufficient amount of live bacteria expressing the targeted cytotoxin(s) or effector proteins/peptides to produce a therapeutic response in the patient. Accordingly, the attenuated *Salmonella* strains described herein are both safe and useful as live bacterial vectors that can be systemically or orally administered to an individual to provide therapeutic benefit for the treatment of cancer.

Although not wishing to be bound by any particular mechanism, an effective antitumor response in humans by administration of genetically engineered, attenuated strains of *Salmonella* strains as described herein may be due to the ability of such mutant strains to persist within the tumor, lymphoma or leukemic bone marrow and to supply their own nutrient needs by killing tumor cells, tumor matrix and or immune infiltrating cells and further expanding the zone of the tumor that they occupy. Bacterial strains useful in accordance with a preferred aspect of the technology may carry the ability to produce a therapeutic molecule expressing plasmid or chromosomally integrated cassette that encodes and directs expression of one or more therapeutic molecules together with optionally one or more protease inhibitors, as described herein. The protease inhibitors serve to prevent the destruction of the therapeutic molecule while within the tumor. The protease inhibitor may also have an anticlotting effect, wherein a blood clot may prevent spread of the bacteria throughout the tumor. The protease inhibitor may also have direct or indirect anticancer effects through the inhibition of proteases that participate in the spread of cancerous cells. If the cytotoxin and protease inhibitor diffuse outside of the tumor, lymph node, bone lumen, proximity to a carcinoma or other neoplasia-localized distribution, they fall below the protease inhibitory concentration, no longer inhibit proteolysis of the cytotoxins or effector genes, and are then inactivated. Thus the protease inhibitor system both increases activity and provides tumor specificity.

The serovars of *S. enterica* that may be used as the attenuated bacterium of the live compositions described in accordance with various embodiments herein include, without limitation, *Salmonella enterica* serovar *Typhimurium* ("*S. typhimurium*"), *Salmonella montevideo, Salmonella enterica* serovar *Typhi* ("*S. typhi*"), *Salmonella enterica* serovar Paratyphi A ("*S. paratyphi* A"), *Salmonella enterica* serovar Paratyphi B ("*S. paratyphi* B"), *Salmonella enterica* serovar Paratyphi C ("*S. paratyphi* C"), *Salmonella enterica* serovar Hadar ("*S. hadar*"), *Salmonella enterica* serovar *Enteriditis* ("*S. enteriditis*"), *Salmonella enterica* serovar Kentucky ("*S. kentucky*"), *Salmonella enterica* serovar *Infantis* ("*S. infantis*"), *Salmonella enterica* serovar Pullorum ("*S. pullorum*"), *Salmonella enterica* serovar *Gallinarum* ("*S. gallinarum*"), *Salmonella enterica* serovar Muenchen ("*S. muenchen*"), *Salmonella enterica* serovar Anaturn ("*S. anatum*"), *Salmonella enterica* serovar Dublin ("*S. dublin*"), *Salmonella enterica* scrovar Derby ("*S. derby*"), *Salmonella enterica* serovar *Choleraesuis* var. Kunzendorf ("*S. cholerae* kunzendorf), and *Salmonella enterica* serovar Minnesota (*S. minnesota*). A preferred serotype for the treatment of bone marrow related diseases is *S. dublin*. In another embodiment of the technology, *Salmonella* strains including *Salmonella paratyphi* A, *Salmonella typhi* or *Salmonella bongori* which contain endogenous cytolethal distending toxins, may, when suitably attenuated, be used as vectors for delivery of cytolethal distending toxin. In order to achieve inducible control, the endogenous reporter is replaced with an inducible promoter by homologous recombination.

By way of example, live bacteria in accordance with aspects of the technology include known strains of *S. enterica* serovar *Typhimurium* (*S. typhimurium*) and *S. enterica* serovar *Typhi* (*S. typhi*) which are further modified as provided by the technology to form vectors for the prevention and/or treatment of neoplasia. Such Strains include Ty21a, CMV906, CMV908, CMV906-htr, CMV908-htr. Ty800, aroA-/serC-, holavax, M01ZH09, VNP20009. These strains contain defined mutations within specific serotypes of bacteria. The technology also includes the use of these same mutational combinations contained within alternate serotypes or strains in order to avoid immune reactions which may occur in subsequent administrations. In a preferred embodiment, S. *Typhimurium, S. montevideo*, and *S. typhi* which have non-overlapping O-antigen presentation (e.g., *S. typhimurium* is O—1, 4, 5, 12 and *S. typhi* is Vi, *S. montevideo* is O—6, 7) may be used. Thus, for example, *S. typhimurium* is a suitable serotype for a first injection and another serotype such as *S. typhi* or *S. montevideo* are used for a second injection and third injections. Likewise, the flagellar antigens are also selected for non-overlapping antigenicity between different injections. The flagellar antigen may be H1 or H2 or no flagellar antigen, which, when combined with the three different O-antigen serotypes, provides three completely different antigenic profiles.

Novel strains of *Salmonella* are also encompassed that are, for example, attenuated in virulence by mutations in a variety of metabolic and structural genes. The technology therefore may provide a live composition for treating cancer comprising a live attenuated bacterium that is a scrovar of *Salmonella enterica* comprising an attenuating mutation in a genetic locus of the chromosome of said bacterium that attenuates virulence of said bacterium and wherein said attenuating mutation is a combinations of other known attenuating mutations. Other attenuating mutation useful in the *Salmonella* bacterial strains described herein may be in a genetic locus selected from the group consisting of phoP, phoQ, edt, cya, crp, poxA, rpoS, htrA, nuoG, pmi, pabA, pts, damA, met, cys, pur, purA, purB, purI, purF, leu, ilv, arg, lys, zwf, aroA, aroB, aroC, aroD, serC, gua, cadA, rfc, rjb, rfa, ompR, msbB, pfkAB, crr, glk, ptsG, ptsHI, manXYZ and combinations thereof. The strain may also contain a mutation known as "Suwwan", which is an approximately 100 KB deletion between two IS200 elements. The strain may also carry a defective thioredoxin gene (trxA-; which may be used in combination with a TrxA fusion), a defective glutathione oxidoreductase (gor-) and optionally, overexpress a protein disulfide bond isomerase (DsbA). The strain may also be engineered to express invasion and/or escape genes tlyA, tlyC patI and pld from *Rickettsia*, whereby the bacteria exhibit enhanced invasion and/or escape from the phagolysosome (Witworth et al., 2005, Infect. Immun. 73:6668-6673), thereby enhancing the activity of the effector genes described below. The strain may also be engineered to be deleted in an avirulence (anti-virulence) gene, such as zirTS, grvA and/or pegL, or express the *E. coli* lac repressor, which is also an avirulence gene in order to compensate for over-attenuation. The strain may also express SlyA, a known transcriptional activator. In a preferred embodiment, the *Salmonella* strains are msbB mutants (msbB-). In a more preferred embodiment, the strains are msbB- and Suwwan. In a more preferred embodiment the strains are msbB-, Suwwan and zwf-. Zwf has recently been shown to provide resistance to $CO_2$, acidic pH and osmolarity (Karsten et al., 2009, BMC Microbiology August 18; 9:170). Use of the msbB zwf genetic combination is also particularly preferred for use in combination with administered carbogen (an oxygen carbon dioxide mixture that may enhance delivery of therapeutic agents to a tumor). In a more preferred embodiment, the strains are msbB-, Suwwan, zwf- and trxA-. In a most preferred embodiment, the strains are msbB-, Suwwan, zwf-, trxA- and gor-.

The technology also encompasses according to a preferred embodiment, gram-positive bacteria. Preferred bacteria of the technology are group B *Streptococcus* including *S. agalaciae, Bifidobacterium* sp, and *Listeria* species including *L. monocytogenes*. It is known to those skilled in the art that minor variations in molecular biology techniques such as use of gram-positive origins of replication, gram-positive signal sequences gram-positive promoters (e.g., *Lactococcus* expression, Mohamadzadeh et al., PNAS Mar. 17, 2009 vol. 106 no. 11 4331-4336; Geertsma and Poolman, 2007, High-throughput cloning and expression in recalcitrant bacteria, Nature Methods 4:705-707; Prudhomme et al., 2006, Antibiotic stress induces genetic transformability in the human pathogen *Streptococcus pneumoniae*, Science 313:89-92; WO/2009/139985 Methods and materials for gastrointestinal delivery of a pathogen toxin binding agent; van Asseldonk, M et al. 1990, Cloning of usp45, a gene encoding a secreted protein from *Lactococcus lactis* subsp. *lactis* MG1363 Gene 95, 15-160; Kim et al., J Appl Microbiol. 2008 June; 104 (6): 1636-43. Epub 2008 Feb. 19. Display of heterologous proteins on the surface of *Lactococcus lactis* using the H and W domain of PrtB from *Lactobacillus delburueckii* subsp. *bulgaricus* as an anchoring matrix; Lee et al., 1999, Characterization of *Enterococcus faecalis* alkaline phosphatase and use in identifying *Streptococcus agalactiae* secreted proteins, J. Bacteriol 181 (18): 5790-9.) are required and substituted as needed.

Mutational backgrounds of *Listeria* vectors include those previously isolated, including the delta-actA strain 142 (Wallecha et al., 2009, Construction and characterization of an attenuated *Listera monocytogenes* strain for clinical use in cancer immunotherapy, Clin Vaccine Immunol 16:96-103), the double D-alanine (D-ala) strain described by Jiang et al., 2007, Vaccine 16:7470-7479, Yoshimura et al., 2006, Cancer Research 66:1096-1104. Lenz et al., 2008, Clinical and Vaccine Immunology 15:1414-1419, Roberts et al., 2005, Definition of genetically distinct attenuation mechanisms in naturally virulent *Listeria moncyogenes* by comparative cell culture and molecular characterization, Appl. Environ. Microbiol 71:3900-3910, the actA, prfA strain by Yan et al., Infect Immun 76:3439-3450, and those described by Portnoy et al., EP1513924 and Portnoy et al., WO/2003/102168.

Mutational backgrounds of the group B *Streptococcus, S. agalactiae*, include wild type (no mutations), of any of the nine serotypes that depend on the immunologic reactivity of the polysaccharide capsule and among nine serotypes, preferably types Ia, Ib, II, III, and V capable of being invasive in humans. The strain may be deleted in the beta-hemolysin/cytolysin (beta-H/C), including any member of the cly operon, preferably the clyE gene, or the CspA protease associated with virulence (Shelver and Bryan, 2008, J Bacteriol. 136:129-134), or the hyaluronate lyse C5a peptidase CAMP factor, oligopeptidase (Liu and Nizet 2004, Frontiers in Biosci 9:1794-1802; Doran and Nizet 2004, Mol Microbiol 54:23-31; Herbert et al., 2004, Curr Opin Infect Dis 17:225-229). The strains may further have mutations in metabolic genes pur, *purA*, aroA, aroB, aroC, aroD, pgi (glucose-6-phosphate isomerase), fructose-1,6-bisphosphatase, ptsH, ptsI, and/or one or more amino acid transporters and/or amino acid permeases. In a preferred embodiment, the strain is clyE deficient.

Other bacterial strains are also encompassed, including non-pathogenic bacteria of the gut such as *E. coli* strains, *Bacteroides, Bifidobacterium* and *Bacillus*, attenuated pathogenic strains of *E. coli* including enteropathogenic and uropathogenic isolates, *Enterococcus* sp. and *Serratia* sp. as well as attenuated *Shigella* sp., *Yersinia* sp., *Streptococcus* sp. and *Listeria* sp.

Bacteria of low pathogenic potential to humans such as *Clostridium* spp. and attenuated *Clostridium* spp., *Proteus mirabilis*, insect pathogenic *Xenorhabdus* sp., *Photorhabdus* sp. and human wound *Photorhabdus* (*Xenorhabdus*) are also encompassed. Probiotic strains of bacteria are also encompassed, including *Lactobacillus* sp., *Lactococcus* sp., *Leuconostoc* sp., *Pediococcus* sp., *Streptococcus* sp., *Streptococcus agalactiae, Lactococcus* sp., *Bacillus* sp., *Bacillus* natto, *Bifidobacterium* sp., *Bacteroides* sp., and *Escherichia coli* such as the 1917 Nissel strain.

The technology also provides, according to one embodiment, a process for preparing genetically stable therapeutic bacterial strains comprising genetically engineering the therapeutic genes of interest into a bacterially codon optimized expression sequence within a bacterial plasmid expression vector, endogenous virulence (VIR) plasmid (of *Salmonella* sp.), or chromosomal localization expression vector for any of the deleted genes or IS200 genes, defective phage or intergenic regions within the strain and further containing engineered restriction endonuclease sites such that the bacterially codon optimized expression gene contains subcomponents which are easily and rapidly exchangeable, and the bacterial strains so produced. Administration of the strain to the patient is therapeutic for the treatment of cancer.

The present technology provides, for example, and without limitation, live bacterial compositions that are genetically engineered to express one or more protease inhibitors combined with antitumor effector molecules for the treatment of cancers or neoplasias.

According to various embodiments, the technology provides pharmaceutical compositions comprising pharmaceutically acceptable carriers and one or more bacterial mutants. The technology also provides pharmaceutical compositions comprising pharmaceutically acceptable carriers and one or more bacterial mutants comprising nucleotide sequences encoding one or more therapeutic molecules. The pharmaceutical compositions of the technology may be used in accordance with the methods of the technology for the prophylaxis or treatment of neoplastic disease. Preferably, the bacterial mutants are attenuated by introducing one or more mutations in one or more genes in the lipopolysaccharide (LPS) biosynthetic pathway (for gram-negative bacteria), and optionally one or more mutations to auxotrophy for one or more nutrients or metabolites.

In one embodiment, a pharmaceutical composition comprises a pharmaceutically acceptable carrier and one or more bacterial mutants, wherein said attenuated bacterial mutants are facultative anaerobes or facultative acrobes. In another embodiment, a pharmaceutical composition comprises a pharmaceutically acceptable carrier and one or more attenuated bacterial mutants, wherein said attenuated bacterial mutants are facultative anaerobes or facultative aerobes and comprise one or more nucleic acid molecules encoding one or more therapeutic molecules where the therapeutic molecule is chimeric toxin.

In one embodiment, a pharmaceutical composition comprises a pharmaceutically acceptable carrier and one or more bacterial mutants, wherein said attenuated bacterial mutants are facultative anaerobes or facultative acrobes. In another embodiment, a pharmaceutical composition comprises a pharmaceutically acceptable carrier and one or more attenuated bacterial mutants, wherein said attenuated bacterial mutants are facultative anaerobes or facultative aerobes and comprise one or more nucleic acid molecules encoding one or more therapeutic molecules where the therapeutic molecule is a molecule with direct anti-cancer lytic capability.

In one embodiment, a pharmaceutical composition comprises a pharmaceutically acceptable carrier and one or more bacterial mutants, wherein said attenuated bacterial mutants are facultative anaerobes or facultative acrobes. In another embodiment, a pharmaceutical composition comprises a pharmaceutically acceptable carrier and one or more attenuated bacterial mutants, wherein said attenuated bacterial mutants are facultative anaerobes or facultative aerobes and comprise one or more nucleic acid molecules encoding one or more therapeutic molecules where the therapeutic molecule has direct anti-cancer cytotoxic or inhibitory ability.

In one embodiment, a pharmaceutical composition comprises a pharmaceutically acceptable carrier and one or more bacterial mutants, wherein said attenuated bacterial mutants are facultative anaerobes or facultative acrobes. In another embodiment, a pharmaceutical composition comprises a pharmaceutically acceptable carrier and one or more attenuated bacterial mutants, wherein said attenuated bacterial mutants are facultative anaerobes or facultative aerobes and comprise one or more nucleic acid molecules encoding one or more therapeutic molecules where the therapeutic molecule has direct anti-cellular activity against other cells of a tumor, including neutrophils, macrophages, T-cells, stromal cells, endothelial cells (tumor vasculature) and/or cancer stem cells.

In one embodiment, a pharmaceutical composition comprises a pharmaceutically acceptable carrier and one or more bacterial mutants, wherein said attenuated bacterial mutants are facultative anaerobes or facultative aerobes. In another embodiment, a pharmaceutical composition comprises a pharmaceutically acceptable carrier and one or more attenuated bacterial mutants, wherein said attenuated bacterial mutants are facultative anaerobes or facultative acrobes and comprise one or more nucleic acid molecules encoding one or more therapeutic molecules co-expressed with a protease inhibitor.

In a specific embodiment, a pharmaceutical composition comprises a pharmaceutically acceptable carrier and one or more attenuated bacterial mutants, wherein the bacterial mutants are a *Salmonella* sp. In another specific embodiment, a pharmaceutical composition comprises a pharmaceutically acceptable carrier and one or more attenuated stress-resistant gram-negative bacterial mutants, wherein the attenuated stress-resistant gram-negative bacterial mutants are a *Salmonella* sp., and the attenuated stress-resistant gram-negative bacterial mutants comprise one or more nucleic acid molecules encoding one or more therapeutic molecules, prodrug converting enzymes, metabolite degrading enzymes, lytic peptides, DNases or anti-cancer peptides.

In a specific embodiment, a pharmaceutical composition comprises a pharmaceutically acceptable carrier and one or more attenuated bacterial mutants, wherein the bacterial mutants are a *Streptococcus* sp. In another specific embodiment, a pharmaceutical composition comprises a pharmaceutically acceptable carrier and one or more attenuated gram-positive bacterial mutants, wherein the attenuated gram-positive bacterial mutants are a *Streptococcus* sp., and the attenuated gram-positive bacterial mutants comprise one or more nucleic acid molecules encoding one or more therapeutic molecules, prodrug converting enzymes, metabolite degrading enzyme, lytic peptides, DNases or anti-cancer peptides.

In a specific embodiment, a pharmaceutical composition comprises a pharmaceutically acceptable carrier and one or more attenuated bacterial mutants, wherein the bacterial mutants are a *Listeria* sp. In another specific embodiment, a pharmaceutical composition comprises a pharmaceutically acceptable carrier and one or more attenuated bacterial mutants, wherein the attenuated gram-positive bacterial mutants are a *Listeria* sp., and the attenuated gram-positive bacterial mutants comprise one or more nucleic acid molecules encoding one or more therapeutic molecules, prodrug converting enzymes, metabolite degrading enzyme, lytic peptides, DNases or anti-cancer peptides.

The present technology, according to various embodiments, encompasses treatment protocols that provide a better therapeutic effect than current existing anticancer therapies. In particular, the present technology provides methods for prophylaxis or treatment of neoplastic diseases in a subject comprising administering to said subject and one or more bacterial mutants. The present technology also provides methods for the prophylaxis or treatment of neoplastic diseases in a subject comprising administering to said subject one or more bacterial mutants, wherein said bacterial mutants comprise one or more nucleic acid molecules encoding one or more therapeutic molecules together with one or more protease inhibitors.

The methods of the present technology, according to various embodiments, permit lower dosages and/or less frequent dosing of the bacterial mutants to be administered to a subject for prophylaxis or treatment of neoplastic disease to achieve a therapeutically effective amount of one or more therapeutic molecules. In a preferred embodiment, the genetically modified bacteria are used in animals, including humans, dogs, cats, and/or horses for protection or treatment against neoplastic diseases.

Accordingly, when administered to an individual, a live *Salmonella, Listeria. Bifidobacterium* or *Streptococcus* bacterial vector or therapeutic, in accordance with the present technology, that is genetically engineered to express one or more anti-neoplastic molecules or molecules against other cells within the neoplastic milieu, optionally in combination with a protease inhibitor, and have improved efficacy due to improved surface display, secretion and/or released of the modified chimeric therapeutic proteins and/or enhanced binding to the target receptor resulting enhanced therapeutic activity against a neoplastic tissue including solid tumors, lymphomas and leukemias.

It is therefore an object to provide a genetic construct which causes a live host bacterium to express a chimeric peptide comprising a cytolethal distending toxin: apoptin fusion terminating in cysteine expressed or secreted. The genetic construct or bacterium may be provided in a pharmaceutically acceptable dosage form, suitable for administration to a human or animal, without causing significant morbidity. The peptide may act as an antineoplastic agent, and the bacterium may be trophic for diseased or malignant growths. The dosage form may be oral, enteral, parenteral, intravenous, per anus, topical, or inhaled, for example. The peptide may comprise a combination of at least one secretion signal, a linker, and domain Ib.

A pharmaceutically effective dosage form may comprise between about 105 to 1012 live bacteria, within a lyophilized medium for oral administration. In some embodiments, about 109 live bacteria are administered.

The live host bacterium may have antineoplastic activity against lymphoma, or solid tumors.

The peptide may be, for example, the modified chimeric cytolethal distending toxin: apoptin fusion terminating at the C-terminus with cysteine with antineoplastic activity, having deletions of at least one cytolethal distending toxin nuclear localization signal.

Another object of the technology provides a chimeric protease inhibitor comprising YebF fused to sunflower trypsin inhibitor, adapted to inhibit at least one serine protease. The chimeric protease inhibitor may be formed by a genetically engineered bacteria, wherein the genetically engineered bacteria secretes the YebF fused to sunflower trypsin inhibitor. The chimeric protease inhibitor may be provided in combination with a host bacteria and a genetically engineered construct which encodes the chimeric protease inhibitor, wherein the host bacteria secretes the chimeric protease inhibitor and the chimeric protease inhibitor inhibits at least one serine protease.

According to one embodiment of the method, the live genetically bacterium is allowed to colonize at least one tissue of the human or animal after administration, and the human or animal is treated with at least one systemic antibiotic to which the live genetically engineered bacterium is sensitive. The antibiotic may be narrow spectrum, and indeed, may comprise a composition not generally toxic to other bacteria or animal cells.

DETAILED DESCRIPTION OF THE PREFERRED EMBODIMENTS

Figures 1A, 1B, 1C, 1D:
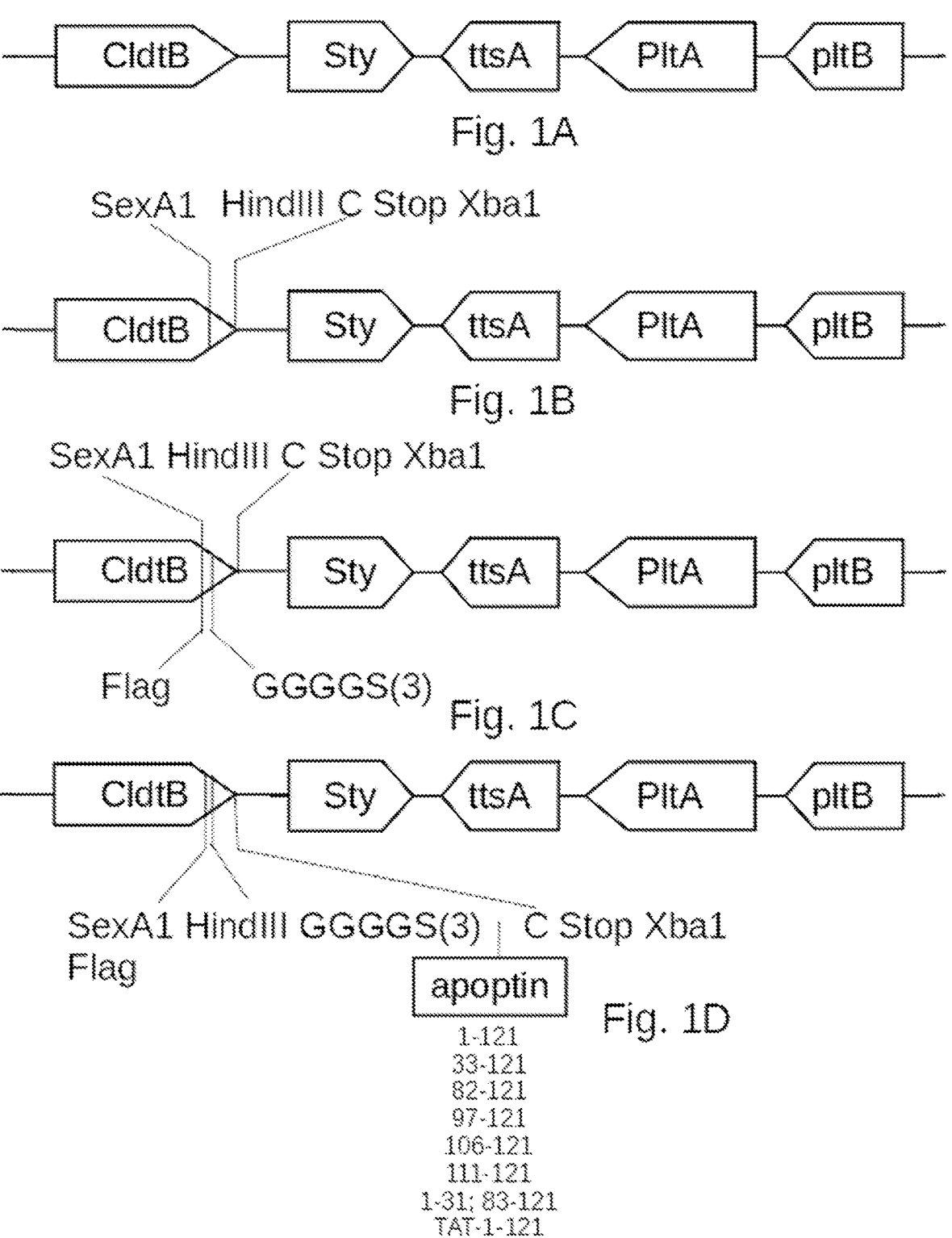
FIGS. 1A-1D show C-terminal modified cldt from *Salmonella paratyphi* A.

The present technology provides, according to various embodiments, live attenuated therapeutic bacterial strains that express one or more therapeutic with improved expression, secretion, surface display and/or release and/or have improved binding and anticancer cell activity that results in improved therapeutic efficacy. In particular, one aspect of the technology relates to live attenuated tumor-targeted bacterial strains that may include *Salmonella, Streptococcus* or *Listeria* vectoring novel chimeric anti-tumor toxins to an individual to elicit a therapeutic response against cancer. The types of cancer may generally include solid tumors, carcinomas, leukemias, lymphomas and multiple myelomas. Another aspect of the technology relates to live attenuated tumor-targeted bacterial strains that may include *Salmonella, Streptococcus, Clostridium* and *Listeria* that encode anti-neoplastic molecules to an individual to elicit a therapeutic response against cancers including cancer stem cells, immune infiltrating cells and or tumor matrix cells.

For reasons of clarity, the detailed description is divided into the following subsections: targeting ligands; chimeric bacterial toxins; and secreted protease inhibitors.

Targeting Ligands

Targeting ligands have specificity for the target cell and are used to both confer specificity to chimeric proteins, and to direct attachment and/or internalization into the target cell. The ligands are known ligands or may be novel ligands isolated through standard means such as phage display (Barbass III et al., 2004, Phage Display, A Laboratory Manual, Cold Spring Harbor Press) including the use of commercially available kits (Ph.D-7 Phage Display Library Kit, New England Biolabs, Ipswich, MA; Li et al., 2006. Molecular addresses of tumors: selection by in vivo phage display. Arch Immunol Ther Exp 54:177-181.). The ligands of various aspects of the present technology are peptides that can be expressed as fusions with other bacterially-expressed proteins. The peptides may be further modified, as for gastrin and bombesin, in being amidated by a peptidylglycine-alpha-amidating monoxygenase or C-terminal amidating enzyme, which is co-expressed in the bacteria that use these peptides using standard molecular genetic techniques. Examples of targeting peptides are shown in Bermudes U.S. Pat. No. 8,524,220 Table 4, incorporated by reference herein. These ligands and their targets include TGF-α (EGFR), HAVDI and INPISGQ and dimeric versions (N-cadherin of prostate), DUP-1 peptide (prostate cancer), laminin-411 binding peptides (brain neovasculature), DARPINS (e.g., H10, HER2), affibody against Her2 (Zielenski, R., Lyakhov, I., Jacobs, A., Chertov, O., Kramer-Marek, G., Francella, N., Stephen, A., Fisher, R., Blumenthal, R., and Capala, J. Affitoxin—A Novel Recombinant, HER2-Specific, Anti-Cancer Agent for Targeted Therapy of HER2-Positive Tumors. J Immunother. 2009 October; 32 (8): 817-825) luteinizing hormone-releasing hormone (LHRH receptor), IL2 (IL2R), EGF and EGF receptor related peptide (EGFR), tissue factor (TfR), IL4 (IL4R), IL134 (IL13R), GM-CSF (GM-CSFR), CAYHRLRRC SEQ ID NO: 002 (lymphoid tissue; AML), A33 antigen binding peptide (A33) CLTA-4/CD152 melanoma, CD19 binding peptides/Bpep (alpha (v) beta (6) integrin (αvβ6), non-Hodgkin lymphoma, chronic lymphocytic leukemia (CLL) and acute lymphocytic leukemia (ALL)), CD20 binding peptides (CD20, B-cell malignancies), CD22 binding peptides (B lymphocytes, hairy cell leukemia), CD25 binding peptides (chemotherapy-resistant human leukemia stem cells), TRU-015 (CD-20), CD30 binding peptides (CD-30 Hodgkin's lymphoma), CD32 binding peptides (chemotherapy resistant human leukemia stem cells), CD33 binding peptides (CD-33 AML mylcodysplastic cells MDS)), CD37 binding peptides (leukemia and lymphoma), CD40 binding peptides (CD40 multiple myeloma, non-Hodgkin lymphoma, chronic lymphocytic leukemia (CLL), Hodgkin lymphoma and acute lymphoblastic leukemia (ALL), diffuse large B-cell lymphoma, refractory non-Hodgkin lymphoma, including follicular lymphoma), CD52 (CLL), CD55 (CD55R), CD70 (hematological malignancies, non-Hodgkin's lymphoma), CD123 binding peptides (AML), RGD peptides (tumor cells and tumor endothelium), nanobodies derived from camels and llamas (camelids), including humanized nanobodies and VHH recognition domains (cancer), bombesin (gastrin releasing peptide receptor), gastrin releasing peptide (gastrin releasing peptide receptor), somatostatin octapeptide RC-121 (colon cancer), vasoactive intestinal peptide (tumor cell membranes), PTHrP (parathyroid hormone receptor G-protein coupled receptor), mesothelin binding peptides (mesothelin), CA125/MUC16 (mesothelin), heat stable enterotoxin (HST) (guanylyl cyclase C), GM-CSF (AML), vitronectin (Alfa (V) Beta (3) integrin), gastrin (gastrin receptor), CQTIDGKKYYFN SEQ ID NO: 003 peptide from *Clostridium*, affibody against HER3, DARPIN against HER2, TGFα, EGF, EGFR-binding peptides and other, non-limiting, peptides. In preferred embodiments, the peptides are affibody against HER2, H10 DARPIN against HER2, TGFα, EGF, EGFR-binding peptides.

Chimeric Bacterial Toxins

Chimeric toxins are toxins that may contain combinations of elements including targeting peptides, flexible linkers, disulfide bonding, lytic peptides, nuclear localization signals, blocking peptides, protease cleavage (deactivation or activation) sites, C-terminal secretion signals, autotransporter constructs, used to adapt the proteins to be expressed, secreted, surface displayed and/or released by bacteria to provide therapeutic molecules that are effective in treating neoplastic cells, stromal cells, neoplastic stem cells as well as immune infiltrating cells. Targeting to a particular cell type uses the appropriate ligand described above or from other known sources. Toxin activity is determined using standard methods known to those skilled in the art such as Aktories (ed) 1997 (Bacterial Toxins, Tools In Cell Biology and Pharmacology, Laboratory Companion, Chapman & Hall).

FIGS. 1A-1D show C-terminal fusions of modified cldt from *Salmonella paratyphi* A.

FIG. 1A shows the *Salmonella* typhoid toxin cytolethal distending toxin subunit B (cldtB) together with sty, ttsA, pltA and pltB. The entire operon is with cldtB and sty under control of an inducible promoter such as the arabinose inducible promoter, with pltB, pltA and ttsA under control of their upstream region.

FIG. 1B shows the cldtB, pltB and pltA artificial operon with an in frame fusion of the restriction enzymes SexA1, HindIII and a terminal cysteine and stop codons followed by Xba1.

FIG. 1C shows the cldtB, pltB and pltA artificial operon with SexA1, HindIII and Xba1 with the FLAG epitope and a GGGGS(×3), SEQ ID NO: 004 linker inserted in the SexA1 and HindIII sites and terminal cysteine and stop codons followed by Xba1.

FIG. 1D shows the cldtB. pltB and pltA artificial operon with SexA1, HindIII with the FLAG epitope and a GGGGS (×3), SEQ ID NO: 004 linker inserted in the SexA1 and HindIII sites and apoptin fragments inserted in-frame into the HindIII with a terminal cysteine and stop codons followed by an Xba1 site. The apoptin and/or apoptin fragments can consist of 1) apoptin 1-121, 2) apoptin 33-121, 3) apoptin 82-121, 4) apoptin 97-121, 5) apoptin 106-121, 6) apoptin 111-121 or 7) apoptin 1-31 linked to 83-121 or 8) TAT-apoptin, each of which is followed by a terminal cysteine and a stop codon.

Chimeric Cytolethal Distending Toxins,

Cytolethal distending toxins (cldt) including those cldts from *Haemophilus, Aggregatibacter, Salmonella, Escherichia, Shigella, Campylobacter, Helicobacter*, Hahella and *Yersinia*, typhoid toxins (pertussis like toxin) (pltAB), pertussis toxin, cldt:plt hybrids are three component toxins of these bacteria. Cldt is an endonuclease toxin and has a nuclear localization signal on the B subunit. Chimeric toxins are provided that utilize C-terminal fusions to apoptin, a canary virus protein that has a tumor-specific nuclear localization signal, and a normal (non-transformed) cell nuclear export signal. The present technology, according to one embodiment, consists of a modified *Salmonella* CLDT operon and forms of cytolethal distending toxins that are chimeric with apoptin and other peptide moieties including peptide linkers that improve activity and peptide blocking moieties that must be specifically cleaved to activate the protein.

The present technology, according to one embodiment, uses deletions in the CLDT nuclear localization signals which are then complemented by C-terminal fusions with apoptin, or apoptin fragments, which supply its nuclear localization signal in trans as a fusion peptide.

The cytolethal distending toxin B and chimeric cltdB may be expressed as a polycistronic construct consisting of cldtABC. The cytolethal distending toxin B and chimeric cltdB may be expressed as a polycistronic construct consisting containing the typhoid pertussis-like toxin (plt) AB genes. However, in the present technology, according to one embodiment, the presence of sty and ttsA are not required for secretion of the active toxin when the operon is reorganized into a unidirectional operon of cldtB, pltB and pltA.

Overall improvement is defined as an increase in effect, such as the ability to kill a neoplastic cells in vitro by the bacteria, or inhibit or reduce the volume or cell number of a solid tumor, carcinoma, lymphoma or leukemia in vivo following administration with the bacteria expressing a therapeutic molecule, with and without the protease inhibitor. The effect of the protein therapeutic activity is determined using standard techniques and assays known to those skilled in the art. The contribution of the therapeutic protein and protease inhibitors is determined individually and in combination. Additivity, synergy or antagonism may be determined using the median effect analysis (Chou and Talaly 1981 Eur. J. Biochem. 115:207-216) or other standard methods.

FIGS. 2A-2D show nuclear localization signal (NLS) modified partially or completely cldt from *Salmonella paratyphi* A.

Figures 2A, 2B, 2C, 2D:
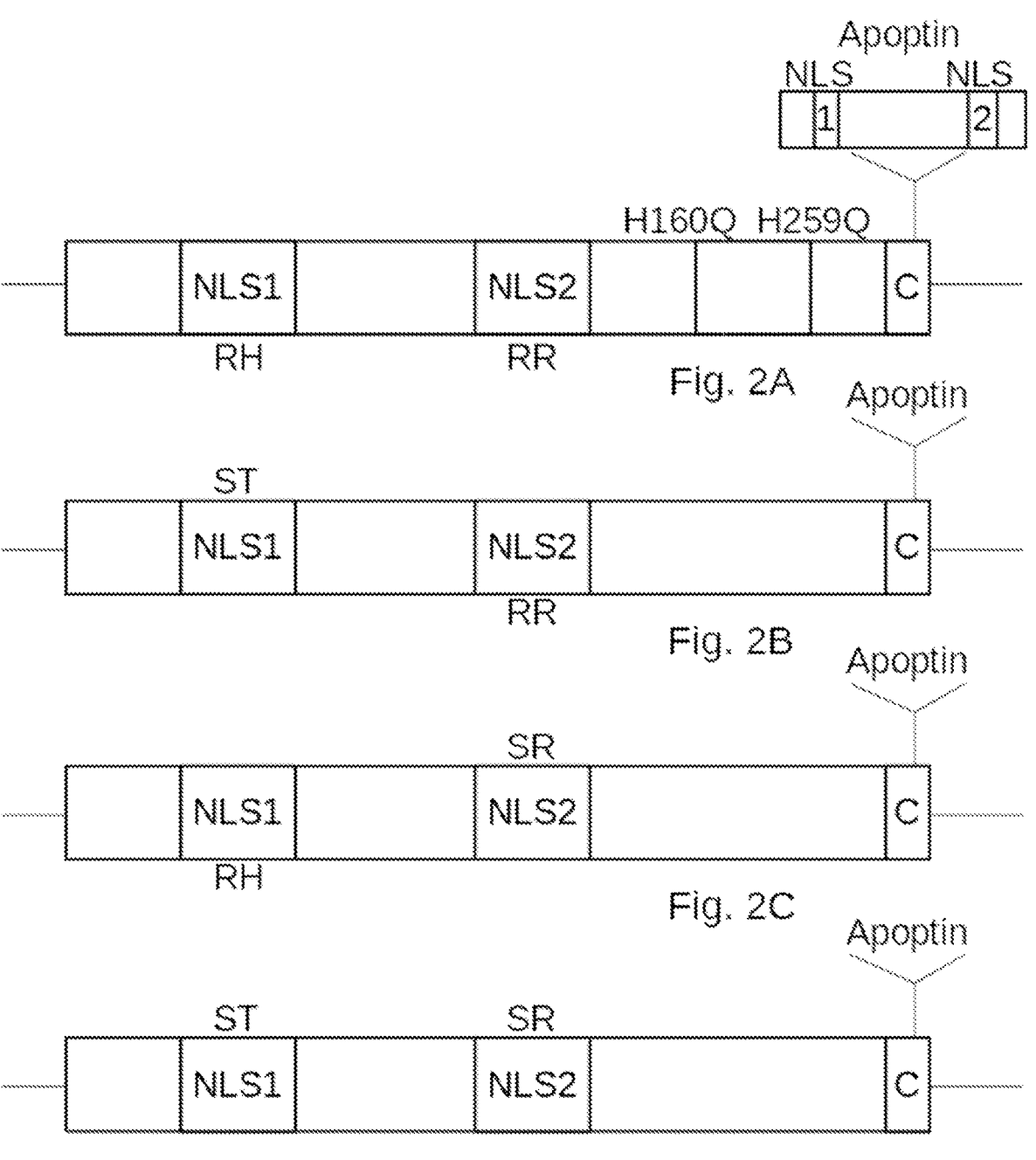
FIGS. 2A-2D show nuclear localization signal (NLS) modified cldt from *Salmonella paratyphi* A.

FIG. 2A shows inactivated *Salmonella paratyphi* A typhoid toxin as a delivery mechanism for peptide fusions. The *Salmonella* typhoid toxin cldtB is inactivated by site-directed mutagenesis of the known active sites such as H160Q and/or H259Q. Fusions to the inactivated form retain the secretion and delivery to the cytosol and allow transport to the nucleus.

FIG. 2B shows inactivated *Salmonella paratyphi* A typhoid toxin nuclear localization signals (NLS1) enhancing dependence on apoptin NLSs and/or nuclear export as a mode of tumor cell-specific delivery of an active cldtB.

FIG. 2C shows inactivation of NLS2 retaining a second arginine involved in DNA binding and FIG. 2D shows both portions of the cldtB bipartite nuclear localization signals can be altered from charged (basic) e.g., arginines and/or histidines to polar serines or threonines NLS2 retaining a second arginine involved in DNA binding.

Figure 3A:
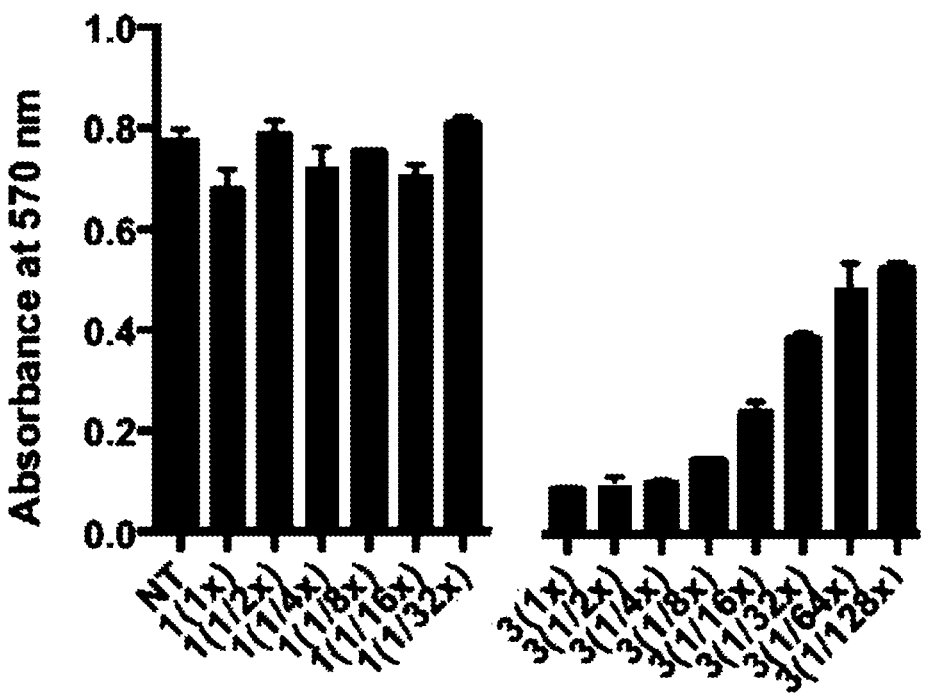
FIGS. 3A and 3B show results of a cytotoxicity (anticancer cell killing) assay of cytolethal distending toxin and cytolethal distending toxin: apoptin fusions.
Figure 3B:
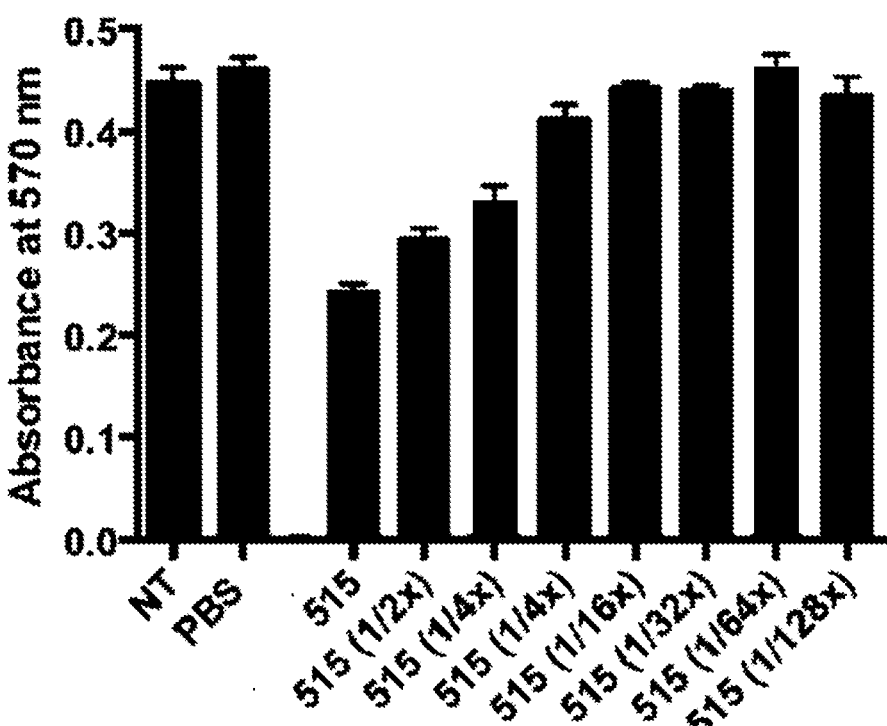

FIGS. 3A and 3B show results of a cytotoxicity (anticancer cell killing) assay of *Salmonella paratyphi* A cytolethal distending toxin and cytolethal distending toxin NLS deletions toward MDA-MB-468 breast cancer cells.

FIG. 3A, left. NT: no treatment, 1 (1×): treatment with 10 μL of a bacterial culture supernatant carrying an empty vector (EV) plasmid into a 100 μL tissue culture wells, with additional dilutions of ½, ¼, ⅛, ⅟₁₆ and ⅟₃₂.

FIG. 3A right: treatment with supernatant from the cloned *S. paratyphi* A cytolethal distending operon (clone 1-1+3) with concentrations of 1× ½, ¼, ⅛, ⅟₁₆ ⅟₃₂, ⅟₆₄ and ⅟₁₂₈, demonstrating cytotoxicity.

FIG. 3B: treatment with the supernatant of the NLS1 (−)/NLS2(−) (clone 515) construct showing loss of cytotoxic activity, with concentrations of 1× ½, ¼, ⅛, ⅟₁₆ ⅟₃₂, ⅟₆₄ and ⅟₁₂₈.

EXAMPLES

In order to more fully illustrate the technology, the following examples are provided.

Example 1 a *Salmonella* Expression Vector.

Inducible expression vectors for *E. coli* and *Salmonella*, such as arabinose inducible expression vectors, are widely available and known to those skilled in the art. By way of example, an expression vector typically contains a promoter which functions to generate an mRNA from the DNA, such as an inducible arabinose promoter with a functional ribosomal binding site (RBS) an initiation codon (ATG) and suitable cloning sites for operable insertion of the functional DNA encoding the effector proteins described below into the vector, followed by a transcriptional termination site, plasmid origin of replication, and an antibiotic resistance factor that allows selection for the plasmid. Vectors that lack antibiotic resistance such as asd(−) balanced lethal vectors (Galan et al., 1990 cloning and characterization of the asd gene of *Salmonella Typhimurium*: use in stable maintenance of recombinant *Salmonella* vaccine strains, Gene 94:29-35) may also be used, or insertion into the chromosome. A wild type gene sequence of *Salmonella* in a region of CldtB is shown in FIG. 1A.

Example 2

Apoptin C-Terminal Fusions with Typhoid Toxin cldtB.

An artificial, inducible typhoid toxin containing introduced FLAG epitope, GGGGS (×3) SEQ ID NO: 004 linker and HindIII with a terminal cystein followed by a stop codon and Xbal is used to insert apoptin, TAT-apoptin, and apoptin fragments as shown in FIG. 1D as generated by PCR and restriction endonuclease-based cloning methods and synthetic biology known to those skilled in the art. Fragments consisting of either 1) apoptin 1-121, 2) apoptin 33-121, 3) apoptin 82-121, 4) apoptin 97-121, 5) apoptin 106-121, 6) apoptin 111-121 or 7) apoptin 1-31 linked to 83-121 or 32 to 83 (not shown), each of which with C-terminal cysteines followed by a stop codon. By way of example complete sequence of the arabinose inducible plasmid capable of expressing the TAT-apoptin construct as a cldtB fusion, with TAT-apoptin inserted in-frame within the HindIII and XbaI sites introduced into typhoid toxin cldtB, with the TAT-apoptin coding sequence.

Example 3

C-terminal fusions with typhoid toxin cldtB and a modified apoptin wherein the phosphorylation site T108 and the two adjacent threonines 106 and 107 are mutated to alanines does not alter cytotoxicity. The mutations are made by methods known to those skilled in the art, with C-terminal cysteines followed by a stop codon. Modification of the phosphorylation sites abrogates the activity of apoptin. The resulting cytotoxicity test shows that there was no change in cytotoxicity, therefore, the cldtB: apoptin fusion does not acquire cell killing ability from the apoptin.

While the invention is shown by way of various examples and explanations, it should be understood that this specification and the drawings are intended to encompass the various combinations, sub-combinations, and permutations of the various features disclosed, and not limited by the particular combinations and sequences presented by way of example.

---

What is claimed is:

1. A chimeric peptide comprising a functional cytolethal distending toxin comprising a C-terminal fusion of three cytolethal distending toxin subunits, and a distinct nuclear localization signal separated by a flexible linker from the three cytolethal distending toxin subunits, the chimeric peptide being terminated with a cysteine, wherein the chimeric peptide is antineoplastic.

2. The chimeric peptide according to claim 1, wherein the functional cytolethal distending toxin comprises typhoid toxin cldtB.

3. The chimeric peptide according to claim 1, wherein the functional cytolethal distending toxin comprises cldtA, cldtB and cldtC.

4. The chimeric peptide according to claim 1, wherein the functional cytolethal distending toxin comprises cldtB, pltA, pltB, sty and ttsA.

5. The chimeric peptide according to claim 1, contained in a pharmaceutically acceptable dosage form.

6. The chimeric peptide according to claim 1, wherein the nuclear localization signal comprises apoptin.

7. The chimeric peptide according to claim 1, wherein the nuclear localization signal comprises a 40-amino-acid C-terminal fragment of apoptin.

8. The chimeric peptide according to claim 1, wherein the nuclear localization signal comprises TAT-apoptin.

9. The chimeric peptide according to claim 1, wherein the nuclear localization signal is selected from the group consisting of at least one of apoptin 1-121, apoptin 33-121, apoptin 82-121, apoptin 97-121, apoptin 106-121, apoptin 111-121, apoptin 1-31 linked to 83-121, and apoptin 1-31 linked to 32 to 83.

10. The chimeric peptide according to claim 1, wherein the functional cytolethal distending toxin comprises a *Salmonella* functional cytolethal distending toxin having deletions of at least one *Salmonella* functional cytolethal distending toxin nuclear localization signal.

11. The chimeric peptide according to claim 1, wherein the flexible linker comprises a flexible linker GGGGS(×3) SEQ ID NO: 004.

12. The chimeric peptide according to claim 1, wherein the chimeric peptide further comprises a secretion signal.

13. The chimeric peptide according to claim 12, wherein the nuclear localization signal from apoptin is selected from the group consisting of at least one of apoptin 1-121, apoptin 33-121, apoptin 82-121, apoptin 97-121, apoptin 106-121, apoptin 111-121, apoptin 1-31 linked to 83-121, and apoptin 1-31 linked to 32 to 83.

14. The chimeric peptide according to claim 1, wherein the functional cytolethal distending toxin comprises cldtB and the nuclear localization signal is selected from the group consisting of a 40-amino-acid C-terminal fragment of apoptin, TAT-apoptin, apoptin 1-121, apoptin 33-121, apoptin 82-121, apoptin 97-121, apoptin 106-121, apoptin 111-121, apoptin 1-31 linked to 83-121, and apoptin 1-31 linked to 32 to 83.

15. An antineoplastic chimeric peptide comprising a C-terminal fusion of a *Salmonella* cytolethal distending toxin subunit and at least one additional cytolethal distending toxin subunit, and a nuclear localization signal from apoptin, separated from the C-terminal fusion by a flexible peptide linker, the chimeric peptide being a functional cytoletal distending toxin and being terminated with a cysteine.

16. The chimeric peptide according to claim 15, wherein the functional cytolethal distending toxin comprises *Salmonella* typhoid toxin cytolethal distending toxin subunit B (cldtB) together with sty, ttsA, pltA and pltB.

17. The chimeric peptide according to claim 15, wherein the flexible linker comprises GGGGS(×3), SEQ ID NO: 004.

18. The chimeric peptide according to claim 15, contained in a pharmaceutically acceptable dosage form.

* * * * *

SEQUENCE LISTING

```
<160> NUMBER OF SEQ ID NOS: 4

<210> SEQ ID NO 1
<211> LENGTH: 11
<212> TYPE: PRT
<213> ORGANISM: Human immunodeficiency virus

<400> SEQUENCE: 1

Tyr Gly Arg Lys Lys Arg Arg Gln Arg Arg Arg
1               5                   10

<210> SEQ ID NO 2
<211> LENGTH: 9
<212> TYPE: PRT
<213> ORGANISM: Artificial Sequence
<220> FEATURE:
<223> OTHER INFORMATION: GM-CSF (GM- CSFR)

<400> SEQUENCE: 2

Cys Ala Tyr His Arg Leu Arg Arg Cys
1               5

<210> SEQ ID NO 3
<211> LENGTH: 12
<212> TYPE: PRT
<213> ORGANISM: Clostridium difficile

<400> SEQUENCE: 3

Cys Gln Thr Ile Asp Gly Lys Lys Tyr Tyr Phe Asn
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Flexible Linker

<400> SEQUENCE: 4

Gly Gly Gly Gly Ser Gly Gly Gly Gly Ser Gly Gly Gly Gly Ser
1               5                   10                  15
```